US008343761B2

(12) United States Patent
Tsuchiya et al.

(10) Patent No.: US 8,343,761 B2
(45) Date of Patent: Jan. 1, 2013

(54) METHODS OF GENERATING AND USING ANTIBODY-PRODUCING CELLS

(75) Inventors: Masayuki Tsuchiya, Tokyo (JP); Masami Suzuki, Shizuoka (JP); Kenji Yoshida, Shizuoka (JP); Etsuko Fujii, Shizuoka (JP); Miho Watanabe, Kanagawa (JP); Koichi Matsubara, Helios (SG); Yu Jau Chen, Helios (SG); Juliana Sim, Helios (SG)

(73) Assignees: Chugai Seiyaku Kabushiki Kaisha, Tokyo (JP); Pharmalogicals Research Pte. Ltd., Helios (SG); CIEA International Inc., Kanagawa (JP)

( * ) Notice: Subject to any disclaimer, the term of this patent is extended or adjusted under 35 U.S.C. 154(b) by 0 days.

(21) Appl. No.: 13/187,677

(22) Filed: Jul. 21, 2011

(65) Prior Publication Data
US 2012/0015402 A1 Jan. 19, 2012

Related U.S. Application Data

(62) Division of application No. 11/587,701, filed as application No. PCT/JP2005/007962 on Apr. 27, 2005, now Pat. No. 8,008,076.

(30) Foreign Application Priority Data

Apr. 27, 2004 (JP) ................................ 2004-132019

(51) Int. Cl.
*C12N 5/06* (2006.01)
*A01K 67/00* (2006.01)
*C12N 5/00* (2006.01)

(52) U.S. Cl. ............................. 435/326; 800/7; 435/378
(58) Field of Classification Search .................. None
See application file for complete search history.

(56) References Cited

U.S. PATENT DOCUMENTS

| 5,495,002 | A | 2/1996 | Kobrin et al. |
| 6,676,927 | B1 | 1/2004 | Ravetch |
| 8,008,076 | B2 | 8/2011 | Tsuchiya et al. |
| 2002/0193296 | A1 | 12/2002 | Xu et al. |
| 2006/0235207 | A1 | 10/2006 | Tsuchiya et al. |
| 2008/0187537 | A1 | 8/2008 | Tsuchiya et al. |

FOREIGN PATENT DOCUMENTS

| EP | 0 236 637 | 9/1987 |
| EP | 1 338 198 | 8/2003 |
| JP | 6-141884 | 5/1994 |
| WO | WO 00/20460 | 4/2000 |
| WO | WO 01/68682 | 9/2001 |
| WO | WO 02/43477 | 6/2002 |
| WO | WO 2004/032857 | 4/2004 |
| WO | WO 2004/048571 | 6/2004 |

OTHER PUBLICATIONS

Abe, "DNA o Mochiita Shuyo Tokuiteki Kogen ni Taisuru Men'eki Yudo B Saibosei Akusei Shuyo o Model ni," *Sankyo Seimei Kagaku Kenkyu Shinko Zaidan Kenkyu Hokokushu*, 11:213-219 (1998).
Åman et al., "Epstein-Barr Virus Susceptibility of Normal Human B Lymphocyte Populations," *J. Exp. Med.*, 159:208-220 (1984).
Better et al., "*Escherichia coli* Secretion of an Active Chimeric Antibody Fragment," *Science*, 240:1041-1043 (1988).
Bird et al., "Single-Chain Antigen-Binding Proteins," *Science*, 242:423-426 (1988).
Bonner et al., "Laser Capture Microdissection: Molecular Analysis of Tissue," *Science*, 278:1481-83 (1997).
Borsos, "Immunoglobulin Classes and Complement-Fixing Activity," in *Progress in Immunology*, Academic Press, New York, 841-848 (1971).
Brändlein et al., "Natural IgM Antibodies and Immunosurveillance Mechanisms Against Epithelial Cancer Cells in Humans," *Cancer Research*, 63:7995-8005 (2003).
Brittenden et al., "Natural Killer Cells and Cancer," *Cancer*, 77:1226-1243 (1996).
Cerundolo et al., "Functional Activity in vivo of Effector T Cell Populations III. Protection Against Moloney Murine Sarcoma Virus (M-MSV)-Induced Tumors in T Cell Deficient Mice by the Adoptive Transfer of a M-MSV-Specific Cytolytic T Lymphocyte Clone," *Eur. J. Immunol.*, 17:173-178 (1987).
Chen et al., "A Testicular Antigen Aberrantly Expressed in Human Cancers Detected by Autologous Antibody Screening," *Proc. Natl. Acad. Sci. USA*, 94:1914-1918 (1997).
Coronella, "Evidence for an Antigen-driven Humoral Immune Response in Medullary Ductal Breast Cancer," *Cancer Research*, 61:7889-7899 (2001).
Coronella et al., "Antigen-Driven Oligoclonal Expansion of Tumor-Infiltrating B Cells in Infiltrating Ductal Carcinoma of the Breast," *J. Immunol.*, 169:1829-36 (2002).
Depraetere et al., "Human B Cell Growth and Differentiation in the Spleen of Immunodeficient Mice," *J. Immunol.*, 166:2929-2936 (2001).
Donze et al., "Human and Nonhuman Primate Lymphocytes Engrafted Into SCID Mice Reside in Unique Mesenteric Lymphoid Structures," *J. Immunol.*, 161:1306-1312 (1998).
Green et al., "Monoclonal Antibody Therapy for Solid Tumors," *Cancer Treatment Reviews*, 26:269-286 (2000).

(Continued)

*Primary Examiner* — Michail Belyavskyi
(74) *Attorney, Agent, or Firm* — Fish & Richardson P.C.

(57) ABSTRACT

An objective of the present invention is to facilitate the acquisition of antibody-producing cells that are infiltrating virus-infected cells, cancer cells, abnormal cells forming a benign hyperplasia, and the like, and to improve the efficiency of the production of antibodies as well as nucleic acids encoding them from the antibody-producing cells.
The present inventors discovered that, when cancer tissues comprising infiltrating lymphocytes are transplanted into highly immunodeficient animals that do not have T cells, B cells, and NK cells and further exhibit a low IFN production ability, the differentiation and proliferation of infiltrating lymphocytes are unexpectedly promoted, and the number of plasma cells that produce antibodies recognizing cancer tissues increases dramatically, plasma cells can be separated easily, and antibodies or nucleic acids encoding them can be easily prepared from the plasma cells.

35 Claims, 19 Drawing Sheets

OTHER PUBLICATIONS

Grossman, "Leukemia Progression: Role of Tissue Disorganization," *Haematol. Blood Transfus.*, 31:289-298 (1987).

Hanna N., "Regulation of Natural Killer Cell Activation: Implementation for the Control of Tumor Metastasis," *Nat. Immun. Cell Growth Reg.*, 3:22-33 (1983/1984).

Hansen et al., "The tumor-infiltrating B cell response in medullary breast cancer is oligoclonal and directed against the autoantigen actin exposed on the surface of apoptotic cancer cells," *Proc. Natl. Acad. Sci. USA*, 98:12659-12664 (2001).

Henderson et al., "Efficiency of Transformation of Lymphocytes by Epstein-Barr Virus," *Virology*, 76:152-163 (1977).

Hiramatsu et al., "Complete reconstitution of human lymphocytes from cord blood CD34+ cells using the NOD/SCID/gammacnull mice model," *Blood*, 102(3):873-880 (2003).

Hurlimann et al., "Mononuclear Cells Infiltrating Human Mammary Carcinomas: Immunohistochemical Analysis with Monoclonal Antibodies," *Int. J. Cancer*, 35:753-762 (1985).

Husby et al., "Tissue T and B Cell Infiltration of Primary and Metastatic Cancer," *J. Clin. Invest.*, 57:1471-1482 (1976).

Ichinomiya et al., "VII. Men'eki Saibo 2. Laser Microdissection o Riyo shita Men'eki Soshiki no Atarashii Kaisekiho," *Annual Review Men'eki 2002*, 174-179 (2001).

Imahayashi et al., "Tumor-Infiltrating B-Cell-Derived IgG Recognizes Tumor Components in Human Lung Cancer," *Cancer Invest.*, 18:530-536 (2000).

Ingber et al., "Role of basal lamina in neoplastic disorganization of tissue architecture," *Proc. Natl. Acad. Sci. USA*, 78(6):3901-3905 (1981).

Ioachim, EMBASE Accession No. EMB-1977199257, *J. Natl. Cancer Inst.*, 57:465-75 (1976).

Ito et al., "NOD/SCID/$\gamma_c^{null}$ Mouse: An Excellent Recipient Mouse Model for Engraftment of Human Cells," *Blood*, 100: 3175-3182 (2002).

Jicha et al., "The Persistence of Human Peripheral Lymphocytes, Tumor Infiltrating Lymphocytes, and Colon Adenocarcinomas in Immunodeficient Mice," *J. Immunother (1991).*, 11:19-29 (1992).

Kanashima et al., "SCID-hu Mouse—Hito Zoketsu Men'ekikei Kenkyu eno Oyo," *Taisya*, 27:149-154 (1990).

Kiyoi et al., "NOG Mouse eno Ishu Ishokukei o Mochiita Hito Saitaiketsu CD34 Yosei Saibo kara no B Saibo Bunka Katei no Kaiseki," *Mukin Seibutsu (Journal of Germfree Life and AnotoBiology)*, 33:104-106 (2003) [English Abstract].

Kobari et al., "In vitro and in vivo evidence for the long-term multilineage (myeloid, B, NK, and T) reconstitution capacity of ex vivo expanded human CD34$^+$ cord blood cells," *Exp. Hematol.*, 28(12):1470-1480 (2000).

Kodera et al., "Antibody-Dependent Cell-Mediated Cytotoxicity for Human Monolayer Target Cells Bearing Blood Group and Transplantation Antigens and for Melanoma Cells," *Int. J. Cancer*, 16:579-592 (1975).

Koch et al., *American Journal of Pathology*, 137(5):1199-1213 (1990).

Kotlan et al., "Immunoglobulin variable regions usage by B-lymphocytes infiltrating a human breast medullary carcinoma," *Immunol. Lett.*, 65:143-151 (1999).

Kreider et al., "Relationship of tumor leucocytic infiltration to host defense mechanisms and prognosis," *Cancer Metastasis Rev.*, 3:53-74 (1984).

Kubota et al., "High Human IgG Levels in Severe Combined Immunodeficient Mouse Reconstituted with Human Splenic Tissues from Patients with Gastric Cancer," *Jpn. J. Cancer Res.*, 83:300-303 (1992).

Larrick et al., "Therapeutic Human Antibodies Derived from PCR Amplification of B-Cell Variable Regions," *Immunol. Rev.*, 130:69-85 (1992).

Lubaroff et al., "Survival of Human Prostate Carcinoma, Benign Hyperplastic Prostate Tissues, and IL-2-Activated Lymphocytes in SCID Mice," *Prostate.*, 27:32-41 (1995).

Luo et al., "Gene expression profiles of laser-captured adjacent neuronal subtypes," *Nat. Med.*, 5:117-122 (1999).

Maloney et al., "IDEC-C2B8 (Rituximab) Anti-CD20 Monoclonal Antibody Therapy in Patients with Relapsed Low-Grade Non-Hodgkin's Lymphoma," *Blood*, 90: 2188-2195 (1997).

Mallison et al., *Infection and Immunity*, 59(11):4019-4025 (1991).

Marks et al., "By-passing Immunization. Human Antibodies from V-gene Libraries Displayed on Phage," *J. Mol. Biol.*, 222:581-597 (1991).

Nabholz et al., "Cytolytic T Lymphocytes," *Ann. Rev. Immunol.*, 1:273-306 (1983).

Nzula et al., "Antigen-driven Clonal Proliferation, Somatic Hypermutation, and Selection of B Lymphocytes Infiltrating Human Ductal Breast Carcinomas," *Canc. Res.*, 63:3275-80 (2003).

Obiakor et al., *Analytical Biochemistry*, 306:55-62 (2002).

Owens et al., "The genetic engineering of monoclonal antibodies," *J. of Immunol. Methods*, 168:149-165 (1994).

Patki et al., "Evidence for B Cell Oligoclonality in the Blood and Joints of Patients with Rheumatoid Arthritis," *Ann. N.Y. Acad. Sci.*, 815:472-474 (1997).

Plasma cell. In Webster's New World™ Medical Dictionary, Retrieved from the Internet on Feb. 27, 2008 at: http://www.credoreference.com/entry/2438767 (2003).

Punt et al., "Anti-tumor antibody produced by human tumor-infiltrating and peripheral blood B lymphocytes," *Cancer Immunol. Immunother.*, 38:225-232 (1994).

Ratech, "Rapid Cloning of Rearranged Immunoglobulin Heavy Chain Genes From Human B-Cell Lines Using Anchored Polymerase Chain Reaction," *Biochem. Biophys. Res. Commun.*, 182:1260-1263 (1992).

Roitt et al., "The Cellular Basis of Immunological Responses," *Lancet*, 2:367-371 (1969).

Rosenberg et al., "Use of Tumor-Infiltrating Lymphocytes and Interleukin-2 in the Immunotherapy of Patients with Metastatic Melanoma. A Preliminary Report," *N. Engl. J. Med.*, 319:1676-1680 (1988).

Sahin et al., "Serological Identification of Human Tumor Antigens," *Curr. Opin. Immunol.*, 9:709-716 (1997).

Shimamura et al., "Hito Lymph-Kyu no Shinseiji SCID Mouse eno Ishoku," *Menekisei Shinkei Shikkan ni Kansuru Kenkyu*, Kenkyu Houkokusyo, 106-108 (1995).

Skerra et al., "Assembly of a Functional Immunoglobulin $F_v$ Fragment in *Escherichia coli*," *Science*, 240:1038-1041 (1988).

Tachikawa et al., "Laser Microdissection-ho no Gan Chiryo eno Oyo," *Hematology & Oncology*, 42:565-571 (2001).

Umemoto et al., "Jusho Fukugo Men'eki Fuzen (SCID) Mouse ni okeru Hito Men'kei Kiko Saikochiku ni Kansuru Kisoteki Kento," *Biotherapy*, 5:488-492 (1991).

Van Pel et al., "Genes Coding for Tumor Antigens Recognized by Cytolytic T Lymphocytes," *Immunol. Rev.*, 145:229-250 (1995).

Vose et al., "Suppressor Cell Activity of Lymphocytes Infiltrating Human Lung and Breast Tumours," *Int. J Cancer*, 24:579-585 (1979).

Walton et al., "Unrestricted usage of immunoglobulin heavy chain genes in B cells infiltrating the wall of atherosclerotic abdominal aortic aneurysms," *Atherosclerosis*, 135:65-71 (1997).

Whiteside et al., "Clonal analysis and in situ characterization of lymphocytes infiltrating human breast carcinomas," *Cancer Immunol. Immunother.*, 23:169-178 (1986).

Williams et al., "Engraftment of Human Tumor-Infiltrating Lymphocytes and the Production of Anti-Tumor Antibodies in SCID Mice," *J. Immunol.*, 156:1908-1915 (1996).

Winter et al., "Man-made antibodies," *Nature*, 349:293-299 (1991).

Wolf et al., "Lymphocyte subpopulations infiltrating squamous carcinomas of the head and neck: Correlations with extend of tumor and prognosis," *Otolaryngol. Head Neck Surg.*, 95:142-152 (1986).

Wu et al., "Cloning, isolation and characterization of human tumor in situ monoclonal antibodies," *Cancer Immunol. Immunother.*, 51:79-90 (2002).

Yasuda et al., "Tumor-Infiltrating B Lymphocytes as a Potential Source of Identifying Tumor Antigen in Human Lung Cancer," *Cancer Research*, 62:1751-1756 (2002).

Zhang et al., "A Human Monoclonal Antimelanoma Single-Chain Fv Antibody Derived from Tumor-infiltrating Lymphocytes," *Cancer Res.*, 55:3584-91 (1995).

International Search Report for App. Ser. No. JP2003/014919, mailed Jan. 13, 2004, 2 pages.
International Preliminary Report on Patentability for App. Ser. JP2003/014919, dated Apr. 1, 2004, 3 pages.
USPTO Non-Final Office Action in U.S. Appl. No. 10/535,764, dated Jul. 5, 2007, 10 pages.
Fish & Richardson P.C., Amendment in Reply to Action dated Jul. 5, 2007 in U.S. Appl. No. 10/535,764, filed Dec. 4, 2007, 8 pages.
USPTO Final Office Action in U.S. Appl. No. 10/535,764, dated Mar. 31, 2008, 16 pages.
Fish & Richardson P.C., Amendment in Reply to Action dated Mar. 31, 2008 in U.S. Appl. No. 10/535,764, filed Apr. 24, 2009, 14 pages.
USPTO Non-Final Office Action in U.S. Appl. No. 10/535,764, dated Jul. 24, 2009, 16 pages.
Fish & Richardson P.C., Amendment in Reply to Action dated Jul. 24, 2009 in U.S. Appl. No. 10/535,764, filed Jan. 25, 2010, 14 pages.
USPTO Final Office Action in U.S. Appl. No. 10/535,764, dated Apr. 29, 2010, 11 pages.
Fish & Richardson P.C., Amendment in Reply to Action dated Apr. 29, 2010, in U.S. Appl. No. 10/535,764, filed Dec. 21, 2010, 29 pages.
International Search Report for App. Ser. No. JP2005/007962, mailed Jul. 12, 2005, 2 pages.
International Preliminary Report on Patentability for App. Ser. No. PCT/JP2005/007962, 6 pages.
European Search Report for App. Ser. No. EP 05 73 7209, dated Jan. 8, 2009, 5 pages.
USPTO Restriction Requirement in U.S. Appl. No. 11/587,701, dated May 4, 2009, 5 pages.
Fish & Richardson P.C., Response to Restriction Requirement dated May 4, 2009 in U.S. Appl. No. 11/587,701, filed Oct. 30, 2009, 1 page.
USPTO Non-Final Office Action in U.S. Appl No. 11/587,701, dated Feb. 18, 2010, 8 pages.
Fish & Richardson P.C., Amendment in Reply to Action dated Feb. 18, 2010 in U.S. Appl. No. 11/587,701, filed Aug. 11, 2010, 25 pages.
USPTO Notice of Allowance in U.S. Appl. No. 11/587,701, dated Oct. 20, 2010, 7 pages.
USPTO Notice of Allowance in U.S. Appl. No. 11/587,701, dated Apr. 22, 2011, 5 pages.
Carlson et al., "Anaplastic neoplasms arising from basal cell carcinoma xenotransplants into SCID-beige mice," *J. Cutan. Pathol.*, 29(5):268-78 (2002).
Katano et al., "Tumor growth inhibition by tumor-infiltrating B cells," *Journal of Japan Surgical Society*, 93(6):72 (1992) (with English translation).

NOG MOUSE

SCID MOUSE

METHODS OF GENERATING AND USING ANTIBODY-PRODUCING CELLS

CROSS-REFERENCE TO RELATED APPLICATIONS

This application is a divisional of U.S. application Ser. No. 11/587,701 (now U.S. Pat. No. 8,008,076), having a 371(c) date of Nov. 8, 2007, which is the National Stage of International Application No. PCT/JP2005/007962, filed on Apr. 27, 2005, which claims the benefit of Japanese Patent Application No. 2004-132019, filed on Apr. 27, 2004. The contents of each of the foregoing applications are hereby incorporated by reference in their entireties.

TECHNICAL FIELD

The present invention relates to the acquisition of antibody-producing cells. Moreover, the present invention relates to methods for producing antibodies and antibody-encoding nucleic acids from these antibody-producing cells.

BACKGROUND ART

The infiltration of lymphocytes into cancer and lesion tissues is a phenomenon which has been clinically known for a long time (Non-Patent Documents 1, 2, 3, 4, and 5). Moreover, numerous experimental and clinical data indicate that infiltrated lymphocytes attack cancer and lesion tissues (Non-Patent Documents 6, 7, and 8).

The main players of cellular immunity in cancer are cytotoxic T cells (CTL) and NK cells (Non-Patent Documents 9, 10, 11, and 12), while the main players of humoral immunity are antibodies produced by plasma cells (Non-Patent Documents 13, 14, and 15). Antibodies that recognize cancer antigens have been shown to be present in the serum of cancer patients and novel cancer antigens have been isolated using antibodies from cancer patients (Non-Patent Documents 16 and 17). Moreover, some of the antibodies produced by plasma cells that infiltrate cancer tissues have been demonstrated to bind to cancer cells (Non-Patent Documents 18, 19, and 20). In addition, antibodies such as Herceptin and Rituxan, which recognize antigens strongly expressed in cancers, have been developed as therapeutic drugs, demonstrating the utility of antibodies that recognize cancer-specific antigens (Non-Patent Documents 21 and 22).

Although attempts have been made to separate plasma cells that infiltrate cancer tissues and to continuously produce specific antibodies from those cells, these attempts have failed so far. Reasons for the failure include the inability to secure tumor-specific plasma cells (B lymphocytes) in sufficient numbers because of the difficulty of separating them from cancer tissues, and even if separation were successful to some extent, the instability of antibody production with methods that use EBV or hybridomas for immortalizing antibody-producing cells.

On the other hand, recombinant DNA technologies for creating antibodies having antigen-binding activities similar to those from cloned antibody-producing cells, namely methods for cloning antibody genes and preparing recombinant antibody proteins, are being established (Non-Patent Documents 23 and 24). Antibody genes such as Fv, scFv, Fab, IgG, or IgM (Non-Patent Documents 25, 26, and 27) can be produced by cloning genes encoding the variable regions of antibody genes. scFv, which is the smallest recombinant antibody molecule, has a structure in which a heavy chain variable region and a light chain variable region are joined by a linker.

Cloned B cells express a single antibody gene. Thus, it is easy to clone heavy chain and light chain variable regions from these cells. However, since B cells present in peripheral blood and B cells that infiltrate cancer tissues are cell groups (polyclones) producing various antibodies (Non-Patent Documents 28 and 29), it is extremely difficult to clone cancer-specific genes from these.

[Non-Patent Document 1] Hurliamnn et al. (1985) Int J Cancer 35:753.
[Non-Patent Document 2] Whiteside et al. (1986) Cancer Immunol Immunother 23:169,
[Non-Patent Document 3] Wolf et al. (1986) Otolaryngol Head Neck Surg 95:142.
[Non-Patent Document 4] Husby et al (1976) J Clin Invest 57:1471,
[Non-Patent Document 5] Vose et al. (1979) Int J Cancer 24:579.
[Non-Patent Document 6] Rosenberg et al. (1988) New England J Med 319:1676.
[Non-Patent Document 7] Van Pel et al, (1995) Immunol Reviews 145:229.
[Non-Patent Document 8] Kreider et al. (1984) Cancer Metastasis Rev 3:53.
[Non-Patent Document 9] Nobholz and MacDonald (1983) Annu Rev Immunol 1:273.
[Non-Patent Document 10] Gerundolo et al. (1987) Eur J Immunol 17:173.
[Non-Patent Document 11] Hanna et al. (1984) Cancer Inv Met 309.
[Non-Patent Document 12] Brittenden et al. (1996) Cancer 77:1226.
[Non-Patent Document 13] Roitt et al. (1969) Lancet 2:367.
[Non-Patent Document 14] Borsos (1971) Progress in Immunology: p841. New York, Academic Press.
[Non-Patent Document 15] Kodera and Bean (1975) Int J Cancer 16:579.
[Non-Patent Document 16] Yao-Tseng Chen et al. (1997) Proc Natl Acad Sci USA 94:1914.
[Non-Patent Document 17] Ugur Sahin et al. (1997) Cancer 9:709,
[Non-Patent Document 18] Williams et al. (1996) Jour Immunol 156:1908.
[Non-Patent Document 19] Imahayashi et al. (2000) Cancer Invest 18:530.
[Non-Patent Document 20] Yasuda et al. (2002) Cancer Res 62:1751.
[Non-Patent Document 21] Green et al. (2000) Cancer Treat Rev 26:269.
[Non-Patent Document 22] Maloney et al. (1997) Blood 90:2188.
[Non-Patent Document 23] Marks et al. (1991) J Mol Biol 222:581.
[Non-Patent Document 24] Larrick et al. (1992) Immunol reviews 130:69.
[Non-Patent Document 25] Skerra et al. (1988) Science 240:293.
[Non-Patent Document 26] Bird et al, (1988) Science 242:243.
[Non-Patent Document 27] Better et al. (1988) Science 240:104.
[Non-Patent Document 28] Kotlan et al. (1999) Immunol Lett 65:143.
[Non-Patent Document 29] Hansen et al. (2001) Pro Natl Acad Sci USA 98:12659.
[Non-Patent Document 30] Blood, 100: 3175-3182, 2002.

DISCLOSURE OF THE INVENTION

Problems to be Solved by the Invention

An objective of the present invention is to facilitate the acquisition of antibody-producing cells infiltrating lesion tissues framed by abnormal cells (such as virus-infected cells, cancer cells, and abnormal cells forming benign hyperplasia). An objective of the present invention is to provide methods for producing antibodies from antibody-producing cells infiltrating lesion tissues, and nucleic acids encoding these antibodies. In addition, the present invention provides antibodies produced based on antibody-producing cells infiltrating lesion tissues, and nucleic acids encoding these antibodies. Moreover, an objective of the present invention is to provide therapeutic or diagnostic compositions against lesion tissues using antibody-producing cells infiltrating lesion tissues, antibodies obtained based on these cells, and nucleic acids encoding these antibodies.

Means to Solve the Problems

In view of the aforementioned problems, the present inventors conducted dedicated research to discover that, when cancer tissues comprising infiltrating lymphocytes are transplanted into the highly immunodeficient NOD/SCID/$\gamma_c^{null}$ mice (Non-Patent Document 30, referred to as "NOG mice" in the present application) which do not have any T cells, B cells, or NK cells and which exhibit a low IFN production ability, the differentiation and proliferation of infiltrating lymphocytes are unexpectedly promoted, the number of plasma cells producing antibodies that recognize cancer tissues are dramatically increased, and that these cells can be easily separated. These findings led to the completion of the present invention. Specifically, the present invention is as described below:

(1) a method of proliferating plasma cells, wherein the method comprises the step of transplanting a tissue comprising plasma cells, blood comprising plasma cells, or plasma cells collected from a tissue or blood, into a highly immunodeficient non-human animal;

(2) the method of proliferation of (1), wherein the tissue is a lesion tissue comprising infiltrating lymphocytes;

(3) a method of producing cells which produce an antibody to an abnormal cell comprised in a lesion tissue, wherein the method comprises the steps of:

(a) transplanting a lesion tissue comprising infiltrating lymphocytes into a highly immunodeficient non-human animal;

(b) detecting the proliferation of plasma cells at the site of transplantation; and (c) recovering a lesion tissue comprising plasma cells from the site of transplantation;

(4) the method of production of (3), further comprising the step of:

(d) excising a plasma cell from the recovered lesion tissue and fusing the plasma cell with a partner cell;

(5) a method of producing a nucleic acid encoding an antibody against an abnormal cell comprised in a lesion tissue, or a portion of the antibody, wherein the method comprises the steps of:

(a) transplanting a lesion tissue comprising infiltrating lymphocytes into a highly immunodeficient non-human animal;

(b) detecting the proliferation of plasma cells at the site of transplantation;

(c) recovering a lesion tissue comprising plasma cells from the site of transplantation; and (d) obtaining a nucleic acid encoding an antibody from the recovered lesion tissue;

(6) the method of production of (5), wherein step (d) comprises collecting a nucleic acid encoding an antibody from plasma cells after excising the plasma cells from a lesion tissue;

(7) the method of production of (5) or (6) further comprising the step of:

(e) amplifying a nucleic acid encoding an antibody variable region using a nucleic acid encoding an antibody as a template and an oligonucleotide capable of amplifying the antibody variable region;

(8) a method of producing an antibody against an abnormal cell comprised in a lesion tissue, or a portion of the antibody, wherein the antibody is isolated from antibody-producing cells produced according to (3) or (4);

(9) a method of producing an antibody against an abnormal cell comprised in a lesion tissue, or a portion of the antibody, wherein the method comprises the following steps (a) to (c):

(a) introducing into an expression vector a nucleic acid obtained according to the method of production of any one of (5) to (7), or the nucleic acid that has been chimerized or humanized;

(b) transforming a host cell with a vector harboring the nucleic acid; and (c) producing an antibody by culturing the transformant;

(10) the method of production of (9), further comprising the step of:

(d) contacting the obtained antibody with a lesion tissue and selecting a transformant producing an antibody that binds to the lesion tissue;

(11) the method of any one of (3) to (10), wherein the abnormal cell comprised in the transplanted lesion tissue is a cancer cell, a cell forming a hyperplasia, or a virus-infected cell;

(12) the method of (11), wherein the cancer is a solid cancer or a blood cancer;

(13) the method of (12), wherein the solid cancer is a prostate cancer, stomach cancer, breast cancer, lung cancer, liver cancer, colorectal cancer, or pancreatic cancer;

(14) the method of (11), wherein the hyperplasia is a benign prostatic hyperplasia;

(15) the method of production of any one of (5) to (10), wherein the antibody or a portion thereof is an IgG an IgM, an Fab, an F(ab')2, an Fv, or a single chain Fv;

(16) the method of production of (9) or (10), wherein the produced antibody or antibody portion is a chimeric antibody, a humanized antibody, a human antibody, or a portion thereof;

(17) a nucleic acid produced according to the method of any one of (5) to (7);

(18) a nucleic acid encoding a chimeric antibody, a humanized antibody, or a human antibody, wherein the nucleic acid comprises the nucleic acid of (17);

(19) an antibody produced according to the method of any one of (8) to (10);

(20) the antibody of (19), which is an antibody against a prostate cancer cell, a stomach cancer cell, a breast cancer cell, a lung cancer cell, a liver cancer cell, a colorectal cancer cell, or a pancreatic cancer cell;

(21) the antibody of (20), which is an antibody against a prostate cancer cell;

(22) the antibody of (21), wherein the antibody recognizes a surface molecule of the prostate cancer cell line DU145;

(23) the antibody of any one of (19) to (22), which is an IgG, an IgM, an Fab, an (Fab')$_2$, an Fv, or a single chain Fv;

(24) the antibody of any one of (19) to (22), wherein the antibody comprises a variable region portion;
(25) the antibody of (23) or (24), which is a single chain Fv;
(26) a method of producing a therapeutic composition against a lesion tissue, wherein the method comprises the steps of:
   (a) transplanting a lesion tissue infiltrated by lymphocytes into a highly immunodeficient non-human animal;
   (b) detecting the proliferation of lymphocytes at the site of transplantation; and
   (c) recovering cells comprising lymphocytes from the site of transplantation;
(27) the method of (26), further comprising the step of:
   (d) culturing the recovered cells comprising lymphocytes in vitro to further proliferate the lymphocytes;
(28) the method of (26) or (27), wherein the lymphocytes comprise plasma cells;
(29) the method of any one of (26) to (28), wherein the lesion tissue is a cell forming a cancer or a hyperplasia, or a virus-infected cell;
(30) a therapeutic composition against a lesion tissue, wherein the composition is produced according to the method of any one of (26) to (29);
(31) an antibody against an abnormal cell comprised in a lesion tissue, wherein the antibody is comprised in a serum recovered from a highly immunodeficient non-human animal transplanted with a lesion tissue comprising plasma cells, blood comprising plasma cells, or plasma cells recovered from a lesion tissue or blood;
(32) the antibody of (31), which is a polyclonal antibody; and
(33) a therapeutic or diagnostic composition against a lesion tissue, wherein the composition comprises a nucleic acid of (17) or (18), or an antibody of any one of (19) to (25), (31), and (32) as an active ingredient.

Effects of the Invention

According to the present invention, plasma cells, which produce antibodies that recognize abnormal cells (such as cancer cells and abnormal cells forming benign hyperplasia) in polyclonal cell groups such as transplanted tissue fragments, can be selectively proliferated by transplanting lymphocyte-infiltrated lesion tissues into highly immunodeficient animals, and the plasma cells of interest can be easily separated. This easy separation of plasma cells further facilitates or enables the acquisition of antibodies recognizing antigens specific to lesion tissues and nucleic acids encoding these antibodies from the plasma cells. Moreover, plasma cells, antibodies, or nucleic acids which encode the antibodies acquired by the present invention contribute as novel therapeutic or diagnostic agents against lesion tissues.

BRIEF DESCRIPTION OF THE DRAWINGS

FIG. 14 shows photographs of tissue staining of cancer tissues using human antibodies present in mouse serum. a:

Reactivity of IgMs in the serum of mice transplanted with PLR0659 stomach cancer tissues with a colorectal cancer cell line; be Reactivity of IgMs in the serum of mice transplanted with PLR stomach cancer tissues with a stomach cancer cell line. The cell membrane of cancer cells indicated by the arrows was stained.

Figure 15:
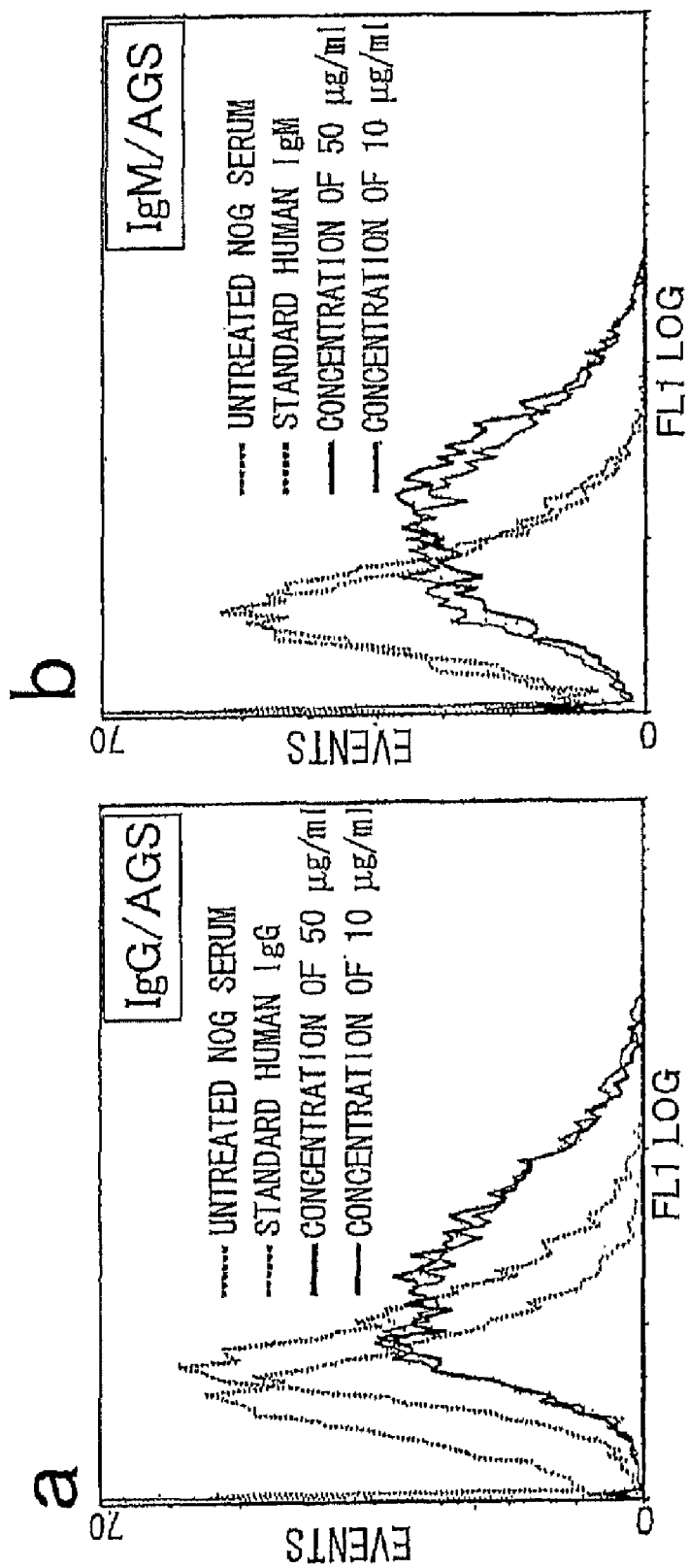

FIG. 15 shows an observation by flow cytometry of the staining of the cancer cell line AGS by human IgGs (a) and IgMs (b) from the serum of mice transplanted with PLR0530 stomach cancer tissue. Nearly the same staining properties were observed with antibody concentrations of 50 μg/ml and 10 μg/ml.

Figure 16:
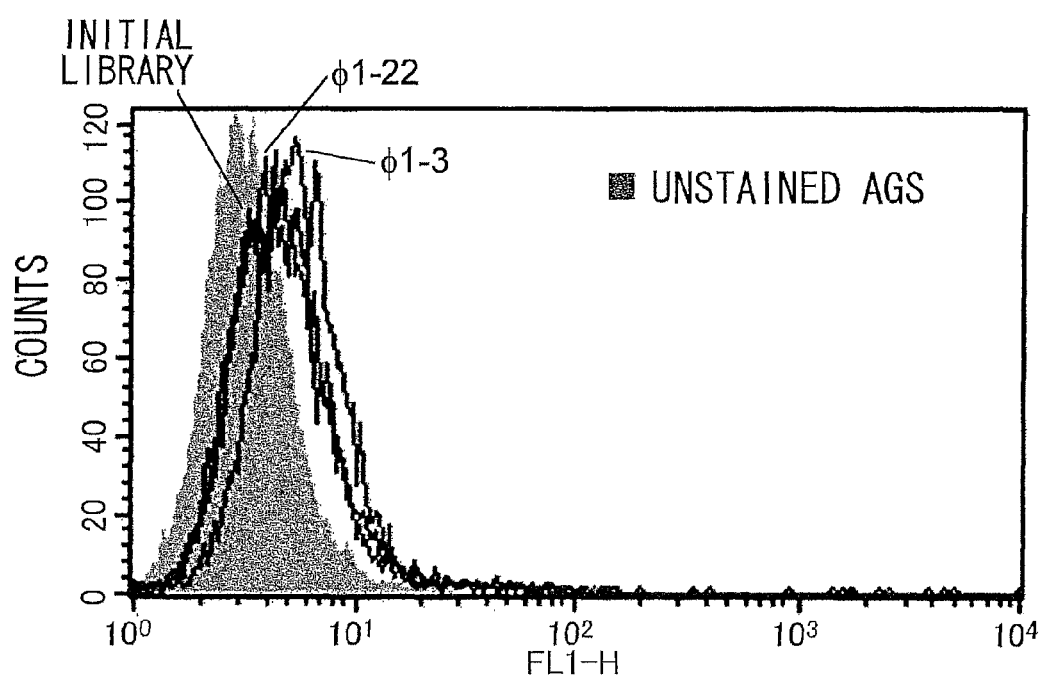

FIG. 16 is a graph showing a confirmation by flow cytometry of the binding of AGS cells to AGS cell-binding clones when these clones were isolated from a concentrated, selected library.

Figure 17:
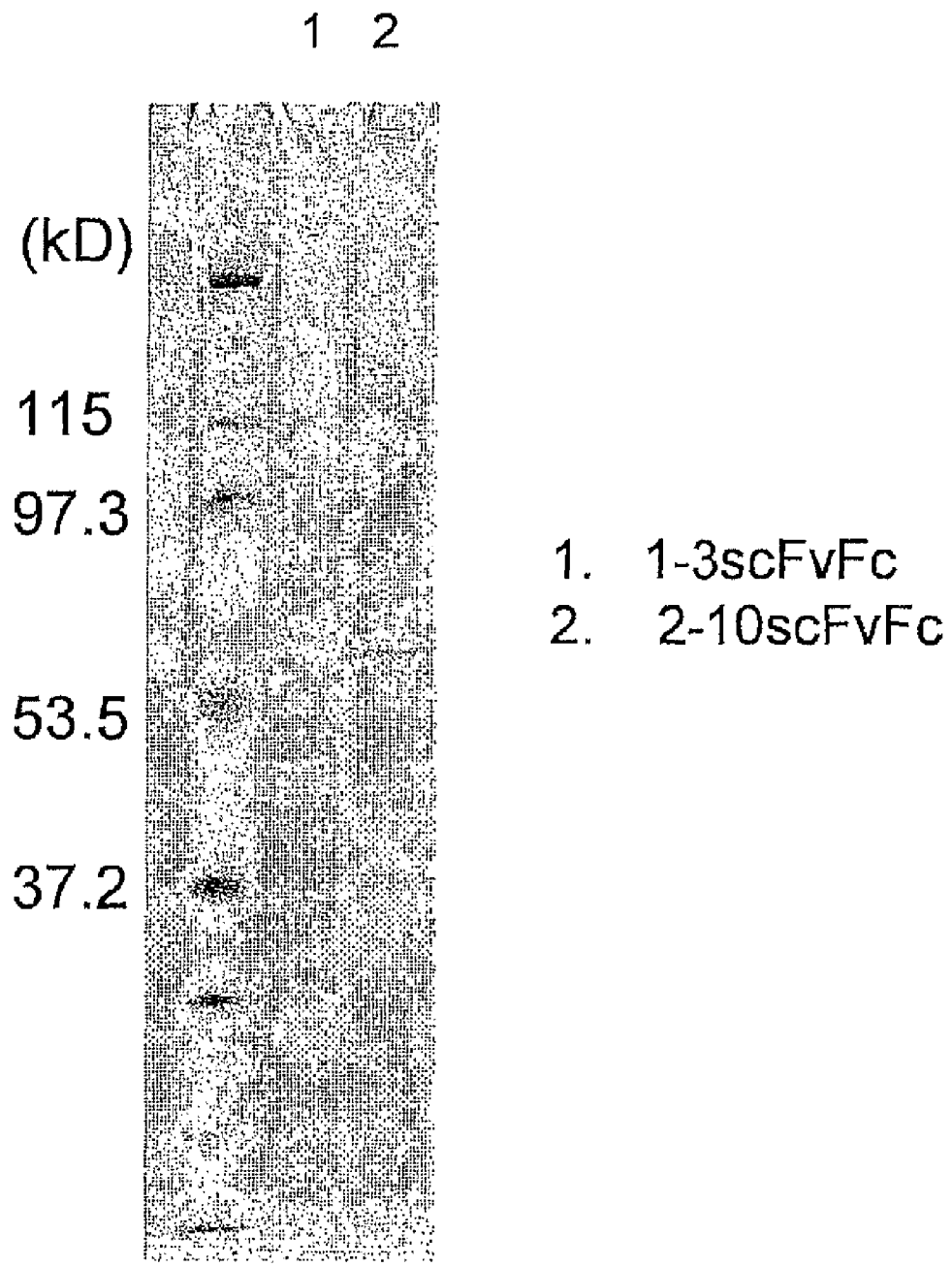

FIG. 17 is a photograph showing a silver staining of a Protein A-purified scFv fusion protein following SDS-PAGE separation.

Figure 18:
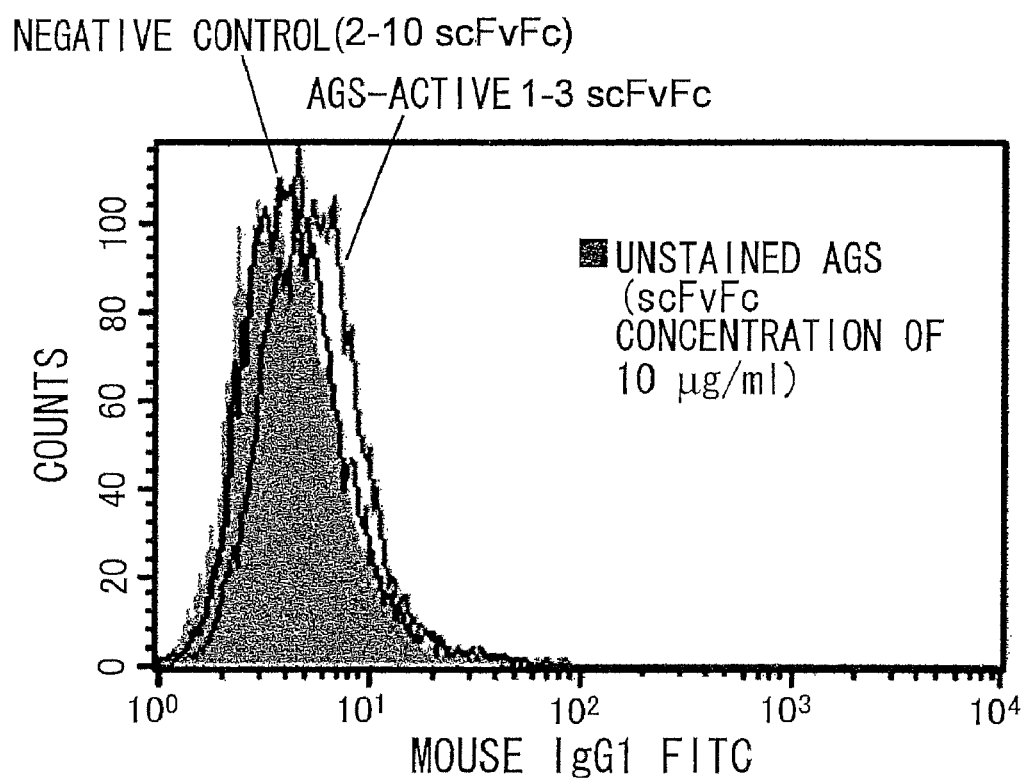

FIG. 18 is a graph showing a confirmation by flow cytometry of recombinant fusion proteins 1-3 scFv Fc that are bound to AGS cells.

Figure 19:
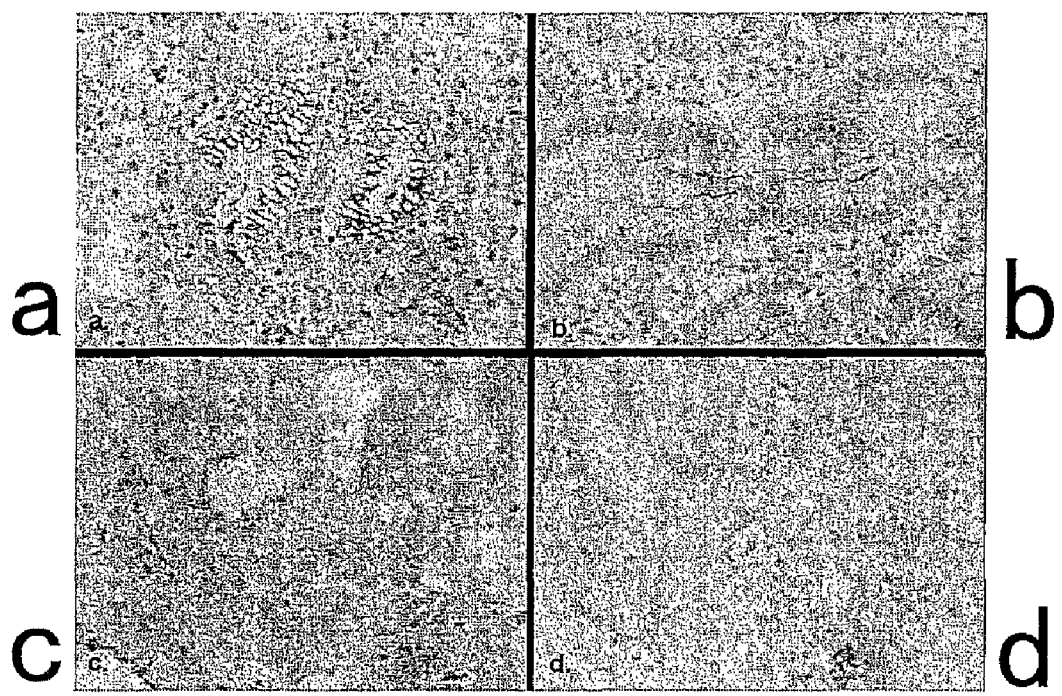

FIG. 19 shows an immunohistological staining of cancer tissues using chimeric antibodies. Tissues excised from stomach cancer patients (a and c), tissues excised from a duodenum cancer (b), and tissues excised from the colon (CRC) (d) were used as cancer tissues. Immunostaining confirmed that the chimeric antibodies react with the cytoplasm of stomach cancer cells, and with the luminal side of duodenum cancer and colon cancer cell membranes.

DETAILED DESCRIPTION

As a first aspect, the present invention provides a method of proliferating plasma cells, where the method comprises the step of transplanting tissues comprising plasma cells into a highly immunodeficient non-human animal.

Herein, "plasma cells" refer to cells which can produce antibodies, and the antibody class is not particularly restricted. Thus, the term "plasma cells" used in the present specification comprises: B cells in the early stages of B cell differentiation, expressing a μ chain on the cell surface as antigen receptor; B cells in which the transcription process has changed and IgM production has changed from membrane-type IgMs to secreted-type IgMs; mature B cells that have completed class-switching and secrete IgGs, IgAs, and IgMs; and B cells in the final stages of differentiation, capable of producing 2000 IgG molecules per second. In addition, the "proliferation of plasma cells" referred to herein comprises both the proliferation and differentiation of the aforementioned B cells.

Examples of tissues comprising plasma cells include cells and tissues containing substances that may be recognized as foreign matter by the body's immune system or cells and tissues containing degeneration products of organisms or biological substances, such as neoplasms. Examples of such comprise tissues forming a cancer or hyperplasia and cells infected with viruses. Since such cancers and virus-infected cells may form lesion sites in the body, tissue fragments from lesion sites of patients can be directly used as "plasma cell-comprising tissues". For example, the following types of lesions are preferable as "plasma cell-comprising tissues".

Solid cancer lesions
Blood cancer lesions
Hyperplasia lesions
Arteriosclerosis lesions
Inflammatory disease lesions
Metabolic disease lesions
Lesions formed by infectious pathogens
Autoimmune disease lesions In particular, solid cancer lesions and hyperplasia lesions are preferable as the aforementioned tissues. Examples of solid cancer lesions include lesions of prostate cancer, stomach cancer, breast cancer, lung cancer, liver cancer, colorectal cancer, and pancreatic cancer. Lesions forming benign hyperplasia, particularly lesions fanning benign prostatic hyperplasia are preferable as hyperplasia lesions. These tissues can be collected by surgical excision. For example, cancer tissues collected for examination by biopsy can be used as lesion tissues in the present invention. In addition, tissues excised from patients by surgical excision as a surgical treatment are also useful as lesion tissues.

Moreover, secondary inflammatory diseases are comprised in the inflammatory diseases. Examples of metabolic diseases include Alzheimer's disease that forms amyloid plaques.

Examples of infectious pathogens include, but are not limited to, HCV (human hepatitis C virus), HBV (human hepatitis B virus), and HIV (human immunodeficiency virus). Tissues or cells invaded by infectious pathogens such as these viruses can be collected by biopsy or from the blood.

In addition to lesion sites derived from patients, those artificially formed in laboratory animals and the like may also be used as the "plasma cell-comprising tissues". Herein, examples of lesion sites artificially formed in laboratory animals include those formed by artificially transplanting heterologous cells or tissues into animals, and those formed by expressing an artificially-introduced exogenous gene either systemically or at a specific sites such as in tissues. Moreover, lesion tissues can also be formed by infecting laboratory animals with viruses.

The aforementioned "plasma cell-comprising tissues" are indicated as an example of a most typical sample when collecting lymphocytes and plasma cells as starting cells to be proliferated. However, not only lymphocytes and plasma cells that are infiltrating tissues such as lesions, but also lymphocytes and plasma cells present in blood or those present separated from such tissues or blood, may be used as starting cells. Although the terms "plasma cell-comprising (or plasma cell-infiltrated) tissues" and "lymphocyte-comprising (or lymphocyte-infiltrated) tissues" are used below in the present specification to indicate samples serving as starting cells to proliferate plasma cells, these terms encompass blood comprising plasma cells and the like, or plasma cells themselves separated from tissues or blood. Thus, tissues or blood comprising plasma cells and the like or plasma cells and such separated from these tissues or blood may be used in transplantations into the highly immunodeficient non-human animals described below. A "highly immunodeficient non-human animal" indicates an animal having an activity that can proliferate plasma cells from transplanted tissues without rejecting the transplanted tissues or cells, examples of which include non-human animals not possessing T cells, B cells, and NK cells and demonstrating a low IFN production ability, specifically NOG mice. Although examples using mice are indicated in the present application, examples of non-human animals other than mice include monkeys, pigs, dogs, rabbits, guinea pigs, and rats. Furthermore, hereinbelow in the present specification, "highly immunodeficient non-human animals" may simply be referred to as "highly immunodeficient animals" for convenience.

There are no particular limitations on transplantations into highly immunodeficient non-human animals, provided that the site of transplantation allows the proliferation of plasma cells; however, the transplantation can be carried out subcutaneously as that would be convenient for transplantation procedures and subsequent collection. Here, the transplanted plasma cells proliferate predominantly at the sites of transplantation without requiring any particular selection pressure. The present inventors discovered that this degree of plasma proliferation (or degree of accumulation) closely correlates with the antibody titer in the serum of the highly immunodeficient animals (antibody titer of antibodies derived from transplanted tissues). Consequently, whether or not plasma cells at the site of transplantation in the highly immunodeficient animals have proliferated can be verified by measuring the antibody titer in the serum collected from the animals. There are no limitations on the type of antibody measured, provided that a correlation with plasma cell proliferation can be observed; however, the antibodies are preferably IgMs or IgGs. Antibody titer can be measured by a method widely known to those skilled in the art. For example, IgMs or IgGs can be measured by selecting a method from among known methods such as single radial immunodiffusion (SRID), turbidimetric immunoassay (TIA), laser nephelometry, latex agglutination (LA), RIA, EIA, and ELISA. Use of commercially available assay kits enables easy and convenient measurement.

As the number of antibody-producing cells is increased at a site of transplantation in highly immunodeficient animals, the above-described present invention makes it easy to separate antibody-producing cells, which was difficult in the past. It also facilitates the production and such of antibodies against the lesion tissues described below.

As a second aspect, the present invention provides a method for producing antibody-producing cells. As previously described, the present inventors discovered that, when lesion tissues are transplanted into highly immunodeficient animals such as NOG mice, plasma cells infiltrating the lesion tissues can be advantageously proliferated. Thus, by using highly immunodeficient animals as a means for producing plasma cells, it becomes possible to amplify and recover the plasma cells, which were obtainable only in trace amounts in the past. Namely, the method of producing antibody-producing cells of the present embodiment comprises the steps of (a) transplanting a lesion tissue comprising infiltrating lymphocytes into a highly immunodeficient non-human animal; (b) detecting the proliferation of plasma cells at the site of transplantation; and (c) recovering the lesion tissue comprising the plasma cells from the site of transplantation.

Herein, the step of transplantation and the step of detecting the proliferation of plasma cells can be carried out in the same manner as in the aforementioned method of proliferating plasma cells. Recovery of the proliferated plasma cells may be carried out by recovering, from the site of transplantation, the transplanted tissue itself in which plasma cells have proliferated, or by selectively recovering the plasma cells. Microdissection is an example of a means for selectively recovering plasma cells. Microdissection is a technique for excising specific cells from a tissue section. For example, target cells can be isolated from frozen tissue sections using the Laser Microdissection (LMD) system. A system for excising tissue sections with an ultraviolet laser is commercially available. The use of this system, which involves specifying the region to be excised on a computer image under microscopic observation, makes it possible to excise any region from a tissue section.

A large number of plasma cells can be isolated by observing a specimen under a microscope and selecting a portion enriched with plasma cells. Specific plasma cells can be easily acquired by microdissection of single plasma cells.

The plasma cells recovered from the site of transplantation of highly immunodeficient animals are increased as compared to plasma cells in lesion tissues collected from patients and the like. As indicated in the forthcoming Examples, the increase in the number of plasma cells is accompanied by an increase in the titer of antibodies against the lesion tissues. Since plasma cells recovered in this manner produce antibodies against the lesion tissues more actively, these plasma cells can be effectively used as materials for obtaining antibodies or genes thereof, or the plasma cells themselves can be effectively used as a therapeutic composition for (treating) lesion tissues. Furthermore, when using the recovered plasma cells as a means for producing antibodies and the like, they are preferably fused with partner cells such as mouse or human myeloma cells to establish an antibody-producing cell line.

As a third aspect, the present invention provides a method of producing nucleic acids encoding antibodies or portions thereof. As previously described, plasma cells can be advantageously proliferated at a site of transplantation by transplanting lesion tissues infiltrated with lymphocytes into highly immunodeficient animals. Since such plasma cells that proliferated at a site of transplantation have an ability to produce antibodies against abnormal cells included in the lesion tissues, plasma cells recovered from the site of transplantation are a preferable cloning source of nucleic acids encoding antibodies against abnormal cells, or portions of these nucleic acids. In short, the method of the present invention for producing a nucleic acid encoding an antibody comprises the steps of: (a) transplanting a lesion tissue comprising infiltrating lymphocytes into a highly immunodeficient non-human animal; (b) detecting the proliferation of plasma cells at the site of transplantation; (c) recovering the lesion tissue comprising plasma cells from the site of transplantation; and (d) recovering the nucleic acid encoding the antibody from the recovered lesion tissue.

Transplantation of lesion tissues comprising infiltrating lymphocytes into highly immunodeficient non-human animals and detection of plasma cell proliferation at the site of transplantation can be carried out as in the aforementioned proliferation method and the like. Moreover, recovery of plasma cells from the site of transplantation may be carried out by recovering the lesion tissues themselves in which plasma cells have proliferated, from the site of transplantation or by selectively recovering plasma cells by microdissection and the like, as in the aforementioned method for producing plasma cells.

As a method for acquiring nucleic acids encoding antibodies, or portions thereof, from recovered lesion tissues or from selectively recovered plasma cells, chromosomes may be isolated from plasma cells or transcripts thereof and an antibody gene or a portion thereof may be obtained therefrom. However, since antibody genes obtainable from plasma cells are extremely small in amount, it is convenient to obtain the antibody gene, or portion thereof, after amplification. Methods for amplifying genes are known in the art. For example, the PCR method is preferred as a method for amplifying antibody genes. A method for isolating antibody genes using the PCR method is described below.

First, mRNAs are extracted from isolated plasma cells (B cells). cDNAs are synthesized by using the extracted mRNAs as a template to obtain a cDNA library. Commercially available kits are conveniently used for extracting mRNAs and for constructing the cDNA library. In this invention, mRNAs derived from a small number of plasma cells are used. In practice, mRNAs obtained from only few cells are extremely small in amount, and have low yields when directly purified. Therefore, mRNAs are usually purified after the addition of carrier RNAs that clearly contain no antibody genes. Alternatively, when a certain amount of RNA can be extracted, efficient extraction is possible even with only the RNAs of antibody-producing cells. The addition of carrier RNAs may not be required for extracting RNAs from, for example, 10 or more, 30 or more, preferably 50 or more antibody-producing cells.

By using the cDNA library thus obtained as a template, antibody genes can be amplified by the PCR method. Primers for amplifying antibody genes by the PCR method are known in the art. For example, primers for amplifying human antibody genes can be designed based on disclosures in research papers (J. Mol. Biol. (1991) 222, 581-597) and web sites (mrc-cpe.cam.ac.uk). These primers have different nucleotide sequences depending on the immunoglobulin subclass. Accordingly, when a cDNA library with an unknown subclass is used as a template, the PCR method is performed considering all possible immunoglobulin subclasses.

For example, to obtain genes encoding human IgG, primers that allow the amplification of genes encoding γ1 to γ5 as the heavy chain, and κ chain and λ chain as the light chains, can be used. For amplifying genes of the IgG variable region, a primer capable of annealing to a portion that corresponds to the hinge region is generally used as the 3' primer. An example of such a primer is the primer of SEQ ID NO: 55. A primer corresponding to each subclass, such as the primers shown in the Example 2 of the present application, can be used as the 5' primer.

The antibody gene or portion thereof can also be amplified directly, without the intermediary isolation of cDNAs, by RT-PCR using the above primers and mRNAs collected from plasma cells.

PCR products obtained using primers for amplifying genes of the respective heavy and light chain subclasses are considered as independent libraries. Using thus synthesized libraries, it is possible to reconstitute antibodies or portions thereof by combining the heavy chains and light chains.

As mentioned above, nucleic acids encoding "antibodies or portions thereof" are produced in the present invention. The nucleic acids may encode a whole antibody or an antibody portion. The antibodies are preferably IgGs or IgMs. Examples of preferable partial fragments of an antibody comprise Fab, $F(ab')_2$, and Fv which comprise variable regions equipped with the complementarity determining regions (CDRs) of the antibody.

As mentioned above, nucleic acids encoding the variable region of an antibody are preferred antibody fragments of the present invention. A complete immunoglobulin molecule can be reconstituted by obtaining nucleic acids encoding a variable region and linking the nucleic acids with nucleic acids encoding a constant region. Constant regions of antibodies within the same class have approximately the same structure. That is, the structure of the constant region has no effect on the antigen-binding activity. Accordingly, if the structure of the variable region of an antibody can be elucidated, antibodies having similar activity can be reconstituted through conjugation with a constant region that is already obtained.

Moreover, nucleic acids encoding antibodies, or portions thereof, of the present invention comprise genetically recombinant antibodies whose structures have been artificially modified. For example, they comprise single chain Fv (scFv) in which the variable regions of a heavy chain and light chain are linked by a linker. scFv can be obtained by ligating the V regions of the antibody H chain and L chain. In the scFv, the V regions of the H chain and L chain are ligated via a linker, and preferably via a peptide linker (Huston, J. S. et al., Proc. Natl. Acad. Sci. U.S.A (1988) 85, 5879-5883). Examples of the V regions of the H chain and L chain in the scFv are shown in the Examples of the present application, but are not limited thereto.

The peptide linker used to ligate the V regions may be any single-chain peptide comprising 12 to 19 residues. As shown in the scFv preparation example in Example 3, DNAs encoding scFv are obtained by: using as template a DNA encoding the entirety or a desired amino acid sequence of a DNA encoding the H chain or H chain V region or a DNA encoding the L chain or L chain V region of an aforementioned antibody; amplifying by PCR using a primer pair which defines both ends; then amplifying after combining a DNA encoding a peptide linker portion and a primer pair which defines both ends such that each end is linked to a H chain or L chain. Moreover, once DNAs encoding scFv are produced, expression vectors comprising them and hosts transformed with the expression vectors can be obtained following routine procedure.

Furthermore, in the case of antibody genes acquired in mammals and such other than humans, non-human animal-human chimeric antibody genes, in which the constant region genes is substituted with that of humans, and humanized antibody genes, which are formed by transplanting CDRs that constitute the variable regions of mammals other than humans into human variable regions, are also comprised in the antibody genes of the present invention. In addition, nucleic acids encoding antibodies in the present invention can also comprise artificial structures such as PNA, provided that their nucleotide sequences are maintained.

As a fourth aspect, the present invention provides a method for producing antibodies against abnormal cells contained in lesion tissues.

When the antibodies are polyclonal antibodies, they can be easily prepared by collecting blood from highly immunodeficient animals transplanted with lesion tissues comprising plasma cells, blood comprising plasma cells, or plasma cells recovered from lesion tissues or blood, and separating the serum. As also indicated in the Examples described below, antibodies against abnormal cells contained in lesion tissues were detected in highly immunodeficient animal blood when the lesion tissues were transplanted into highly immunodeficient animals and blood was collected from the animals. Thus, a method for preparing polyclonal antibodies against abnormal cells contained in lesion tissues can be carried out by separating serum from highly immunodeficient animals transplanted with lesion tissues.

Another method for producing antibodies is the method of preparing them from the aforementioned plasma cells produced based on lesion tissues or from fused cell lines of plasma cells and partner cells. Examples of partner cells include mouse myeloma cells and human myeloma cells. Antibody-producing cell lines which produce monoclonal antibodies can be prepared by fusing partner cells with cloned plasma cells. Isolation and purification of target antibodies against abnormal cells present in lesion tissues such as cancer from such fusion cell lines of plasma cells and partner cells can be carried out by affinity chromatography and such using, for example, the binding activity to abnormal cells of cancer and such, or to their surface molecules. Moreover, in a different method for producing antibodies, antibodies are artificially produced based on genes encoding the aforementioned antibodies or portions thereof. Specifically, this method comprises the steps of: introducing, into an expression vector, nucleic acids encoding the aforementioned antibodies or portions thereof, or nucleic acids in which the nucleic acids have been chimerized or humanized; transforming host cells with vectors carrying the aforementioned nucleic acids; and producing antibodies by culturing the transformants.

Expression vectors that can be used herein need to comprise units that regulate the transcription and translation of genetic information, such as promoters and terminators. For example, when microorganisms belonging to the *Escherichia* genus such as *E. coli* are used as hosts, plasmids of the pBR or pUC series can be used as plasmid vectors, and any promoters selected from those such as lac, trp, tac, trc, λ phage PL, and PR can be used. Terminators may originate from trpA, phage, and rrnB ribosomal RNA.

When the hosts are *Bacillus* microorganisms such as *B. subtilis*, plasmids such as those of the pUB110 and pC194 series can be used, and genes may be integrated into chromosomes in some cases. Promoters and terminators may be derived from apr, npr, amy, and such.

Examples of other prokaryotic cells comprise microorganisms such as *Pseudomonas* (e.g. *P. putida, P. cepacia*; pKT240 vectors, and such), *Brevibacteria* (e.g. *B. lactofermentum*; pAJ43), *Corynebacteria* (e.g. *C. glutamicum*; pCS11, pCB101), *Streptococcus* (e.g. pHV1301, pGK1), *Lactobacillaceae* (e.g. pAMI31), *Rhodococcus* (e.g. plasmids isolated from *R. rhodochrous* (J. Gen. Microbiol, 138: 1003 (1992)), *Streptomyces* (e.g. *S. lividans, S. virginiae*; pIJ486, pKC1064, pUWL-KS), *Enterobacter, Erwinia, Klebsiella, Proteus, Salmonella* (e.g. *S. typhimurium*), *Serratia* (e.g. *S. marcescans*), and *Shigella*.

Among expression systems utilizing eukaryotic microorganisms, a system using *Saccharomyces cerevisiae* as a host, and plasmids from YRp, YEp, YCp, and YIp series is known. Therein, promoters and terminators such as ADH, GAPDH, PHO, GAL, PGK, and ENO can be used. Other microorganisms used in the expression vector systems of the present invention comprise *Kluyveromyces* (e.g. *K. lactis*; plasmids of the 2 μm, pKD1, pGKI1, and KARS series, and such), *Schizosaccharomyces* (e.g. *S. pombe*; pAUR224), *Zygosaccharomyces* (e.g. *Z. rouxii*; pSB3 and PH05 promoters from *S. cerevisiae*), *Hansenula* (e.g. *H. polymorpha*), *Pichia* (e.g. *P. pastoris*), *Candida* (e.g. *C. maltosa, C. tropicalis, C. utilis,* and *C. albicans*), *Aspergillus* (e.g. *A. oryzae, A. niger*), and *Trichoderma* (e.g. *T. reesei*), In another embodiment, plant cells may be used as hosts. For example, hosts may be plant cells derived from cotton, corn, potato, tomato, soybean, petunia, tobacco, and such. A particularly well-known system uses cells derived from *Nicotina tabacum* cultured as a callus. To transform plant cells, expression vectors such as pMON530 are introduced into bacteria such as *Agrobacterium tumefaciens*. By infecting tobacco (e.g. *Nicotina tabacum*) with these bacteria, desired polypeptides can be obtained from the tobacco leaves.

Cells from insects such as silkworms (*Bombyx mori*), mosquitoes (e.g. *Aede aegypti, Aedes albopictus*) and fruit flies (*Drosophila melanogaster*) can be used as hosts. For example, when using silkworms as hosts, DNAs encoding antibodies may be inserted into baculovirus vectors and such, these vectors may be used to infect silkworms, and desired polypeptides can be obtained from silkworm body fluids (Nature 315: 592-594 (1985)).

Examples of expression vectors when using animal cells as hosts comprise pME18S (Med. Immunol. 20: 27-32 (1990)), pEF-BOS (Nucleic Acids Res. 18: 5322 (1990)), pCDM8 (Nature 329: 840-842 (1987)), pRSVneo, pSV2-neo, pcD-NAI/Amp (Invitrogen), pcDNAI, pAMoERC3Sc, pCDM8 (Nature 329: 840 (1987)), pAGE107 (Cytotechnology 3: 133 (1990)), pREP4 (Invitrogen), pAGE103 (J. Biochem. 101: 1307 (1987)), pAMoA, pAS3-3, pCAGGS (Gene 108: 193-200 (1991)), pBK-CMV, pcDNA3.1 (Invitrogen), and pZeoSV (Stratagene).

Promoters may be cytomegalovirus IE gene promoter and enhancer, SV40 early promoter, retrovirus LTRs such as those from RSV, HIV, and MMLV, and gene promoters from animal cells such as metallothionein, β-actin, elongation factor-1, HSP genes, and such. Alternatively, viral vectors such as those mentioned above may also be used. Viral vectors may be derived from DNA viruses and RNA viruses such as retroviruses, adenoviruses, adeno-associated viruses, herpes viruses, vaccinia viruses, poxviruses, Sindbis viruses, Sendai viruses, SV40, and HIV.

Host cells among animal cells may be mouse myeloma cells (e.g. SP2/0, NSO), rat myeloma cells (e.g. YB2/0), mouse hybridoma cells, Namalwa cells (including KJM-1 cells and such), human embryonic kidney cells (e.g. 293 cells), human leukemia cells (e.g. BALL-1), CHO cells, COS cells (e.g. COS-1, COS-7), hamster embryonic kidney cells (e.g. BHK), mouse Sertoli cells (e.g. TM4), African green monkey kidney cells (e.g. VERO-76), HBT637 cells, HeLa cells, rabbit kidney cells (e.g. MDCK), human liver cells (e.g. HepG2), mouse mammary tumor cells (e.g. MMT060562 cells), TR1 cells, MRC cells, FS3 cells, etc.

Methods for introducing expression vectors depend on the type of host cell and vector, but any method can be used as long as it allows introduction of antibody-encoding DNA into cells. Vectors can be introduced into prokaryotic cells by methods utilizing calcium ions (Proc. Natl. Acad. Sci, USA 69: 2110 (1972)), protoplasts (Japanese Patent Application No. (JP-A) S63-24829 (unexamined, published Japanese patent application)), electroporation (Gene 17: 107 (1982); Molecular & General Genetics 168: 111 (1979)), and such. Vectors can be introduced into yeast cells by electroporation (Methods in Enzymology, 194: 182 (1990)), spheroplasts (Proc. Natl. Acad. Sci. USA 81: 4889 (1984)), lithium acetate (J. Bacteriol. 153: 163 (1983))), and such. Vectors can be introduced into plant cells by using *Agrobacterium* (Gene 23: 315 (1983); WO 89/05859), sonication (WO 91/00358), and such. Vectors can be introduced into animal cells by using electroporation (Cytotechnology 3: 133 (1990)), calcium phosphate (JP-A H02-227075), lipofection (Proc. Natl, Acad, Sci. USA 84: 7413 (1987); Virology 52: 456 (1973)), co-precipitation with calcium phosphate, DEAE-dextran, direct injection of DNA using microcapillaries, and such.

Transformants obtained as described above can be cultured, for example, by the following methods:

Culture media for transformants of prokaryotes and eukaryotic microorganisms can be natural or synthetic, as long as the media allows efficient culture of the transformants, and comprises nutrients utilizable by the organisms and essential for their growth, such as carbon and nitrogen sources, and inorganic salts. Culture may be carried out under aerobic or anaerobic conditions, and other conditions such as temperature, pH of the medium and duration of the culture can be determined appropriately by one skilled in the art, depending on the type of transformant. When using expression vectors equipped with inducible promoters, inducers may be added to the medium as necessary. For example, expression of vectors comprising the lac promoter can be induced by adding IPTG; and expression of vectors comprising the trp promoter can be induced by adding IAA as an inducer.

When using insect cells as host cells, a medium such as the TNM-FH medium (Pharmingen), Sf-900 II SFM (Life Technologies), ExCell400 and ExCell405 (JRH Biosciences), and Grace's Insect Medium (Nature 195: 788 (1962)) can be used. If necessary, antibiotics such as gentamicin may be added to the medium.

For animal cell transformants, common media such as RPMI1640 (The Journal of American Medical Association 199: 519 (1967)), Eagle's MEM (Science 122: 501 (1952)), DMEM (Virology 8: 396 (1959)), and 199 medium (Proceeding of the Society for the Biological Medicine 73: 1 (1950)), or such media added with BSA and the like, can be used. Culture can be carried out under normal conditions such as pH 6 to 8, 30° C. to 40° C., and 5% $CO_2$. If necessary, antibiotics such as kanamycin and penicillin may be added to the medium.

The antibodies of the present invention obtained as above can be isolated from within host cells, or from the culture medium if secreted into the extracellular space using signal sequences. They can then be purified as substantially pure polypeptides. The antibodies of the present invention can be separated or purified by appropriately selecting, or combining as necessary, methods generally used in separation and purification. Such methods can be chromatography, filtration, ultrafiltration, salting out, solvent precipitation, solvent extraction, distillation, immunoprecipitation, SDS-polyacrylamide gel electrophoresis, isoelectric focusing electrophoresis, dialysis, and recrystallization. Chromatography comprises affinity chromatography, ion exchange chromatography, hydrophobic chromatography, gel filtration, reverse phase chromatography, absorption chromatography, and the like (Strategies for Protein Purification and Characterization: A Laboratory Course Manual, Daniel R. Marshak et al. eds., Cold Spring Harbor Laboratory Press (1996); Antibodies: A Laboratory Course Manual, Harlow and David Lane eds., Cold Spring Harbor Laboratory Press (1988)). Such chromatographies may be performed using liquid chromatographies such as HPLC, FPLC, and the like. In addition, the antibodies of the present invention may be purified by making use of their affinities towards antigens.

Furthermore, the antibodies obtained by the methods of the present invention may be partial fragments of antibodies or modified antibodies. For example, the antibody fragments may be expressed from nucleic acids encoding Fab, F(ab')2, Fv, single chain Fv (scFv), in which Fv from H or L chains are ligated by an appropriate linker and such via the aforementioned expression vectors and hosts (see, for example, Co, M. S. et al., J. Immunol. (1994) 152, 2968-2976; Better, M. & Horwitz, A. H. Methods in Enzymology (1989) 178, 476-496, Academic Press, Inc.; Plueckthun, A. & Skerra, A. Methods in Enzymology (1989) 178, 476-496, Academic Press, Inc.; Lamoyi, E., Methods in Enzymology (1989) 121, 663-669; and Bird, R. E. et al., TIBTECH (1991) 9, 132-137). Moreover, the antibody fragments can be obtained by expressing full-length antibodies, then treating the antibodies with enzymes such as papain and pepsin to produce antibody fragments.

Antibodies bound to various types of molecules, such as polyethylene glycol (PEG), may be used as modified antibodies. Furthermore, antibodies may bind to radioisotopes, chemotherapeutics, cytotoxic substances such as bacteria-derived toxin, and labeling substances. Such modified antibodies can be obtained by chemically modifying the resulting antibodies. Methods for modifying antibodies are already established in the art. The term "antibody" in the present invention also encompasses the modified antibodies as described above.

Furthermore, the antibodies of the present invention may be bispecific antibodies. The bispecific antibodies may have antigen-binding sites recognizing different epitopes on the antigen molecules, or may have one antigen-binding site recognizing antigens and the other recognizing a cytotoxic substance such as a radioactive substance, chemotherapeutic agent, and cell-derived toxin. In this case, it is possible to inhibit the growth of cancer cells by directly applying the cytotoxic substance to the cells expressing antigens to specifically damage them. Bispecific antibodies can be prepared by linking HL pairs of two kinds of antibodies, or obtained by fusing hybridomas that produce different monoclonal antibodies to prepare fused cells generating bispecific antibodies. Furthermore, bispecific antibodies can be generated by using genetic engineering techniques.

Techniques common to the field of genetic engineering can be used to carry out procedures for constructing an expression system for producing the antibodies of the present invention, and for constructing recombinant vectors appropriate for the hosts (see for example, Sambrook et al., Molecular Cloning, Cold Spring Harbor Laboratories (1989)). Host cells may be prokaryotic cells such as bacteria, and eukaryotic cells such as yeast, animal cells, insect cells, and plant cells, as long as the cells are capable of expressing the light chains of the present invention or the antibodies comprising the light chains. Mammalian cells are particularly preferred in view of glycosylation.

Whether or not the antibodies produced as described above are the desired antibodies can be confirmed using as an index the binding activity to abnormal cells in a lesion, or to their surface molecules. Specifically, antibodies obtained by the aforementioned methods are contacted with cancer cells and whether or not the aforementioned cancer cells and antibodies bind is analyzed. Herein, the antibodies that bind to the cancer cells are confirmed to be the desired antibodies in the present invention.

In the above description, there are no particular limitations on the method for detecting the binding between the antibodies and cancer cells, and any method can be used. For example, an immobilized cancer specimen is reacted with a test antibody, and then with a labeled antibody which recognizes the test antibody. The binding of the test antibody to cancer cells can be confirmed by detecting the labeled antibody on the immobilized specimen after washing. Enzymatically active proteins such as peroxidase and β-galactosidase, and fluorescent substances such as FITC can be used as the label. Moreover, flow cytometry is also a preferable method for detecting the aforementioned binding. Alternatively, the binding of the antibody to cancer cells can be detected without any labeling by using a method that uses surface plasmon resonance (SPR), for example the commercially available BIACORE system. Cancer tissues to be analyzed for antibody-binding activity may be cancer tissues forming the lesion from which plasma cells (B cells) are obtained. Alternatively, cancer tissues of the same organ which have been removed from different individuals and cell lines derived from cancers can be also used. Furthermore, cancer tissues derived from different organs, cell lines derived from cancers, cancer cell lines equipped with specific surface antigens, or such can also be used to screen for antibodies which specifically or commonly react with different types of cancers.

In the above description, an antibody whose reactivity towards a cancer tissue is significantly high compared to the normal tissue is said to bind specifically to the cancer. For comparing the reactivities of the antibodies of the present invention, the same type of tissue is generally used. That is, the reactivity of an antibody is compared between a cancer tissue and a normal tissue of the organ from which the cancer tissue is derived. Under conditions in which an antibody's reactivity towards a cancer tissue can be confirmed, the antibody is said to have a specific reactivity towards the cancer tissue when no binding activity towards the normal tissue can be detected.

Methods of screening for antibodies using binding activity as an index include the panning method which utilizes phage vectors. When the obtained antibody genes are gene libraries of heavy and light chain subclasses as described above, screening methods that use phage vectors are advantageous. As described in the Examples, genes encoding variable regions of the heavy and light chains can be made into single chain Fv (scFv) through conjugation with a suitable linker sequence. Libraries expressing scFv on phage surfaces can be obtained by inserting a scFv-encoding gene into a phage vector. By contacting these phages with an antigen of interest and recovering the phages bound to the antigen from the library, DNAs encoding scFv with the desired binding activity can be recovered. scFv having the desired binding activity can also be concentrated by repeating this procedure as necessary. For example, Barabas, III, C. F. et al., "Phage Display—A Laboratory Manual", Cold Spring Harbor Laboratory Press, 2001, can be referred to regarding the preparation of phage libraries. Moreover, commercially available systems for constructing phage libraries can be used for preparing phage libraries, and preparation can be carried out by using, for example, pCANTAB phagemid vector or M13K07 helper vector as in the Examples.

The aforementioned antibodies of the present invention are useful for the diagnosis and treatment of lesion tissues. When using antibodies of the present invention for diagnosis, the antibodies can be used as antibody molecules labeled with a traceable label such as an enzyme label, a radioactive label, or a fluorescent label. The presence of cancer may be detected from the location of the antibodies after administering the antibodies modified with such a label to subjects. Moreover, the antibodies of the present invention can also be immobilized onto a solid phase such as a plate or beads to form a diagnostic kit and the like. Furthermore, the case of using the antibodies of the present invention for treatments is described later.

As a fifth aspect, the present invention provides a method for producing therapeutic compositions against lesion tissues. Since plasma cells that proliferate and are activated in the highly immunodeficient animals by the aforementioned methods of the present invention produce antibodies to abnormal substances within lesion tissues, these cells can be used as a therapeutic composition against the lesion tissues. Consequently, the aforementioned method of the present invention for producing plasma cells can also be applied as a method for producing therapeutic compositions against lesion tissues. Namely, the method of the present invention for producing therapeutic compositions against lesion tissues comprises the steps of: (a) transplanting a lesion tissue infiltrated with lymphocytes to a highly immunodeficient non-human animal; (b) detecting lymphocyte proliferation at the site of transplantation; and (c) recovering cells comprising lymphocytes from the site of transplantation.

The "lesion tissues infiltrated with lymphocytes" in the production of therapeutic compositions are the same as in the aforementioned methods for proliferating and producing plasma cells, and are cells and tissues having substances that may be recognized as foreign matter by the body's immune system or having degeneration products of organisms or biological substances, such as neoplasms. Examples of such include tissues forming a cancer or hyperplasia and cells infected with viruses. These cells and tissues are not limited to those collected from patients that are subjects of treatment, and cells and tissues collected from other patients or other animals may also be used.

Cells and tissues infiltrated with lymphocytes are transplanted into highly immunodeficient animals in the same manner as in the aforementioned method for proliferating or producing plasma cells, and are recovered after proliferation of lymphocytes has been detected. Herein, the recovered transplanted cells in which lymphocytes have proliferated may be directly used as a therapeutic composition, or may be used as a therapeutic composition after having selected and separated the antibody-producing plasma cells, lymphocytes and the like by microdissection and such. Moreover, plasma cells and the like may be selected and separated from blood collected from highly immunodeficient animals transplanted with cells and the like infiltrated with lymphocytes, and used as a therapeutic composition.

The recovered transplanted cells or separated lymphocytes and the like can be further cultured and proliferated in vitro.

Moreover, instead of using lymphocytes such as plasma cells activated using highly immunodeficient animals, therapeutic compositions for lesion tissues arising as a result of cancer or viral infection may also be produced by using antibodies produced from plasma cells or antibody-encoding nucleic acids. The antibodies or antibody-encoding nucleic acids used herein can be those produced by the aforementioned methods of the present invention for producing antibodies and for producing nucleic acids encoding antibodies. When antibodies are used for therapeutic compositions, in addition to the antibodies' direct attack against abnormal substances such as cancer cells, virus-infected cells, and such, antibodies may also be used as a means of transporting anticancer agents and antiviral agents to cancer cells, virus-infected cells, and the like by binding anticancer agents or antiviral agents to the antibodies. Moreover, nucleic acids encoding antibodies may be similarly used; i.e. they may be administered to human patients either as is or with the support of an expression vector, and make the antibodies expressed in the body attack the abnormal substances in lesion tissues. Alternatively, the antibody-encoding nucleic acids of the present invention may also be fused with nucleic acids encoding another polypeptide having an anticancer or antiviral effect and used for transporting polypeptides having an anticancer or antiviral effect to abnormal cells.

All prior art references cited herein are incorporated by reference into this description.

EXAMPLES

Herein below, the present invention will be specifically described using Examples, but it is not to be construed as being limited thereto.

Example 1

Accumulation of Specific Plasma Cells and Increase of Antibody Titer in NOG Mice Tumor tissues removed with consent from cancer patients during surgery were subcutaneously transplanted into NOG mice with the purpose of establishing cancer cell lines using NOG mice, Transplantation was carried out in the same manner using SCID mice as a control. Specifically, human breast cancer tissues were sliced into thin sections, and equal amounts were subcutaneously transplanted into NOG mice and SCID mice.

Transplantation was carried out with the supposition that transplantation efficiency would be higher in NOG mice as compared to nude mice, which have B cells and NK cells, and SCID mice, which have NK cells (Nature 301: 527-530, 1983); however, contrary to expectations, the transplantation efficiency was low (data not shown).

To find out the reasons for the above, cancer tissues were transplanted into NOG mice and SCID mice as described above and mice were dissected nine weeks later to recover the transplants. The transplants were embedded in OCT compound, and frozen blocks were prepared and stored in a deep freezer. A portion of the transplants were fixed in PFA, embedded in paraffin using the Amex method, sliced into thin sections, stained with HE, and pathological observations were carried out.

Figure 1:
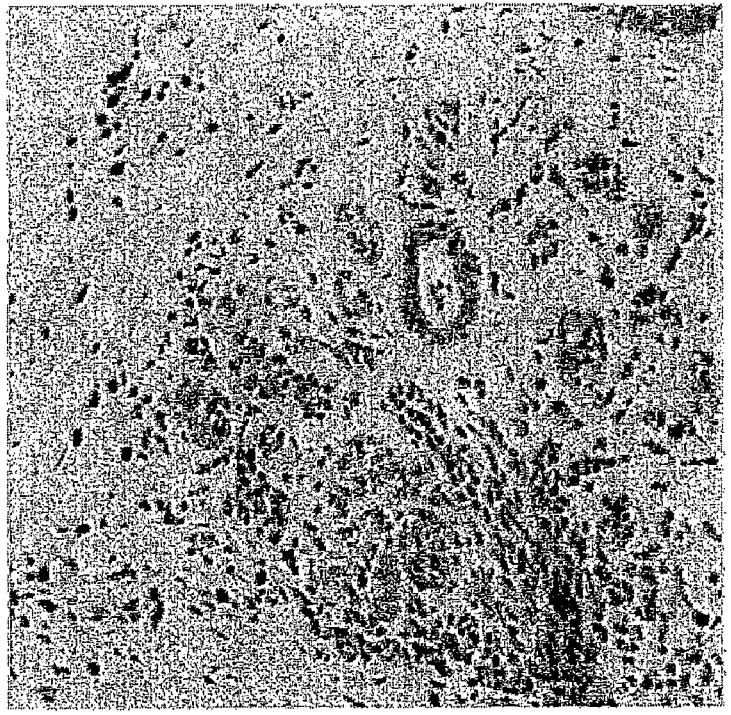
FIG. 1 shows photographs of HE-stained paraffin sections prepared after thinly slicing human breast cancer tissues. Equal amounts of human breast cancer tissues were transplanted into NOG mice and SCID mice, and the mice were dissected nine weeks later. A high degree of accumulation of plasma cells is observed in NOG mice. Moreover, an image of leukocytes infiltrating tumor cells is observed, suggesting that the immune system is actively functioning. These tissue images strongly suggested the presence of a cancer-specific immune response.
Figure 1:
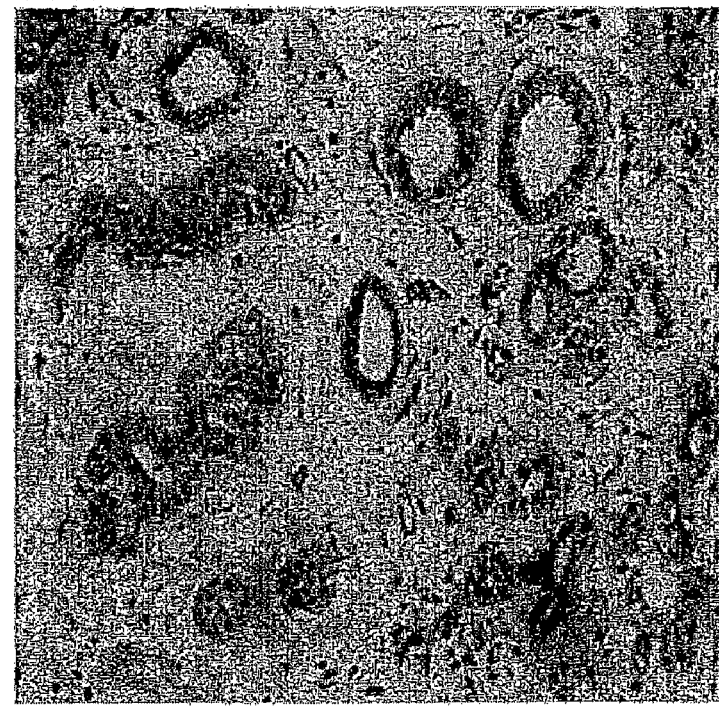

As a result, surprising findings were obtained. Namely, pathological images of a significantly high accumulation of plasma cells in the cancer tissues of NOG mice were observed during histopathological analyses, as compared to SCID mice, suggesting that the antibodies produced by the plasma cells may be attacking the cancer tissues (FIG. 1). A comparison with pathological images prior to transplantation confirmed that an even higher condensation of plasma cells was occurring in NOG mice (data not shown).

Cancer cells employ various strategies to escape from the host's immune system. The most common method is to reduce the expressed HLA antigen to prevent cancer antigens from being presented to immunocompetent cells (Moller et al, (1992) Cancer Surv 13:101). Moreover, TGF-β secreted by cancer cells has been reported to compete with IL-12 and prevents the activation of tumor immunity (Mouri (2002) Acta Med Okayama 56:309). In addition, the body's immune responses are suppressed by secretion of indoleamine 2,3-dioxygenase and Fas ligand (Zheng et al. (2003) Gast Cancer 9:1415; Reference 34/Uyttenhove et al. Nat Med 9: 1269). The present inventors conceived the possibility that lymphocyte activation occurs due to attenuation of the mechanism which suppresses the immune system in tumor tissues transplanted into highly immunodeficient non-human animals. Although tumor immunity comprises the cellular immune system mediated by cytotoxic T cells and NK cells, and the humoral immune system centered around antibodies, pathological observations revealed that the humoral immune system was particularly activated in transplanted tumor tissues.

Figure 2:
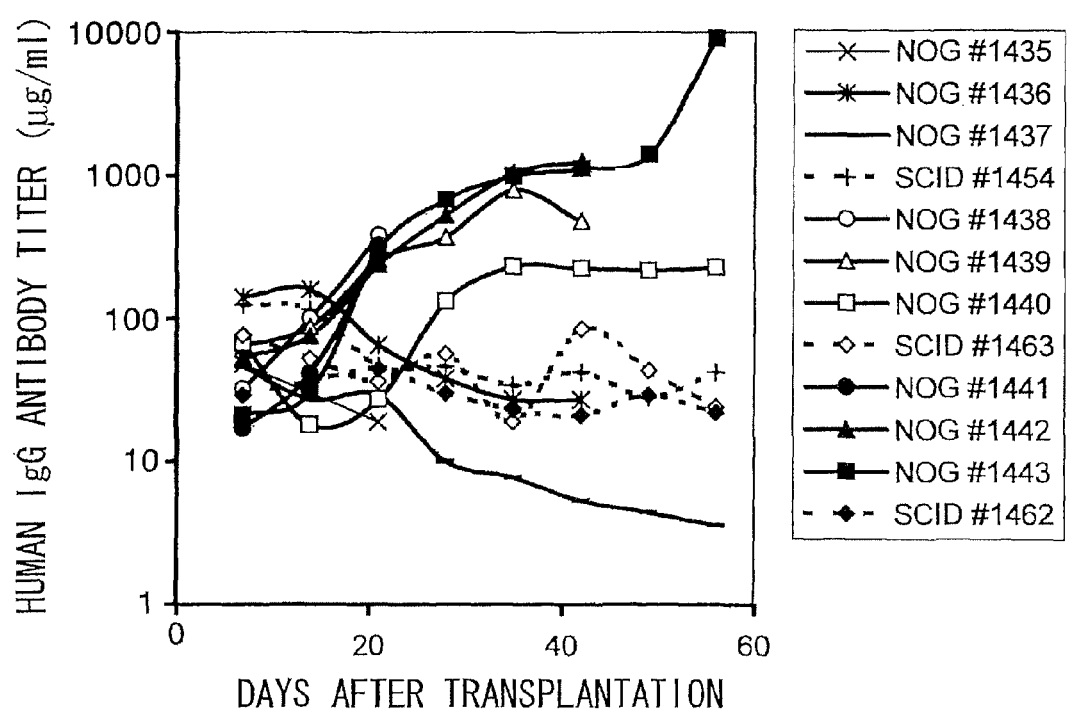
FIG. 2 is a graph showing the results of transplanting human breast cancer tissues into NOG mice and SCID mice and monitoring the changes in human IgG antibody titer. IgG antibody titers in NOG mice showed values that were ten to hundred times higher than those in SCID mice.

Next, the titer of human-derived antibodies comprised in the serum of NOG mice was measured. Specifically, human breast cancer tissues were transplanted into NOG mice and the control SCID mice, blood was subsequently collected weekly from the orbital cavities of each mouse, sera were separated, and the antibody titers were monitored. As a result, IgG antibody titers in NOG mice showed values ten to a hundred times higher than in SCID mice. The highest values among NOG mice were confirmed to show an antibody titer of 10 mg/ml (FIG. 2).

The relationship between the degree of accumulation of plasma cells in transplants and the titer of human antibodies in the serum of NOG mice was investigated. The degree of accumulation of plasma cells was evaluated based on pathological observations and was classified according to the following criteria:

Grade 1: Small numbers of plasma cells are observed throughout the tissue fragment.
Grade 2: Several accumulation foci of plasma cells are observed throughout the tissue fragment.
Grade 3: Accumulation foci of plasma cells are observed across multiple fields.

Figure 5:
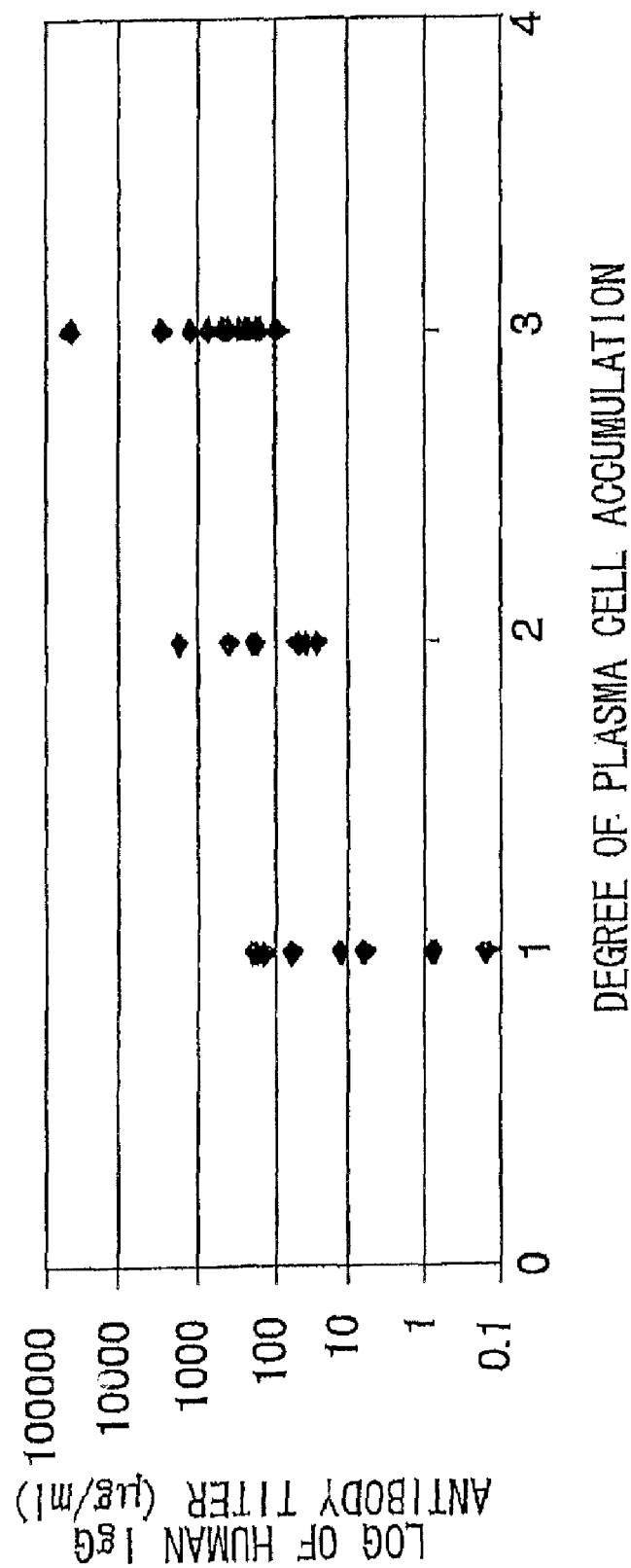
FIG. 5 is a graph showing the degree of accumulation of plasma cells versus the concentration of human IgG in the serum of NOG mice. There was a good correlation between the degree of accumulation (density) and the antibody titer.

As was previously described, antibody titers were measured by collecting blood from the orbital cavities of mice, followed by separation of the serum. As a result, a high correlation was observed between the degree of accumulation of plasma cells in transplants and the antibody titer of human antibodies in the serum of NOG mice (FIG. 5).

Figure 6:
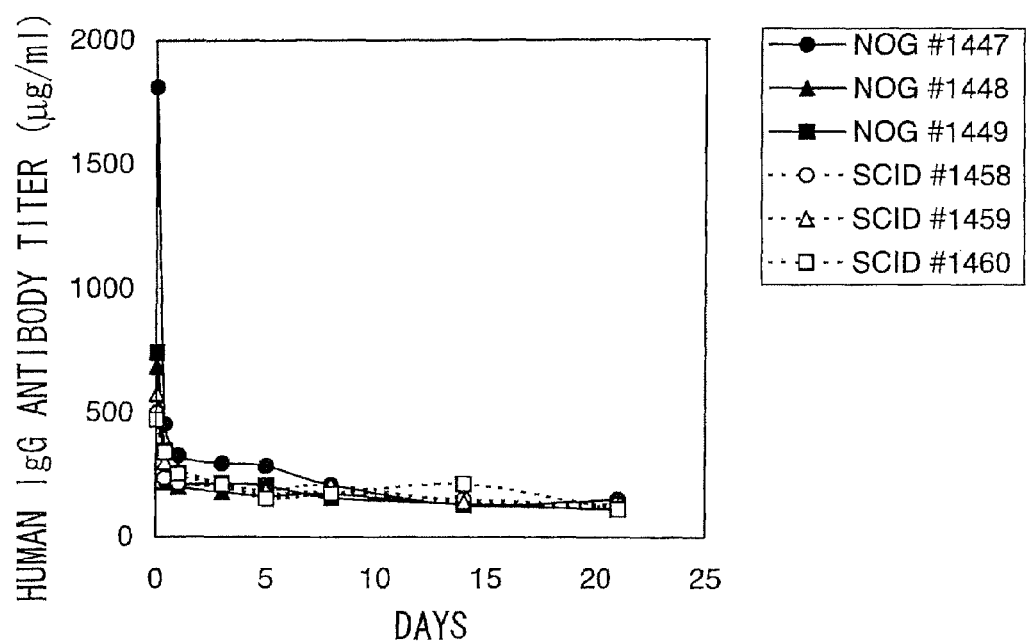
FIG. 6 is a graph showing the half-life of human IgG after administration to NOG mice and SCID mice. The half-life in NOG mice was about 18 days, while that in SCID mice was 21 days. The half-life in NOG mice was slightly shorter. This indicated that the high titer of human antibodies in NOG mice was not caused by a delay in clearance.

Whether the high antibody titer in NOG mice was due to the effects of clearance in NOG mice was investigated. Human IgGs were administered to NOG mice and SCID mice to investigate their half-life. The half-life in NOG mice was about 18 days, while that in SCID mice was 21 days, with the half-life in NOG mice being slightly shorter (FIG. 6). Based on this finding, the high human antibody titers in NOG mice were shown not to be caused by a delay in clearance.

Example 2

Figure 4:
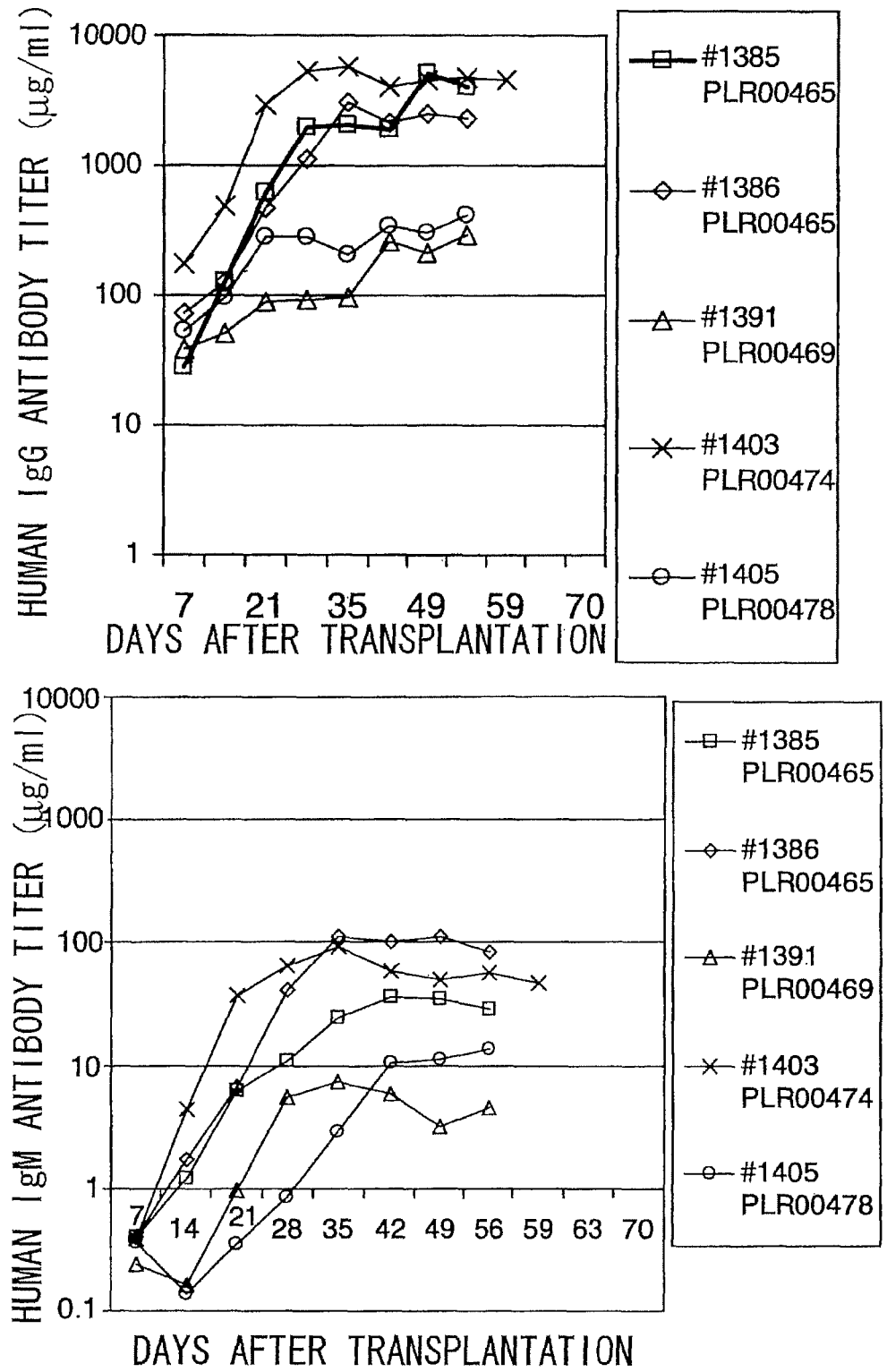
FIG. 4 shows the results of transplanting human breast cancer specimens into NOG mice and monitoring the changes in human IgG and IgM antibody titers. An increase in antibody titer was observed in four specimens shown in the figure among the ten specimens. RNAs were extracted from four of these cases and the antibody gene was amplified.

Concentration and Separation of Plasma Cells in Breast Cancer Transplants and Amplification and Sequencing of the Antibody Genes Fresh human breast cancer tissues were cut into suitable sizes and transplanted subcutaneously into NOG mice and SCID mice using a trocar. Following transplantation, blood was collected weekly from the orbital cavities of NOG mice, sera were separated, and the antibody titers were monitored. The antibody titers began to increase immediately after transplantation, reached a maximum value on week 5 following transplantation, and tended to decrease slowly thereafter (FIG. 4).

Mice (#1385, #1386, #1403, #1405) were dissected after the antibody titers were confirmed to have reached a maximum. Following dissection, the transplants were embedded in OCT compound, frozen blocks were prepared, and stored in a deep freezer. A portion of the transplants were fixed in PFA, embedded in paraffin using the Amex method, sliced into thin sections, stained with HE, and pathological observations were carried out. The frozen sections embedded in the OCT compound were thinly sliced and immediately subjected to RNA extraction, or sliced into thin sections and subjected to RNA extraction after excising plasma cells by LMD.

In the aforementioned procedures, total RNAs extracted directly from the thin sections and RNAs extracted after excising plasma cells by LMD were both purified using the RNeasy Mini Kit (QIAGEN). Based on these purified total RNAs, cDNAs were synthesized using Sensiscript Reverse Transcriptase (QIAGEN) according to the manufacturer's instructions. PCR amplifications were performed using these cDNAs as template and primers for cloning human antibody variable regions. Primers were designed based on the research paper "J. Mol. Biol. (1991) 222, 581-597", and the web site of the Medical Research Council (MRC), "V BASE" (mrc-cpe.cam.ac.uk/vbase-ok.php?mene=901). Primer names starting with VH and JH correspond to primers for cloning heavy chain variable regions. Primer names starting with VK and JK, or VL and JL correspond to primers for amplifying the light chain κ chain or the light chain λ chain.

```
VH1a
                                        (SEQ ID NO: 1)
5'-CAGGT(GT)CAGCTGGTGCAGTCTGG-3'

VH1b
                                        (SEQ ID NO: 2)
5'-CAGGTCCAGCTTGTGCAGTCTGG-3'
```

-continued

VH1c
(SEQ ID NO: 3)
5'-(GC)AGGTCCAGCTGGTACAGTCTGG-3'

VH1d
(SEQ ID NO: 4)
5'-CA(AG)ATGCAGCTGGTGCAGTCTGG-3'

VH2a
(SEQ ID NO: 5)
5'-CAGATCACCTTGAAGGAGTCTGGT-3'

VH2b
(SEQ ID NO: 6)
5'-CAGGTCACCTTGA(AG)GGAGTCTGGT-3'

VH3a
(SEQ ID NO: 7)
5'-GA(AG)GTGCAGCTGGTGGAGTCTGG-3'

VH3b
(SEQ ID NO: 8)
5'-CAGGTGCAGCTGGTGGAGTCTGG-3'

VH3c
(SEQ ID NO: 9)
5'-GAGGTGCAGCTGTTGGAGTCTGG-3'

VH4a
(SEQ ID NO: 10)
5'-CAG(CG)TGCAGCTGCAGGAGTCGGGC-3'

VH4b
(SEQ ID NO: 11)
5'-CAGGTGCAGCTACAGCAGTGGGGC-3'

VH5a
(SEQ ID NO: 12)
5'-GA(AG)GTGCAGCTGGTGCAGTCTGGA-3'

VH6a
(SEQ ID NO: 13)
5'-CAGGTACAGCTGCAGCAGTCAGGT-3'

VH7a
(SEQ ID NO: 14)
5'-CAGGT(CG)CAGCTGGTGCAATCTGG-3'

JH1245
(SEQ ID NO: 15)
5'-TGAGGAGACGGTGACCAGGGT(GT)CC-3'

JH3
(SEQ ID NO: 16)
5'-TGAAGAGACGGTGACCATTGTCCC-3'

JH6
(SEQ ID NO: 17)
5'-TGAGGAGACGGTGACCGTGGTCCC-3'

VK1a
(SEQ ID NO: 18)
5'-(AG)ACATCCAGATGACCCAGTCTCCA-3'

VK1b
(SEQ ID NO: 19)
5'-G(AC)CATCCAGTTGACCCAGTCTCCA-3'

VK1c
(SEQ ID NO: 20)
5'-GCCATCC(AG)GATGACCCAGTCTCCA-3'

VK1d
(SEQ ID NO: 21)
5'-GTCATCTGGATGACCCAGTCTCCA-3'

VK2a
(SEQ ID NO: 22)
5'-GATATTGTGATGACCCAGACTCCA-3'

VK2b
(SEQ ID NO: 23)
5'-GAT(AG)TTGTGATGACTCAGTCTCCA-3'

VK3a
(SEQ ID NO: 24)
5'-GAAATTGTGTTGAC(AG)CAGTCTCCA-3'

VK3b
(SEQ ID NO: 25)
5'-GAAATAGTGATGACGCAGTCTCCA-3'

VK3c
(SEQ ID NO: 26)
5'-GAAATTGTAATGACACAGTCTCCA-3'

VK4a
(SEQ ID NO: 27)
5'-GACATCGTGATGACCCAGTCTCCA-3'

VK5a
(SEQ ID NO: 28)
5'-GAAACGACACTCACGCAGTCTCCA-3'

VK6a
(SEQ ID NO: 29)
5'-GAAATTGTGCTGACTCAGTCTCCA-3'

VK6b
(SEQ ID NO: 30)
5'-GATGTTGTGATGACACAGTCTCCA-3'

JK1
(SEQ ID NO: 31)
5'-ACGTTTGATTTCCACCTTTGGTCCC-3'

JK24
(SEQ ID NO: 32)
5'-ACGTTTTGATCTCCA(CG)CTTGGTCCC-3'

JK3
(SEQ ID NO: 33)
5'-ACGTTTGATATCCACTTTGGTCCC-3'

JK5
(SEQ ID NO: 34)
5'-ACGTTTAATCTCCAGTCGTGTCCC-3'

VL1a
(SEQ ID NO: 35)
5'-CAGTCTGTGCTGACTCAGCCACCC-3'

VL1b
(SEQ ID NO: 36)
5'-CAGTCTGTG(CT)TGACGCAGCCGCCC-3'

VL2
(SEQ ID NO: 37)
5'-CAGTCTGCCCTGACTCAGCCT(CG)-3'

VL3a
(SEQ ID NO: 38)
5'-TCCTATG(AT)GCTGACTCAGCCACCC-3'

VL3b
(SEQ ID NO: 39)
5'-TCCTATGAGCTGACACAGC(CT)ACCC-3'

VL3c
(SEQ ID NO: 40)
5'-TCTTCTGAGCTGACTCAGGACCCT-3'

VL3d
(SEQ ID NO: 41)
5'-TCCTATGAGCTGATGCAGCCACCC-3'

VL4a
(SEQ ID NO: 42)
5'-CAGCCTGTGCTGACTCAATCATCC-3'

-continued

VL4b
(SEQ ID NO: 43)
5'-CAGCTTGTGCTGACTCAATCGCCC-3'

VL4c
(SEQ ID NO: 44)
5'-CTGCCTGTGCTGACTCAGCCCCCG-3'

VL5a
(SEQ ID NO: 45)
5'-CAGCCTGTGCTGACTCAGCCA(CT)CT-3'

VL5c
(SEQ ID NO: 46)
5'-CAGGCTGTGCTGACTCAGCCGGCT-3'

VL6
(SEQ ID NO: 47)
5'-AATTTTATGCTGACTCAGCCCCAC-3'

VL7
(SEQ ID NO: 48)
5'-CAG(AG)CTGTGGTGACTCAGGAGCCC-3'

VL8
(SEQ ID NO: 49)
5'-CAGACTGTGGTGACCCAGGAGCCA-3'

VL4_9
(SEQ ID NO: 50)
5'-C(AT)GCCTGTGCTGACTCAGCCACCT-3'

VL10
(SEQ ID NO: 51)
5'-CAGGCAGGGCTGACTCAGCCACCC-3'

JL1
(SEQ ID NO: 52)
5'-ACCTAGGACGGTGACCTTGGTCCC-3'

JL23
(SEQ ID NO: 53)
5'-ACCTAGGACGGTCAGCTTGGTCCC-3'

JL7
(SEQ ID NO: 54)
5'-ACCGAGGACGGTCAGCTGGGTGCC-3'

IgGrev
(SEQ ID NO: 55)
5'-CGTCACCGGTTCGGGGAAGTAGTC-3'

IgMrev
(SEQ ID NO: 56)
5'-GGGGAATTCTCACAGGAGACGAG-3'

IgKrev
(SEQ ID NO: 57)
5'-GGCAGTTCCAGATTTCAACTGCT-3'

For cloning the heavy chain variable regions, κ chain variable regions, and λ chain variable regions, PCR amplifications were carried out using combinations of the Taq DNA polymerase Core Kit (QIAGEN) and primer mixtures for each gene subset. For amplifying the γ chain, μ chain, κ chain, and λ chain, five different primer mixtures were prepared for each. A total of 20 kinds of reaction solutions were prepared using these primer mixtures. Combinations of primers in the mixtures are shown in Table 1. Prepared reaction mixtures (20 μl) comprising 4 μl of the template cDNA had a final concentration of 1× reaction buffer, 1×Q solution (QIAGEN), 0.4 mM dNTP, 0.4 μM each of the forward and reverse primers, and 2 U Taq DNA polymerase. The reaction mixtures were subjected to 40 cycles of amplification reaction on Applied Biosystems PE9700. The amplification cycle was carried out under conditions of denaturation at 94° C. for 10 sec, annealing at 50° C. for 30 sec, and elongation at 72° C. for 30 sec.

TABLE 1

| PRIMER SETS | FORWARD | REVERSE |
|---|---|---|
| VH1-IgGrev MIX | VH1a VH1b VH1c VH1d | IgGrev |
| VH2-IgGrev MIX | VH2a VH2b | IgGrev |
| VH3/5-IgGrev MIX | VH3a VH3b VH3c VH3d | IgGrev |
| VH4-IgGrev MIX | VH4a VH4b | IgGrev |
| VH6/7-IgGrev MIX | VH6a VH7a | IgGrev |
| VH1-IgMrev MIX | VH1a VH1b VH1c VH1d | IgMrev |
| VH2-IgMrev MIX | VH2a VH2b | IgMrev |
| VH3/5-IgMrev MIX | VH3a VH3b VH3c VH3d | IgMrev |
| VH4-IgMrev MIX | VH4a VH4b | IgMrev |
| VH6/7-IgMrev MIX | VH6a VH7a | IgMrev |
| VK1-IgKrev MIX | VK1a VK1b VK1c VK1d | IgKrev |
| VK2-IgKrev MIX | VK2a VK2b | IgKrev |
| VK3-IgKrev MIX | VK3a VK3b VK3c | IgKrev |
| VK4/5-IgKrev MIX | VK4a VK5a | IgKrev |
| VK6-Igrev MIX | VK6a VK6b | IgKrev |
| VL1/2-JL MIX | VL1a VL1b VL2 | JL1 JL23 JL7 |
| VL3-JL MIX | VL3a VL3b VL3c VL3d | JL1 JL23 JL7 |
| VL4-JL MIX | VL4a VL4b VL4c | JL1 JL23 JL7 |
| VL5/6-JL MIX | VL5a VL5c VL6 | JL1 JL23 JL7 |
| VL7_10-JL MIX | VL7 VL8 VL4_9 VL10 | JL1 JL23 JL7 |

Nested PCR amplification reactions were further carried out on the amplification products of the heavy chain variable regions (γ chain and μ chain) and the κ chain variable region. The combinations of primers used are shown in Table 2.

TABLE 2

| PRIMER SETS | FORWARD | REVERSE |
|---|---|---|
| VH1-JH MIX | VH1a VH1b VH1c VH1d | JH1245 JH3 JH6 |
| VH2-JH MIX | VH2a VH2b | JH1245 JH3 JH6 |
| VH3/5-JH MIX | VH3a VH3b VH3c VH3d | JH1245 JH3 JH6 |
| VH4-JH MIX | VH4a VH4b | JH1245 JH3 JH6 |
| VH6/7-JH MIX | VH6a VH7a | JH1245 JH3 JH6 |
| VK1-JK MIX | VK1a VK1b VK1c VK1d | JK1 JK24 JK3 JK5 |
| VK2-JK MIX | VK2a VK2b | JK1 JK24 JK3 JK5 |
| VK3-JK MIX | VK3a VK3b VK3c | JK1 JK24 JK3 JK5 |
| VK4/5-JK MIX | VK4a VK5a | JK1 JK24 JK3 JK5 |
| VK6-JK MIX | VK6a VK6b | JK1 JK24 JK3 JK5 |

Example 3

Concentration and Separation of Plasma Cells in Prostate Cancer Transplants, Amplification and Sequencing of the Antibody Genes, and Production of ScFv Based on the method indicated in Example 2, the variable regions of antibody genes produced by plasma cells, whose proliferation and accumulation were observed when prostate cancer or prostatic hyperplasia tissues were transplanted, were amplified by PCR. The primers and conditions used for PCR are the same as in Example 2.

A DNA fragment of antibody heavy chain variable region amplified by PCR was inserted into a pGEM-T Easy vector (Promega), and this was used to transform *Escherichia coli* DH5α. The nucleotide sequences of the insert sequence of the resulting transformed plasmids were determined. The determined nucleotide sequences are shown in SEQ ID NO: 58, 60, 62, 64, and 66. The translated amino acid sequences of these nucleotide sequences are respectively shown in SEQ ID NO: 59, 61, 63, 65, and 67. Among the 16 analyzed clones, eight sequences had a functional open reading frame, and of these, there were five independent sequences. Of the 16 clones, the sequences shown in SEQ ID NO: 64 and SEQ ID NO: 66 were found at a frequency of three and two times, respectively. The low level of sequence variety suggests that some form of selection pressure occurred causing clonal proliferation of plasma cells producing specific antibodies.

The linker sequences to be used for preparing single-stranded antibody genes were produced according to the method of Marks et al. (J. Mol. Biol. (1991) 222, 581-597). The template DNA sequences and the nucleotide sequences of primers used are shown below. Linker fragments synthesized using PCR amplification were confirmed by agarose gel electrophoresis, then excised and purified.

Template DNA Sequence (Template Linker)

(SEQ ID NO: 68)
5'-GGACAATGGTCACCGTCTCTTCAGGTGGTGGTGGTTCGGGTGGTGGT

GGTTCGGGTGGTGGCGGATCGGACATCCAGATGACCCAGTCTCC-3'

Nucleotide Sequences of Primers:
Reverse JH for Linker

1 LJH1_2
(SEQ ID NO: 69)
5'-GCACCCTGGTCACCGTCTCCTCAGGTGG-3'

2 LJH3
(SEQ ID NO: 70)
5'-GGACAATGGTCACCGTCTCTTCAGGTGG-3'

3 LJH4_5
(SEQ ID NO: 71)
5'-GAACCCTGGTCACCGTCTCCTCAGGTGG-3'

4 LJH6
(SEQ ID NO: 72)
5'-GGACCACGGTCACCGTCTCCTCAGGTGG-3'

Reverse VK for Linker

5 LVK1
(SEQ ID NO: 73)
5'-GGAGACTGGGTCATCTGGATGTCCGATCCGCC-3'

6 LVK2
(SEQ ID NO: 74)
5'-GGAGACTGAGTCATCACAACATCCGATCCGCC-3'

7 LVK3
(SEQ ID NO: 75)
5'-GGAGACTGCGTCAACACAATTTCCGATCCGCC-3'

8 LVK4
(SEQ ID NO: 76)
5'-GGAGACTGGGTCATCACGATGTCCGATCCGCC-3'

9 LVK5
(SEQ ID NO: 77)
5'-GGAGACTGCGTGAGTGTCGTTTCCGATCCGCC-3'

10 LVK6
(SEQ ID NO: 78)
5'-GGAGACTGAGTCAGCACAATTTCCGATCCGCC-3'

Reverse VL for Linker

11 LVL1
(SEQ ID NO: 79)
5'-GGCGGCTGCGTCAACACAGACTGCGATCCGCCACCGCCAGAG-3'

12 LVL2
(SEQ ID NO: 80)
5'-GCAGGCTGAGTCAGAGCAGACTGCGATCCGCCACCGCCAGAG-3'

13 LVL3a
(SEQ ID NO: 81)
5'-GGTGGCTGAGTCAGCACATAGGACGATCCGCCACCGCCAGAG-3'

14 LVL3b
(SEQ ID NO: 82)
5'-GGGTCCTGAGTCAGCTCAGAAGACGATCCGCCACCGCCAGAG-3'

15 LVL4
(SEQ ID NO: 83)
5'-GGCGGTTGAGTCAGTATAACGTGCGATCCGCCACCGCCAGAG-3'

16 LVL5
(SEQ ID NO: 84)
5'-GACGGCTGAGTCAGCACAGACTGCGATCCGCCACCGCCAGAG-3'

17 LVL6
(SEQ ID NO: 85)
5'-TGGGGCTGAGTCAGCATAAAATTCGATCCGCCACCGCCAGAG-3'

The heavy chain variable region, κ chain variable region, or λ chain variable region and linker sequence amplified by PCR were mixed, and PCR was carried out using the primer sets indicated below, A VH primer and JK primer combination was used to prepare reaction solutions when the light chain was a κ chain, while a VH primer and JL primer combination was used to prepare reaction solutions when the light chain was a λ chain. The reaction solutions were prepared using Ex Taq DNA polymerase (TaKaRa) according to instructions from the manufacturer. Denaturation at 94° C. for 1 minute, then 30 cycles of denaturation at 94° C. for 15 seconds and an elongation reaction at 68° C. for 1 minute were carried out to assemble and amplify a single strand antibody gene library.

VH1BACKSfi
(SEQ ID NO: 86)
5'-GTCCTCGCAACTGCGGCCCAGCCGGCCATGGCCCAGGTGCAGCTGGTGCAGTCTGG-3'

VH2BACKSfi
(SEQ ID NO: 87)
5'-GTCCTCGCAACTGCGGCCCAGCCGGCCATGGCCCAGGTCAACTTAAGGGAGTCTGG-3'

VH3BACKSfi
(SEQ ID NO: 88)
5'-GTCCTCGCAACTGCGGCCCAGCCGGCCATGGCCGAGGTGCAGCTGGTGGAGTCTGG-3'

VH4BACKSfi
(SEQ ID NO: 89)
5'-GTCCTCGCAACTGCGGCCCAGCCGGCCATGGCCCAGGTGCAGCTGCAGGAGTCGGG-3'

VH5BACKSfi
(SEQ ID NO: 90)
5'-GTCCTCGCAACTGCGGCCCAGCCGGCCATGGCCCAGGTGCAGCTGTTGCAGTCTGC-3'

-continued

VH6BACKSfi
(SEQ ID NO: 91)
5'-GTCCTCGCAACTGCGGCCCAGCCGGCCATGGCCCAGGTACAGCTGCAGCAGTCAGG-3'

JK1FORNot
(SEQ ID NO: 92)
5'-GAGTCATTCTCGACTTGCGGCCGCACGTTTGATTTCCACCTTGGTCCC-3'

JK2FORNot
(SEQ ID NO: 93)
5'-GAGTCATTCTCGACTTGCGGCCGCACGTTTGATCTCCAGCTTGGTCCC-3'

JK3FORNot
(SEQ ID NO: 94)
5'-GAGTCATTCTCGACTTGCGGCCGCACGTTTGATATCCACTTTGGTCCC-3'

JK4FORNot
(SEQ ID NO: 95)
5'-GAGTCATTCTCGACTTGCGGCCGCACGTTTGATCTCCACCTTGGTCCC-3'

JK5FORNot
(SEQ ID NO: 96)
5'-GAGTCATTCTCGACTTGCGGCCGCACGTTTAATCTCCAGTCGTGTCCC-3'

JL1FORNot
(SEQ ID NO: 97)
5'-GAGTCATTCTCGACTTGCGGCCGCACCTAGGACGGTGACCTTGGTCCC-3'

JL2_3FORNot
(SEQ ID NO: 98)
5'-GAGTCATTCTCGACTTGCGGCCGCACCTAGGACGGTCAGCTTGGTCCC-3'

JL4_5FORNot
(SEQ ID NO: 99)
5'-GAGTCATTCTCGACTTGCGGCCGCACCTAAAACGGTGAGCTGGGTCCC-3'

After confirming the amplification products by agarose gel electrophoresis, the bands comprising the corresponding gene fragments were excised and purified. The excised fragments were cleaved with the restriction enzymes StiI and NotI and inserted into the phagemid vector pCANTAB5E (Amersham Bioscience). The scFv protein encoded by the fragment inserted into the phagemid is expressed as a fusion protein with the M13 phage gene III and presented on M13 phages during infection with helper phages. Escherichia coli TG1 were transformed with the scFv library phagemids, and the inserted nucleotide sequences of clones randomly selected from the resulting E. coli library were clarified. The nucleotide sequences of the scFv single chain antibodies determined in the present Example are shown in SEQ ID NO: 100, 102, 104, 106, 108, and 110, while the translated amino acid sequences are shown in SEQ ID NO: 101, 103, 105, 107, 109, and 111.

The scFv E. coli library having random combinations of heavy chain variable regions and light chain variable regions was infected with the helper phage M13K07 to produce a phage library presenting scFv proteins on the phages. 0.2 ml of phage precipitation solution (20% polyethylene glycol (average molecular weight: 8000), 2.5 M NaCl) was added to 1 ml of phage solution, mixed well, and incubated on ice for 30 minutes. Phages were subsequently precipitated by centrifugation. This precipitate was suspended in a 2% skim milk-PBS solution and a blocking reaction was carried out at room temperature for one hour.

The phage clones were concentrated and selected using the binding activity toward the cell surface of the DU145 prostate cancer line cells as an index. DU145 cells were cultured at 37° C. and under 5% $CO_2$ in RPMI1640 medium containing 10% fetal bovine serum (FBS). After washing the proliferating adherent DU145 cells with PBS, cells were removed from the dishes using PBS containing 1 mM EDTA. After centrifuging the cell suspension once, the cells were resuspended in 2% FBS/PBS to $2\times10^6$ cells/ml. An equal volume of scFv phage library solution was added to the cell suspension and this was incubated for 2 hours while shaking at 4° C. The mixture was centrifuged with the purpose of separating phages that bound to the cells from those that did not bind, precipitated cells were collected and resuspended in 2% FBS/PBS. After repeating this washing procedure for a total of five times, E. coli TG1 in a logarithmic growth phase were added to the precipitated cells, and phages that bound to the cells were collected. Cloning was carried out by adding TG1 and incubating at 37° C. for 1 hour, then plating the TG1 solution onto a medium containing the drug marker ampicillin, and incubating overnight at 37° C. to let colonies form.

Figure 9:
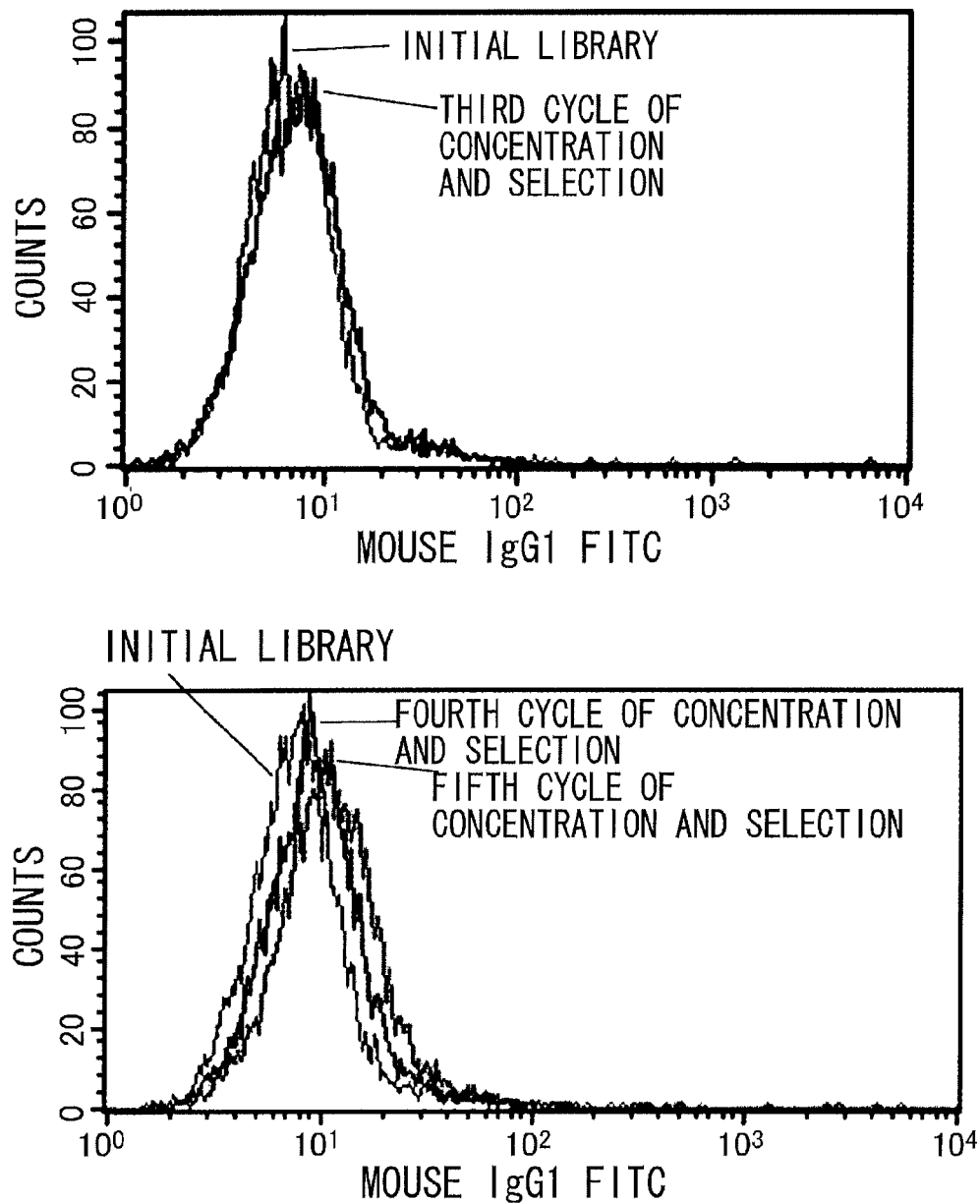
FIG. 9 shows a confirmation by flow cytometry of the process by which phages presenting scFv are concentrated using binding to the prostate cancer cell line DU145 as an index. The amount of phages which bind to DU145 cells increased with the increase of the number of rounds of concentration and selection.
Figure 10:
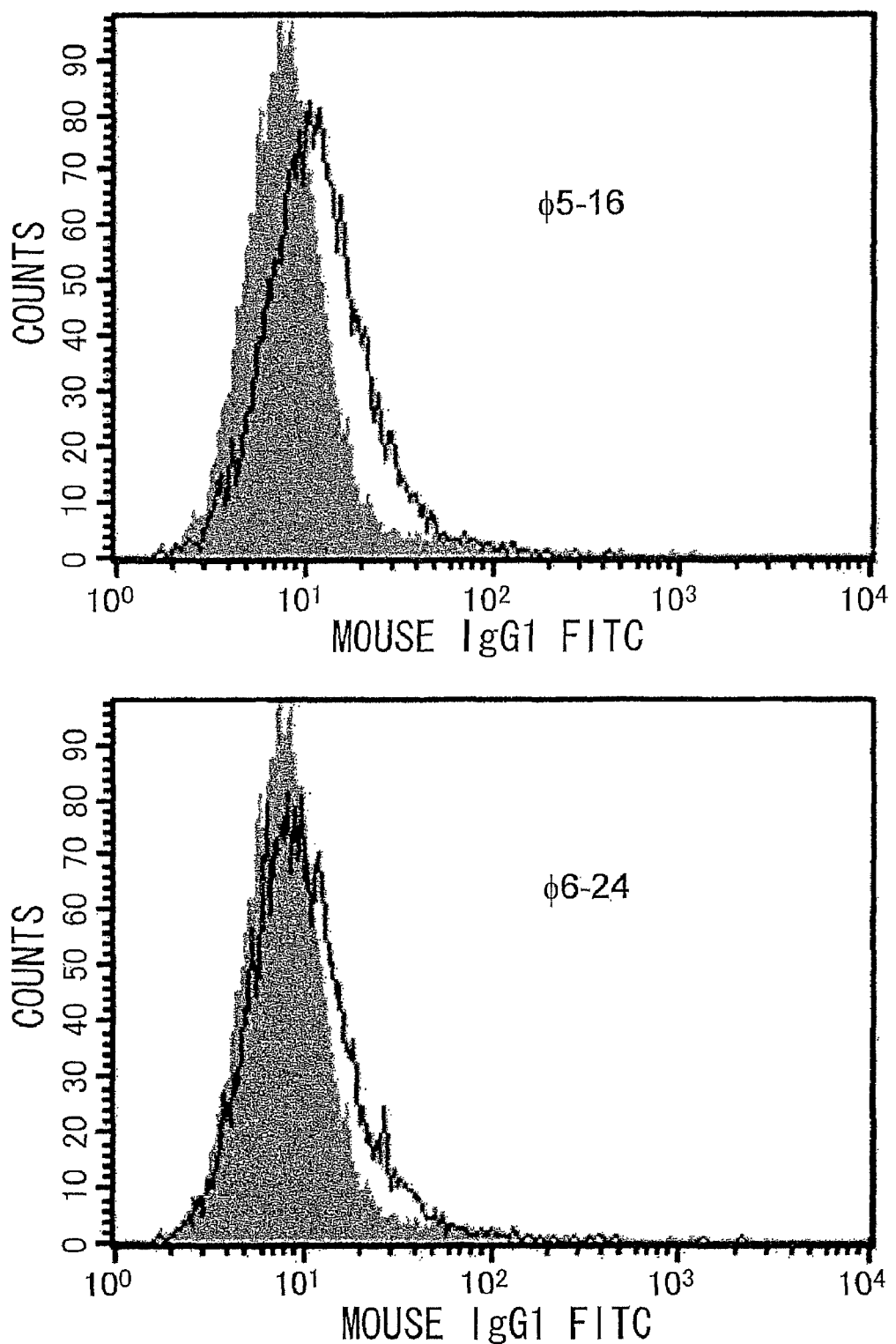
FIG. 10 shows a confirmation by flow cytometry of the binding of DU145 cells and DU145 cell-binding clones when these clones were isolated from a library after five or six cycles of concentration and selection.

Concentration and selection of phage clones were carried six times in total using the binding activity towards the cell surface as an index. DU145 cells were stained using a solution of scFv-presenting phage library selected by the binding to viable cell surfaces, and then subjected to a flow cytometry analysis. Specifically, immunostaining was carried out by mixing DU145 cells and the phage library solution, reacting a mouse anti-M13 antibody against M13 phage coat proteins (Amersham Bioscience) as a secondary antibody followed by reacting a FITC-labeled goat anti-mouse IgG antibody (Becton-Dickinson) as a tertiary antibody. The staining of the cells was analyzed by FACS Calibur (Becton-Dickinson) (FIG. 9). As the rounds of concentration and selection were carried out four to five times, the amount of phage that bound to the cells increased. Bound phages were cloned from libraries in which the proportion of cell-bound phages had increased, and from these libraries, bound clones 5-16 and 6-24 were identified after five and six rounds of concentration and selection, respectively (FIG. 10). The nucleotide sequences of the identified clones are shown in SEQ ID NO: 112 and 114, while the translated amino acid sequences are shown in SEQ ID NO: 113 and 115.

Figure 11:
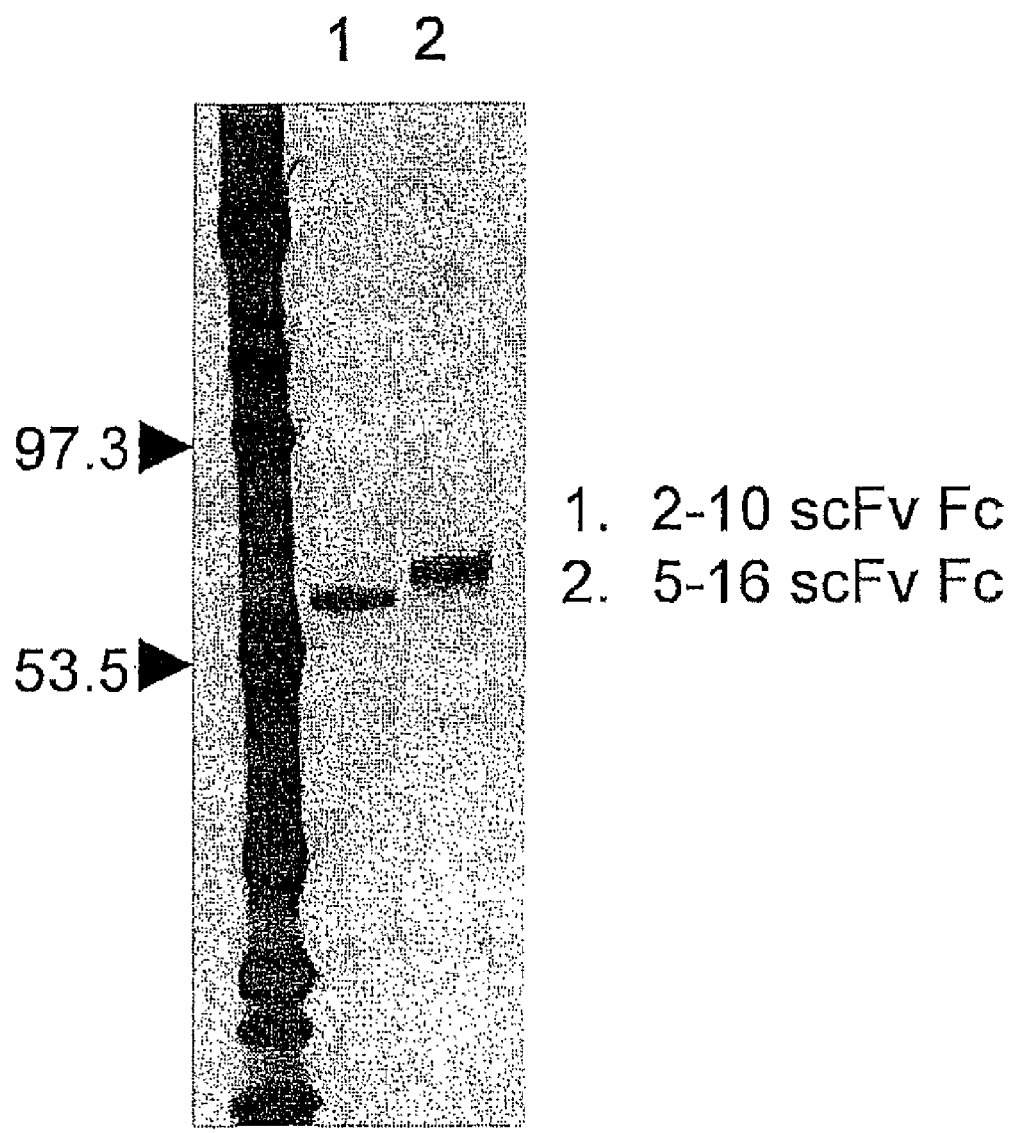
FIG. 11 is a photograph showing a silver staining of Protein A-purified scFv fusion proteins following separation by SDS-PAGE.
Figure 12:
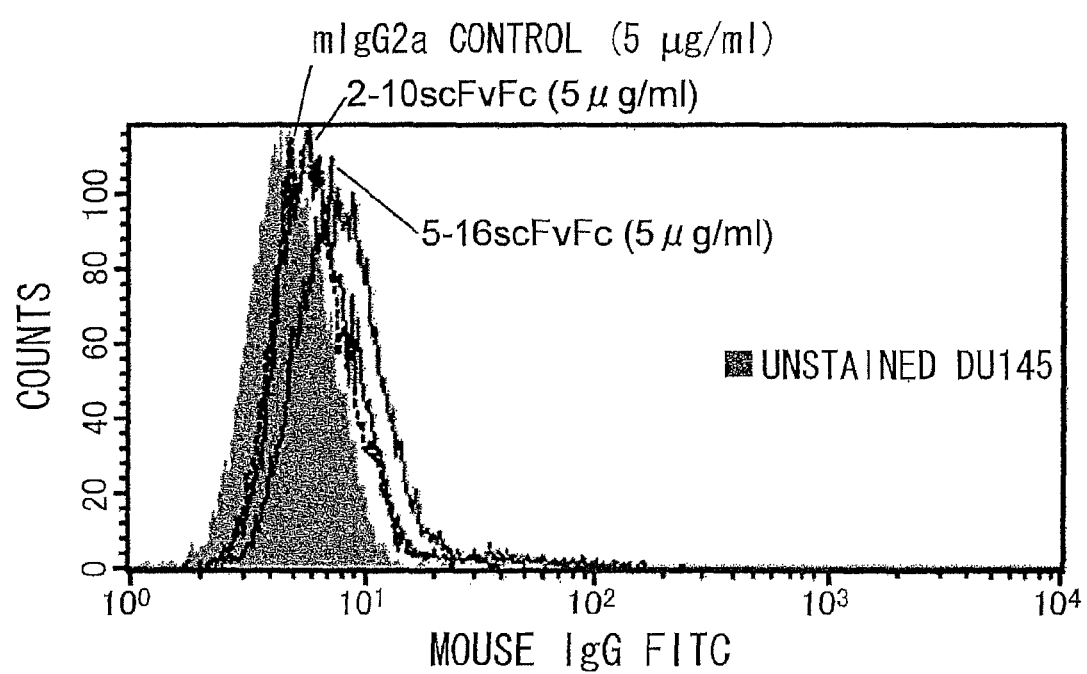
FIG. 12 is a graph showing a confirmation by flow cytometry of the binding of recombinant 5-16scFv Fc fusion proteins to DU145 cells.

A vector that expresses and secretes a chimeric protein in an animal cell system was constructed. This chimeric protein has an amino acid sequence corresponding to SEQ ID NO:

113 fused to a constant region sequence on the C-terminal side of mouse IgG2a hinge region. The expression cassette was designed so that a secretion signal sequence derived from a human heavy chain immunoglobulin is added to the N-terminus. The nucleotide sequence encoding this scFv fusion protein is shown in SEQ ID NO: 116, while the translated sequence is shown in SEQ ID NO: 117. The expression vector (comprising a G418 drug resistance gene) was introduced into CHO cells by electroporation, and stably expressing cell lines were selected by the sandwich ELISA method. Coating was performed under weakly alkaline conditions after diluting a goat anti-mouse IgG (gamma) antibody (Zymed, 62-6600) 1000 folds. After washing, blocking was carried out with a blocking solution containing BSA. After adding the culture supernatant and capturing the scFv fusion proteins, the captured amount was detected with an alkaline phosphatase-labeled rabbit anti-mouse IgG2a antibody. Stable cell lines with a high protein expression level were cultured and scFv fusion proteins were prepared by purification from the culture supernatant using HiTrap Protein A (Amersham Bioscience). Analysis of the purified scFv fusion proteins was confirmed by SDS-PAGE and silver staining (FIG. 11). The purified scFv fusion proteins were confirmed to bind to DU145 by flow cytometry (FIG. 12).

Example 4

Flow Cytometry Analysis Using NOG Serum

Figure 3:
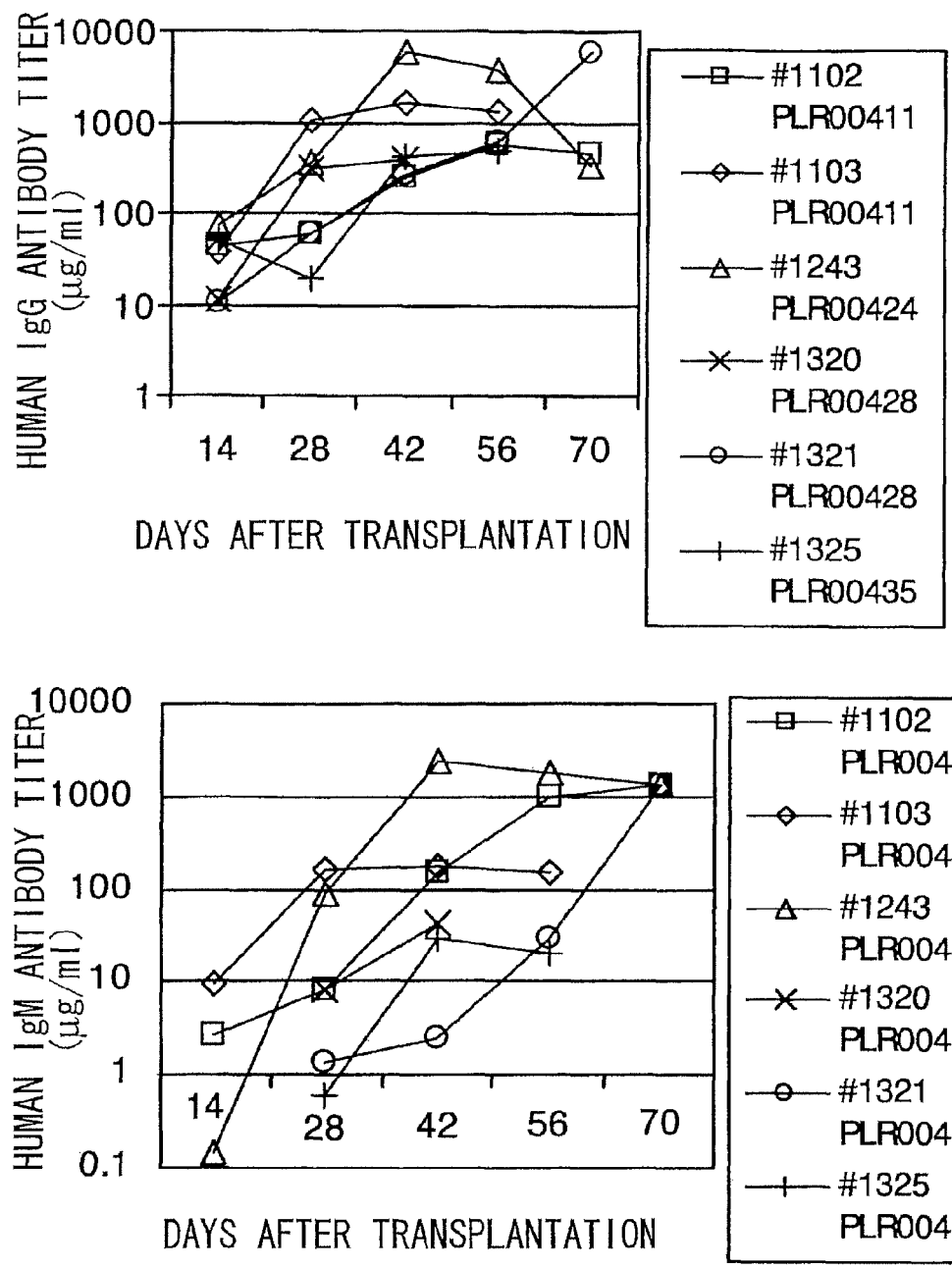
FIG. 3 shows the results of transplanting specimens from human prostate cancer and benign prostatic hyperplasia into NOG mice and monitoring the changes in human IgG and IgM antibody titers. An increase in antibody titer was observed in four (shown in the figure) out of the 40 transplanted specimens. RNAs were extracted from four of these cases and the antibody genes were amplified.
Figure 7:
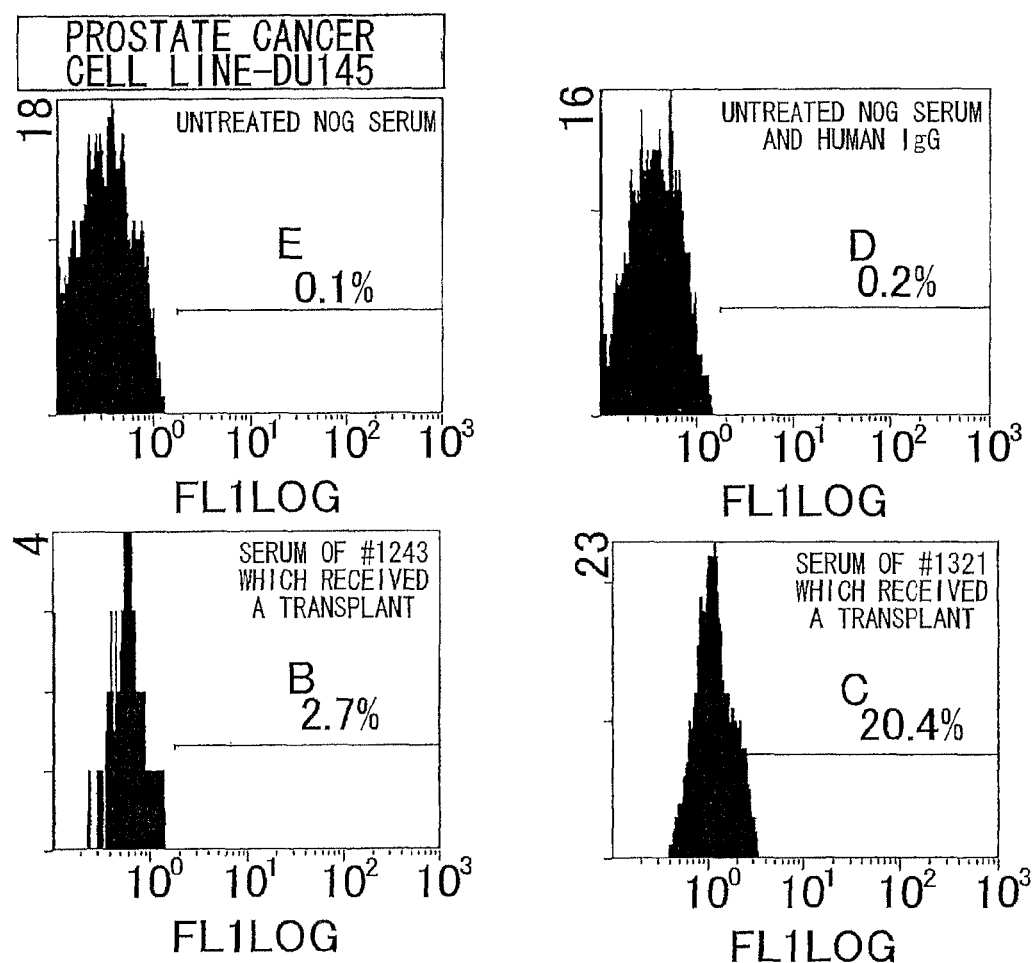
FIG. 7 shows results of a FACS investigation of whether human antibodies comprised in the serum of NOG mice transplanted with benign prostatic hyperplasia specimens recognize surface antigens on the prostate cancer cell line DU145. As is clear from the results, IgG antibodies recognizing the cancer cell line were present among IgG antibodies in the serum of NOG mice transplanted with benign prostatic hyperplasia.

Prostate cancer and benign prostatic hyperplasia specimens were transplanted into NOG mice. Following transplantation, blood was regularly collected from the orbital cavity of mice, the serum was separated, and changes in the titer of human antibodies (IgG IgM) were monitored. An increase in antibody titer was observed in six mice transplanted with four of the approximately 40 specimens (FIG. 3). These antibodies were diluted to 50 µg/ml and reacted with prostate cancer cell lines (DU145, PC3, LNCaP, and 22Rv1). After reacting for a predetermined amount of time, FITC-labeled anti-human IgG or IgM antibodies were added and the reaction was allowed to proceed again. After the reaction, whether or not cells were stained was confirmed by flow cytometry. As a result, human IgG antibodies of NOG mouse #1321, which was transplanted with the benign prostatic hyperplasia specimen, was shown to have recognized surface antigens of the prostate cancer cell line DU145 (FIG. 7).

Figure 8:
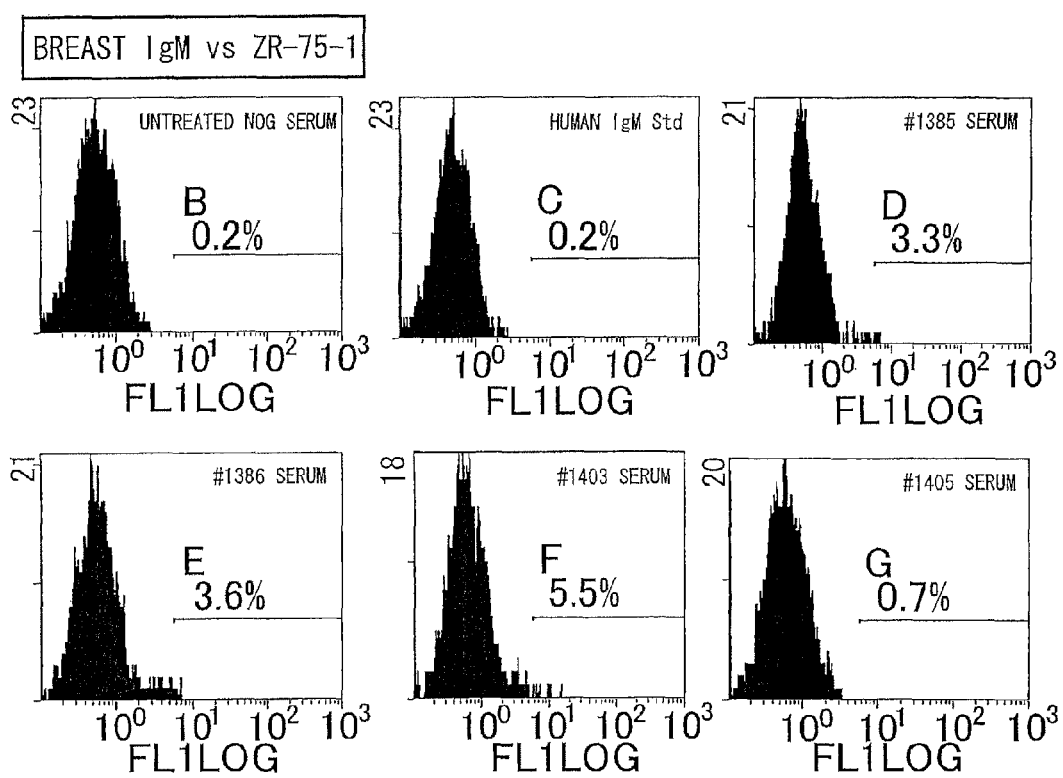
FIG. 8 shows results of a FACS investigation of whether human antibodies present in the serum of NOG mice transplanted with breast cancer (ductal carcinoma) specimens recognize surface antigens on the ductal carcinoma cell line ZR-75-1, As is clear from the results, IgM antibodies recognizing the carcinoma cell line were present among IgM antibodies in the serum of NOG mice transplanted with breast cancer.

Changes in human antibody titers in NOG mice transplanted with breast cancer specimens were similarly monitored. An increase in human antibody titer was observed in five mice transplanted with four of the ten specimens (FIG. 4). Cancer cell lines (MCF-7, MDA-MB-231, ZR-75-1, and BT-474) were immunostained in the same way as above using these antibodies and analyzed by flow cytometry. As a result, antibodies recognizing the cancer cell line ZR-75-1 were present among the human IgM antibodies in the sera of NOG mice #1385, #1386, and #1403 transplanted with breast cancer (FIG. 8).

Example 5

Figure 13:
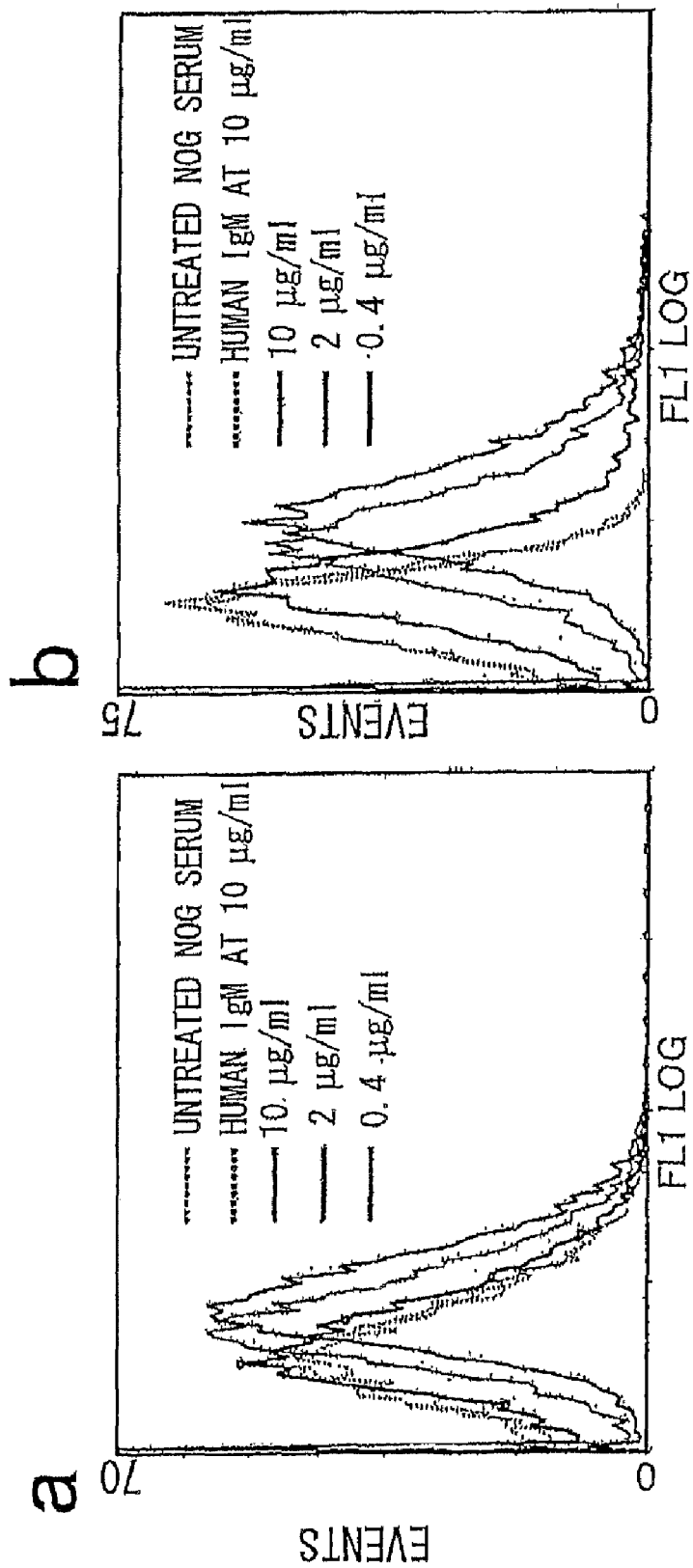
FIG. 13 shows a flow cytometry analysis after staining cancer cell lines using human antibodies that appear in the serum of NOG mice transplanted with stomach cancer tissues. Human IgM antibodies in the serum of mice transplanted with PLR0631 reacted with the human stomach cancer cell line AGS in a concentration-dependent manner (a). In addition, the serum of mice transplanted with PLR0624 reacted with the human stomach cancer cell line SNU-1 (b).

Detection by Flow Cytometry and Immunohistological Staining of Antitumor Antibodies Present in the Serum of NOG Mice Transplanted with Human Stomach Cancer Cancer tissues excised from twelve stomach cancer patients were transplanted into NOG mice, and the titer of human antibodies (IgG, IgM) was monitored in the same manner as with prostate cancer. NOG sera in which the human antibody titer reached 50 µg/ml or more were analyzed by flow cytometry using four types of stomach cancer lines (AGS, KATO III, SNU-1, and SNU-5) to see whether they comprised antibodies recognizing cancer cell lines. IgGs and IgMs in the sera of mice transplanted with PLR0530 reacted strongly with the human cancer cell line AGS (the details of which are described in Example 6), and the IgMs in the sera of mice transplanted with PLR0631 and PLR0659 similarly showed a strong reaction with AGS. Moreover, IgMs in the sera of mice transplanted with PLR0624 reacted strongly with SNU-1. Sera of mice transplanted with PLR0624 and PLR0631 were further diluted, the IgM concentration was adjusted to 10 µg/ml, 2 µg/ml, or 0.4 µg/ml, and an analysis by flow cytometry was carried out. Results are shown in FIGS. 13a and 13b.

Figure 14:
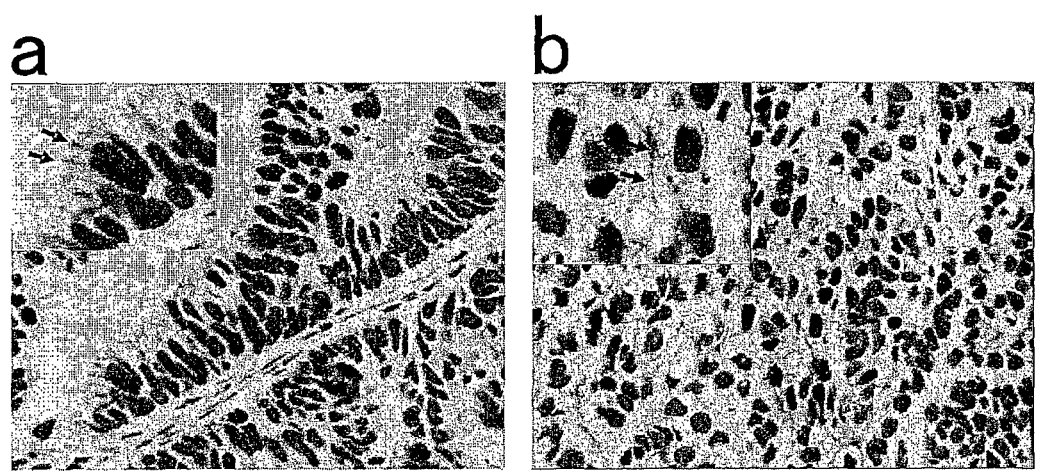

Next, using cell lines established at PharmaLogicals Research Pte Ltd, antibodies comprised in the sera of NOG mice were investigated by immunohistological staining to see whether those that recognize the cytoplasmic membrane of cancer cells are present. Immunohistological staining was carried out with a tissue array produced with an established cell line; the method of production is as follows: cancer cell lines serially engrafted for three or more generations in NOG mice were removed, fixed overnight with 4% paraformaldehyde, washed for two hours with 0.01 M phosphate buffer, and embedded in paraffin according to the AMeX method (Reference: Sato Y et al. (1986) Am J. Pathol. 125(3): 431-5). Cancer tissues with a diameter of 1.5 mm were excised from this block, transplanted into a new block of about 2.5 cm×3.0 cm, and a total of 36 different types (6×6) of cancer tissues were sequenced. The breakdown of the tissues is: 21 types of colorectal cancer; 4 types of small intestine cancer; 4 types of stomach cancer; and 1 type each of: adenocarcinoma of the ampulla of vater; breast cancer; bladder cancer; brain tumor; uterine cancer; lung cancer; and ovarian cancer. This tissue array was sliced into thin sections and after removing the paraffin, an immunohistological staining was carried out using the Ventana HX Discovery System (Ventana Medical Systems, Inc., Arizona, USA). Specifically, sera of NOG mice were diluted to an antibody concentration of 1 µg/ml, 2 µg/ml, or 10 µg/ml, added to the thinly sliced tissues, and reacted as primary antibodies. Moreover, biotin-SP-conjugated goat anti-human IgG antibodies (Jackson ImmunoResearch Labs) were added as secondary antibodies for the IgGs or biotin-SP-conjugated goat anti-human IgM antibodies (Jackson ImmunoResearch Labs) were added as secondary antibodies for the IgMs. Then a coloring reaction was carried out using DAB. An IHC with human IgGs present in the sera of mice transplanted with eleven different stomach cancer specimens confirmed a reactivity toward membrane antigens of cancer cells for one specimen, while human IgMs in the sera of mice transplanted with seven different of stomach cancer specimens were confirmed to react with membrane antigens of cancer cells for five specimens. Of the positive clones, the results of PLR0659 and PLR0530 are shown in the tables below (Tables 3 and 4). As evidenced from the tables, IgM antibodies comprised in the sera of mice transplanted with PLR0659 not only bound to the membranes of all four types of stomach cancer cells, but binding to membrane antigens of multiple colorectal cancers and small intestine cancers was also confirmed. On the other hand, the IgGs did not recognize the membrane antigens of cancer cells, and only recognized nuclear antigens. Reactivity to nuclear antigens was also observed for IgMs in all cases. It is presumed that nuclear antigens were exposed from a portion of cancer cells that denatured or died by necrosis in the course of proliferation, and antinuclear antibodies were produced in the body. Typical examples in which a staining of membrane antigens was observed by immunohistological staining are shown in FIGS. 14a and 14b.

TABLE 3

| NOG SERUM (PRIMARY ANTIBODY) | | | | | A[b] | | | | | | B | | |
|---|---|---|---|---|---|---|---|---|---|---|---|---|---|
| | | | | LOCATION OF | 1 | 2 | 3 | 4 | 5 | 6 | 1 | 2 | 3 |
| PLR No. | MOUSE No. | SERUM No. | Ig | POSITIVE REACTIONS | COLON AND/OR RECTUM | | | | | | | | |
| | | | | | 00023 | 00030 | 00059 | 00082 | 00087 | 00119 | 00122 | 00123 | 00151 |
| 00659 | 2092 | 1452 | G | CELL MEMBRANE | − | − | − | − | − | − | − | − | − |
| | | | | NUCLEUS | + | + | + | + | + | + | + | + | + |
| | | | M | LUMINAL SIDE CELL MEMBRANE | − | − | + | + | − | − | − | − | − |
| | | | | OUTER BASAL CELL MEMBRANE | + | + | + | + | − | − | + | + | + |
| | | | | CELL MEMBRANE | − | − | − | − | − | − | − | − | − |
| | | | | MUCOSAL SUBSTANCE | − | − | − | − | − | − | − | + | − |
| | | | | NUCLEUS | + | + | + | + | + | + | + | + | + |

| NOG SERUM (PRIMARY ANTIBODY) | | | | | B | | | C | | | | | |
|---|---|---|---|---|---|---|---|---|---|---|---|---|---|
| | | | | LOCATION OF | 4 | 5 | 6 | 1 | 2 | 3 | 4 | 5 | 6 |
| PLR No. | MOUSE No. | SERUM No. | Ig | POSITIVE REACTIONS | COLON AND/OR RECTUM | | | | | | | | |
| | | | | | 00168 | 00215 | 00233 | 00241 | 00254 | 00261 | 00273 | 00325 | 00355 |
| 00659 | 2092 | 1452 | G | CELL MEMBRANE | − | − | − | − | − | − | − | − | − |
| | | | | NUCLEUS | + | + | + | + | + | + | + | + | + |
| | | | M | LUMINAL SIDE CELL MEMBRANE | − | − | − | − | − | − | − | − | − |
| | | | | OUTER BASAL CELL MEMBRANE | + | − | − | + | − | + | − | − | − |
| | | | | CELL MEMBRANE | − | + | − | − | − | − | − | − | − |
| | | | | MUCOSAL SUBSTANCE | − | − | − | − | − | − | − | − | − |
| | | | | NUCLEUS | + | + | + | + | + | + | + | + | + |

| NOG SERUM (PRIMARY ANTIBODY) | | | | | D | | | | | | E |
|---|---|---|---|---|---|---|---|---|---|---|---|
| | | | | LOCATION OF | 1 | 2 | 3 | 4 VATER/ | 5 | 6 | 1 |
| PLR No. | MOUSE No. | SERUM No. | Ig | POSITIVE REACTIONS | COLON AND/OR RECTUM | | | DUODENUM | SMALL INTESTINE | | |
| | | | | | 00357 | 00379 | 00423 | 00077 | 00186 | 00229 | 00304 |
| 00659 | 2092 | 1452 | G | CELL MEMBRANE | − | − | − | − | − | − | − |
| | | | | NUCLEUS | + | + | + | + | + | + | + |
| | | | M | LUMINAL SIDE CELL MEMBRANE | − | − | + | − | − | − | − |
| | | | | OUTER BASAL CELL MEMBRANE | − | − | + | − | − | − | + |
| | | | | CELL MEMBRANE | − | − | − | − | + | − | − |
| | | | | MUCOSAL SUBSTANCE | − | − | + | + | − | − | − |
| | | | | NUCLEUS | + | + | + | + | + | + | + |

| NOG SERUM (PRIMARY ANTIBODY) | | | | | E | | | | | F | | |
|---|---|---|---|---|---|---|---|---|---|---|---|---|
| | | | | LOCATION OF | 2 | 3 | 4 | 5 | 6 | 1 | 2 | 3 |
| PLR No. | MOUSE No. | SERUM No. | Ig | POSITIVE REACTIONS | STOMACH | | | | VATER | BREAST | BLADDER | BRAIN |
| | | | | | 00020 | 00269 | 00336 | 00339 | 00266 | 00478 | 00387 | 00032 |
| 00659 | 2092 | 1452 | G | CELL MEMBRANE | − | − | − | − | − | − | − | − |
| | | | | NUCLEUS | + | + | + | + | + | + | + | + |
| | | | M | LUMINAL SIDE CELL MEMBRANE | − | − | − | − | − | − | − | − |
| | | | | OUTER BASAL CELL MEMBRANE | − | + | − | − | + | − | − | − |
| | | | | CELL MEMBRANE | + | − | + | + | − | + | + | − |
| | | | | MUCOSAL SUBSTANCE | − | − | − | − | − | − | − | − |
| | | | | NUCLEUS | + | + | + | + | + | + | + | + |

TABLE 3-continued

| | NOG SERUM | | | | | F | | |
|---|---|---|---|---|---|---|---|---|
| | (PRIMARY ANTIBODY) | | | LOCATION OF | | 4 | 5 | 6 |
| PLR No. | MOUSE No. | SERUM No. | Ig | POSITIVE REACTIONS | | UTERUS 00018 | LUNG 00327 | OVARY 00337 |
| 00659 | 2092 | 1452 | G | CELL MEMBRANE | | − | − | − |
| | | | | NUCLEUS | | + | + | + |
| | | | M | LUMINAL SIDE CELL MEMBRANE | | − | − | − |
| | | | | OUTER BASAL CELL MEMBRANE | | − | − | − |
| | | | | CELL MEMBRANE | | + | + | − |
| | | | | MUCOSAL SUBSTANCE | | − | − | − |
| | | | | NUCLEUS | | + | + | + |

TABLE 4

| NOG SERUM | | | | | A | | | | | | B | | |
|---|---|---|---|---|---|---|---|---|---|---|---|---|---|
| (PRIMARY ANTIBODY) | | | | LOCATION OF | 1 | 2 | 3 | 4 | 5 | 6 | 1 | 2 | 3 |
| PLR No. | MOUSE No. | SERUM No. | Ig | POSITIVE REACTIONS | COLON AND/OR RECTUM | | | | | | | | |
| | | | | | 00023 | 00030 | 00059 | 00082 | 00087 | 00119 | 00122 | 00123 | 00151 |
| 00530 | 1619 | 980 | G | CELL MEMBRANE | − | − | − | − | − | − | − | − | − |
| | | | | NUCLEUS | + | + | + | + | + | + | + | + | + |
| | | | M | LUMINAL SIDE CELL MEMBRANE | − | − | − | − | − | − | − | − | − |
| | | | | OUTER BASAL CELL MEMBRANE | − | − | − | − | − | − | − | − | − |
| | | | | CELL MEMBRANE | + | − | − | − | − | − | − | − | − |
| | | | | MUCOSAL SUBSTANCE | − | − | − | − | − | − | − | − | − |
| | | | | NUCLEUS | + | + | + | + | + | + | + | + | + |

| NOG SERUM | | | | | B | | | C | | | | | |
|---|---|---|---|---|---|---|---|---|---|---|---|---|---|
| (PRIMARY ANTIBODY) | | | | LOCATION OF | 4 | 5 | 6 | 1 | 2 | 3 | 4 | 5 | 6 |
| PLR No. | MOUSE No. | SERUM No. | Ig | POSITIVE REACTIONS | COLON AND/OR RECTUM | | | | | | | | |
| | | | | | 00168 | 00215 | 00233 | 00241 | 00254 | 00261 | 00273 | 00325 | 00355 |
| 00530 | 1619 | 980 | G | CELL MEMBRANE | − | − | − | − | − | − | − | − | − |
| | | | | NUCLEUS | + | + | + | + | + | + | + | + | + |
| | | | M | LUMINAL SIDE CELL MEMBRANE | − | − | − | + | − | − | − | − | − |
| | | | | OUTER BASAL CELL MEMBRANE | − | − | − | − | − | − | − | − | − |
| | | | | CELL MEMBRANE | − | − | − | + | − | − | − | − | − |
| | | | | MUCOSAL SUBSTANCE | − | − | − | − | − | − | − | − | − |
| | | | | NUCLEUS | + | + | + | + | + | + | + | + | + |

| NOG SERUM | | | | | D | | | | | | E |
|---|---|---|---|---|---|---|---|---|---|---|---|
| (PRIMARY ANTIBODY) | | | | LOCATION OF | 1 | 2 | 3 | 4 VATER/ | 5 | 6 | 1 |
| PLR No. | MOUSE No. | SERUM No. | Ig | POSITIVE REACTIONS | COLON AND/OR RECTUM | | | DUODENUM | SMALL INTESTINE | | |
| | | | | | 00357 | 00379 | 00423 | 00077 | 00186 | 00229 | 00304 |
| 00530 | 1619 | 980 | G | CELL MEMBRANE | − | − | − | − | − | − | − |
| | | | | NUCLEUS | + | + | + | + | + | + | + |
| | | | M | LUMINAL SIDE CELL MEMBRANE | − | − | − | − | − | − | − |
| | | | | OUTER BASAL CELL MEMBRANE | − | − | − | − | − | − | − |
| | | | | CELL MEMBRANE | − | − | − | − | − | − | − |

TABLE 4-continued

| | | | | | | | | | | | |
|---|---|---|---|---|---|---|---|---|---|---|---|
| | | MUCOSAL SUBSTANCE | – | – | – | – | – | – | – | | |
| | | NUCLEUS | + | + | + | + | + | + | + | | |

| NOG SERUM (PRIMARY ANTIBODY) | | | | | | E | | | | | F | | |
|---|---|---|---|---|---|---|---|---|---|---|---|---|---|
| | | | | LOCATION OF | 2 | 3 | 4 | 5 | 6 | 1 | 2 | 3 |
| PLR No. | MOUSE No. | SERUM No. | Ig | POSITIVE REACTIONS | STOMACH | | | | VATER | BREAST | BLADDER | BRAIN |
| | | | | | 00020 | 00269 | 00336 | 00339 | 00266 | 00478 | 00387 | 00032 |
| 00530 | 1619 | 980 | G | CELL MEMBRANE | – | – | – | – | – | – | – | – |
| | | | | NUCLEUS | 30 | + | + | + | + | + | + | + |
| | | | M | LUMINAL SIDE CELL MEMBRANE | – | – | – | – | – | – | – | – |
| | | | | OUTER BASAL CELL MEMBRANE | – | + | – | – | – | – | – | – |
| | | | | CELL MEMBRANE | – | – | – | – | – | – | – | – |
| | | | | MUCOSAL SUBSTANCE | – | – | – | – | – | – | – | – |
| | | | | NUCLEUS | + | + | + | + | + | + | + | + |

| NOG SERUM (PRIMARY ANTIBODY) | | | | | F | | |
|---|---|---|---|---|---|---|---|
| | | | | LOCATION OF | 4 | 5 | 6 |
| PLR No. | MOUSE No. | SERUM No. | Ig | POSITIVE REACTIONS | UTERUS | LUNG | OVARY |
| | | | | | 00018 | 00327 | 00337 |
| 00530 | 1619 | 980 | G | CELL MEMBRANE | – | – | – |
| | | | | NUCLEUS | + | + | + |
| | | | M | LUMINAL SIDE CELL MEMBRANE | – | – | – |
| | | | | OUTER BASAL CELL MEMBRANE | – | – | – |
| | | | | CELL MEMBRANE | – | – | – |
| | | | | MUCOSAL SUBSTANCE | – | – | – |
| | | | | NUCLEUS | + | + | + |

Example 6

Reactivity of Chimeric Antibodies Selected by Phage Panning Towards Cancer Cells Since human IgGs and IgMs in the sera of NOG mice transplanted with the stomach cancer tissue PLR0530 reacted strongly with the stomach cancer cell line AGS (FIGS. 15a and 15b), an scFv-presenting phage library was produced from the variable region genes of antibodies produced by plasma cells that proliferated when stomach cancer sues were transplanted, based on the methods indicated in Examples 2 and 3. Concentration and selection of phage clones that bind to the cell surface of the stomach cancer cell line AGS were carried out according to the method indicated in Example 3. Following the concentration procedure, binding phages were cloned from libraries where an increase in the amount of binding phages was observed, and clone 1-3 which corresponds to SEQ ID NO: 118 was isolated (FIG. 16). The translated amino acid sequence corresponding to clone 1-3 is shown in SEQ ID NO: 119. An expression vector for scFv-mouse IgG2a constant region fusion protein corresponding to this clone sequence was constructed and introduced into CHO cells to establish a stably expressing cell line. The nucleotide sequence encoding the scFv fusion protein is shown in SEQ ID NO: 120, while the translated sequence is shown in SEQ ID NO: 121. Binding of the scFv fusion proteins purified from the culture supernatant (FIG. 17) to AGS cells was confirmed by flow cytometry (FIG. 18).

Next, an immunohistological staining of cancer tissues was carried out using this chimeric antibody. Stomach, colon, and small intestine provided from cancer patients were used as specimens. Each tissue comprises adjacent non-tumor tissues in addition to the cancer tissue. As a result of immunohistological staining, the following were stained in the stomach: cytoplasm of cancer cells, the cytoplasm of hyperplastic gastric mucosal cells, and the cytoplasm of normal gastric mucosal cells and gastric gland cells (FIG. 19). Moreover, the luminal side cell membrane and cytoplasm of cancer cells or normal mucosal membrane epithelial cells were stained in the colon, and the luminal side cell membrane and cytoplasm of hyperplastic mucosal membrane epithelial cells were stained in the small intestine (FIG. 19). In this manner, it was revealed that antibodies reacting to cancer cells and cancer tissues are obtained by this method. To obtain antibodies with a high specificity, it would be necessary to repeat this method and obtain several candidate clones.

INDUSTRIAL APPLICABILITY

Using the present invention, plasma cells that are infiltrating lesion tissues such as cancer tissues can be differentiated into antibody-producing plasma cells, and they can be proliferated and condensed to a high concentration. As a result, cells producing antibodies that recognize cancer cells and lesion tissues can be easily separated and obtained without having to clone antibody-producing cells in vitro. Moreover, antibody genes can be easily separated from these cells. The present invention is highly significant in the diagnosis and treatment of diseases such as cancer since it provides a method for easily acquiring genes for human antibodies that recognize lesion tissues such as cancer.

Antibodies are administered to humans during diagnoses and treatments that utilize antibodies. For example, during the diagnosis of cancer using antibodies, antibody molecules labeled with traceable labels are administered and the presence of cancer is indicated by the location of the antibodies. Moreover, with respect to treatment, in addition to the direct effect of the antibodies, antibodies onto which anticancer agents are bound are administered to patients. A high degree of safety is expected with human antibodies when administered to humans, and since the species is the same, concentrations in blood are expected to be stably maintainable for a long period of time.

Using the present invention, genes of cancer-specific antibodies can be efficiently separated from numerous cancer tissues. Moreover, it is also possible that the mechanism which directs the immune system towards a dominantly humoral immunity may be clarified. Therefore, the present invention has the potential of being useful in the development of not only antibodies but also low molecular weight pharmaceuticals such as those for treating cancer, autoimmune disease, infectious disease, and allergic disease.

The invention claimed is:

1. A method of producing cells which produce an antibody or antigen-binding portion thereof, wherein the method comprises the steps of:
   (a) transplanting a lesion tissue comprising infiltrating lymphocytes into a highly immunodeficient non-human animal, wherein the animal is not a severe combined immunodeficient (SCID) mouse;
   (b) detecting the proliferation of plasma cells at the site of transplantation; and
   (c) recovering a sample of the lesion tissue from the site of transplantation, wherein the sample comprises plasma cells.

2. The method of claim 1, further comprising the step of:
   (d) excising a plasma cell from the recovered sample of lesion tissue and fusing the plasma cell with a partner cell.

3. The method of claim 1, wherein the transplanted lesion tissue comprises cancer cells, hyperplasia cells, or virus-infected cells.

4. The method of claim 3, wherein the transplanted lesion tissue comprises cells of a solid cancer or a blood cancer.

5. The method of claim 4, wherein the transplanted lesion tissue comprises cells of a solid cancer that is a prostate cancer, stomach cancer, breast cancer, lung cancer, liver cancer, colorectal cancer, or pancreatic cancer.

6. The method of claim 3, wherein the transplanted lesion tissue comprises cells of benign prostatic hyperplasia.

7. The method of claim 1, wherein the highly immunodeficient non-human animal lacks NK cells.

8. The method of claim 1, wherein the highly immunodeficient non-human animal lacks T cells, B cells, and NK cells.

9. The method of claim 1, wherein the lesion tissue is from a human subject.

10. The method of claim 1, wherein the antibody is a human antibody.

11. The method of claim 1, wherein step (b) comprises determining the level of human antibodies in the serum of the animal, wherein a higher level of human antibodies in the serum is indicative of a higher number of plasma cells at the site of transplantation.

12. A method of producing an antibody or antigen-binding portion thereof, wherein the antibody or antigen-binding portion thereof is isolated from the antibody-producing cells produced according to claim 1.

13. The method of claim 12, wherein the transplanted lesion tissue comprises cancer cells, hyperplasia cells, or virus-infected cells.

14. The method of claim 13, wherein the transplanted lesion tissue comprises cells of a solid cancer or a blood cancer.

15. The method of claim 14, wherein the transplanted lesion tissue comprises cells of a solid cancer that is a prostate cancer, stomach cancer, breast cancer, lung cancer, liver cancer, colorectal cancer or pancreatic cancer.

16. The method of claim 13, wherein the transplanted lesion tissue comprises cells of a benign prostatic hyperplasia.

17. The method of claim 13, wherein the antibody or an antigen-binding portion thereof is an IgG, an IgM, an Fab, an F(ab')2, an Fv, or a single chain Fv.

18. The method of claim 17, wherein the antibody is an IgG.

19. The method of claim 17, wherein the antibody is an IgM.

20. The method of claim 17, wherein the antibody or antigen-binding portion thereof is a single chain Fv.

21. The method of claim 12, further comprising conjugating the antibody or antigen-binding portion to a molecule selected from the group consisting of polyethylene glycol, a radioisotope, a chemotherapeutic, a cytotoxic substance, and a labeling substance.

22. The method of claim 3, wherein the solid cancer is a prostate cancer.

23. The method of claim 3, wherein the solid cancer is a stomach cancer.

24. The method of claim 3, wherein the solid cancer is a breast cancer.

25. The method of claim 3, wherein the solid cancer is a lung cancer.

26. The method of claim 3, wherein the solid cancer is a liver cancer.

27. The method of claim 3, wherein the solid cancer is a colorectal cancer.

28. The method of claim 3, wherein the solid cancer is a pancreatic cancer.

29. The method of claim 15, wherein the solid cancer is a prostate cancer.

30. The method of claim 15, wherein the solid cancer is a stomach cancer.

31. The method of claim 15, wherein the solid cancer is a breast cancer.

32. The method of claim 3, wherein the solid cancer is a lung cancer.

33. The method of claim 15, wherein the solid cancer is a liver cancer.

34. The method of claim 15, wherein the solid cancer is a colorectal cancer.

35. The method of claim 15, wherein the solid cancer is a pancreatic cancer.

* * * * *

UNITED STATES PATENT AND TRADEMARK OFFICE
CERTIFICATE OF CORRECTION

PATENT NO.         : 8,343,761 B2
APPLICATION NO.    : 13/187677
DATED              : January 1, 2013
INVENTOR(S)        : Masayuki Tsuchiya et al.

It is certified that error appears in the above-identified patent and that said Letters Patent is hereby corrected as shown below:

On the title page item (73) under "Assignees", delete "CIEA International Inc., Kanagawa (JP)"

Signed and Sealed this
Twelfth Day of February, 2013

Teresa Stanek Rea
*Acting Director of the United States Patent and Trademark Office*

```
                         SEQUENCE LISTING

<160> NUMBER OF SEQ ID NOS: 121

<210> SEQ ID NO 1
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 1
caggtkcagc tggtgcagtc tgg                                              23

<210> SEQ ID NO 2
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 2
caggtccagc ttgtgcagtc tgg                                              23

<210> SEQ ID NO 3
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 3
saggtccagc tggtacagtc tgg                                              23

<210> SEQ ID NO 4
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 4
caratgcagc tggtgcagtc tgg                                              23

<210> SEQ ID NO 5
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 5
cagatcacct tgaaggagtc tggt                                             24
```

```
<210> SEQ ID NO 6
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 6
caggtcacct tgarggagtc tggt                                          24

<210> SEQ ID NO 7
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 7
gargtgcagc tggtggagtc tgg                                           23

<210> SEQ ID NO 8
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 8
caggtgcagc tggtggagtc tgg                                           23

<210> SEQ ID NO 9
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 9
gaggtgcagc tgttggagtc tgg                                           23

<210> SEQ ID NO 10
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 10
cagstgcagc tgcaggagtc gggc                                          24

<210> SEQ ID NO 11
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 11
caggtgcagc tacagcagtg gggc                                          24

<210> SEQ ID NO 12
<211> LENGTH: 24
<212> TYPE: DNA
<213> ORGANISM: Artificial
<220> FEATURE:
<223> OTHER INFORMATION: An artificially synthesized primer sequence
```

```
<400> SEQUENCE: 12
gargtgcagc tggtgcagtc tgga                                              24

<210> SEQ ID NO 13
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 13
caggtacagc tgcagcagtc aggt                                              24

<210> SEQ ID NO 14
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 14
caggtscagc tggtgcaatc tgg                                               23

<210> SEQ ID NO 15
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 15
tgaggagacg gtgaccaggg tkcc                                              24

<210> SEQ ID NO 16
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 16
tgaagagacg gtgaccattg tccc                                              24

<210> SEQ ID NO 17
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 17
tgaggagacg gtgaccgtgg tccc                                              24

<210> SEQ ID NO 18
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 18
racatccaga tgacccagtc tcca                                              24

<210> SEQ ID NO 19
<211> LENGTH: 24
<212> TYPE: DNA
```

```
<213> ORGANISM: Artificial
<220> FEATURE:
<223> OTHER INFORMATION: An artificially synthesized primer sequence

<400> SEQUENCE: 19
gmcatccagt tgacccagtc tcca                                              24

<210> SEQ ID NO 20
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 20
gccatccrga tgacccagtc tcca                                              24

<210> SEQ ID NO 21
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 21
gtcatctgga tgacccagtc tcca                                              24

<210> SEQ ID NO 22
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 22
gatattgtga tgacccagac tcca                                              24

<210> SEQ ID NO 23
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 23
gatrttgtga tgactcagtc tcca                                              24

<210> SEQ ID NO 24
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 24
gaaattgtgt tgacrcagtc tcca                                              24

<210> SEQ ID NO 25
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 25
gaaatagtga tgacgcagtc tcca                                              24
```

<210> SEQ ID NO 26
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 26
gaaattgtaa tgacacagtc tcca                                       24

<210> SEQ ID NO 27
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 27
gacatcgtga tgacccagtc tcca                                       24

<210> SEQ ID NO 28
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 28
gaaacgacac tcacgcagtc tcca                                       24

<210> SEQ ID NO 29
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 29
gaaattgtgc tgactcagtc tcca                                       24

<210> SEQ ID NO 30
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 30
gatgttgtga tgacacagtc tcca                                       24

<210> SEQ ID NO 31
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 31
acgtttgatt tccaccttgg tccc                                       24

<210> SEQ ID NO 32
<211> LENGTH: 24
<212> TYPE: DNA
<213> ORGANISM: Artificial
<220> FEATURE:
<223> OTHER INFORMATION: An artificially synthesized primer sequence

```
<400> SEQUENCE: 32
acgtttgatc tccascttgg tccc                                              24

<210> SEQ ID NO 33
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 33
acgtttgata tccactttgg tccc                                              24

<210> SEQ ID NO 34
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 34
acgtttaatc tccagtcgtg tccc                                              24

<210> SEQ ID NO 35
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 35
cagtctgtgc tgactcagcc accc                                              24

<210> SEQ ID NO 36
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 36
cagtctgtgy tgacgcagcc gccc                                              24

<210> SEQ ID NO 37
<211> LENGTH: 22
<212> TYPE: DNA
<213> ORGANISM: Artificial
<220> FEATURE:
<223> OTHER INFORMATION: An artificially synthesized primer sequence

<400> SEQUENCE: 37
cagtctgccc tgactcagcc ts                                                22

<210> SEQ ID NO 38
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 38
tcctatgwgc tgactcagcc accc                                              24

<210> SEQ ID NO 39
<211> LENGTH: 24
<212> TYPE: DNA
```

```
<213> ORGANISM: Artificial
<220> FEATURE:
<223> OTHER INFORMATION: An artificially synthesized primer sequence

<400> SEQUENCE: 39
tcctatgagc tgacacagcy accc                                          24

<210> SEQ ID NO 40
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 40
tcttctgagc tgactcagga ccct                                          24

<210> SEQ ID NO 41
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 41
tcctatgagc tgatgcagcc accc                                          24

<210> SEQ ID NO 42
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 42
cagcctgtgc tgactcaatc atcc                                          24

<210> SEQ ID NO 43
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 43
cagcttgtgc tgactcaatc gccc                                          24

<210> SEQ ID NO 44
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 44
ctgcctgtgc tgactcagcc cccg                                          24

<210> SEQ ID NO 45
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 45
cagcctgtgc tgactcagcc ayct                                          24
```

```
<210> SEQ ID NO 46
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 46
caggctgtgc tgactcagcc ggct                                          24

<210> SEQ ID NO 47
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 47
aattttatgc tgactcagcc ccac                                          24

<210> SEQ ID NO 48
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 48
cagrctgtgg tgactcagga gccc                                          24

<210> SEQ ID NO 49
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 49
cagactgtgg tgacccagga gcca                                          24

<210> SEQ ID NO 50
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 50
cwgcctgtgc tgactcagcc acct                                          24

<210> SEQ ID NO 51
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 51
caggcagggc tgactcagcc accc                                          24

<210> SEQ ID NO 52
<211> LENGTH: 24
<212> TYPE: DNA
<213> ORGANISM: Artificial
<220> FEATURE:
<223> OTHER INFORMATION: An artificially synthesized primer sequence
```

-continued

```
<400> SEQUENCE: 52
acctaggacg gtgaccttgg tccc                                              24

<210> SEQ ID NO 53
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 53
acctaggacg gtcagcttgg tccc                                              24

<210> SEQ ID NO 54
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 54
accgaggacg gtcagctggg tgcc                                              24

<210> SEQ ID NO 55
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 55
cgtcaccggt tcggggaagt agtc                                              24

<210> SEQ ID NO 56
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 56
ggggaattct cacaggagac gag                                               23

<210> SEQ ID NO 57
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 57
ggcagttcca gatttcaact gct                                               23

<210> SEQ ID NO 58
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 58 cag gtc cag ctt gtg cag tct ggg gct gag gtg cag aag cct gag tcc        48
Gln Val Gln Leu Val Gln Ser Gly Ala Glu Val Gln Lys Pro Glu Ser
1               5                   10                  15 tcg gtg aag gtc tcc tgc aag gct tct gga ggc acc ctc acc aac tat        96
```

```
                gct atc acc tgg gtg cga cag gcc cct gga caa ggg ctt gag tgg atg       144
                Ala Ile Thr Trp Val Arg Gln Ala Pro Gly Gln Gly Leu Glu Trp Met
                    35                  40                  45 gga agg atc atc cct atg att cat atg aca aat tac gca cag aag ttc       192
                Gly Arg Ile Ile Pro Met Ile His Met Thr Asn Tyr Ala Gln Lys Phe
                50                  55                  60 cag ggc aga gtc acg att acc gcg gac aat tcc acg aga aca gcc tac       240
                Gln Gly Arg Val Thr Ile Thr Ala Asp Asn Ser Thr Arg Thr Ala Tyr
                65                  70                  75                  80 atg gag gtg aag agt ctc aga tct gac gac acg gcc gta tat tat tgt       288
                Met Glu Val Lys Ser Leu Arg Ser Asp Asp Thr Ala Val Tyr Tyr Cys
                                85                  90                  95 gcg aga gat ttt ttc ggt tcg ggg agt tac tat tcc ggt ctg gac gtc       336
                Ala Arg Asp Phe Phe Gly Ser Gly Ser Tyr Tyr Ser Gly Leu Asp Val
                            100                 105                 110 tgg ggc caa ggg acc acg gtc acc gtc tcc tca                           369
                Trp Gly Gln Gly Thr Thr Val Thr Val Ser Ser
                            115                 120

<210> SEQ ID NO 59
<211> LENGTH: 123
<212> TYPE: PRT
<213> ORGANISM: Homo sapiens

<400> SEQUENCE: 59

Gln Val Gln Leu Val Gln Ser Gly Ala Glu Val Gln Lys Pro Glu Ser
1               5                   10                  15

Ser Val Lys Val Ser Cys Lys Ala Ser Gly Gly Thr Leu Thr Asn Tyr
            20                  25                  30

Ala Ile Thr Trp Val Arg Gln Ala Pro Gly Gln Gly Leu Glu Trp Met
        35                  40                  45

Gly Arg Ile Ile Pro Met Ile His Met Thr Asn Tyr Ala Gln Lys Phe
    50                  55                  60

Gln Gly Arg Val Thr Ile Thr Ala Asp Asn Ser Thr Arg Thr Ala Tyr
65                  70                  75                  80

Met Glu Val Lys Ser Leu Arg Ser Asp Asp Thr Ala Val Tyr Tyr Cys
                85                  90                  95

Ala Arg Asp Phe Phe Gly Ser Gly Ser Tyr Tyr Ser Gly Leu Asp Val
            100                 105                 110

Trp Gly Gln Gly Thr Thr Val Thr Val Ser Ser
        115                 120

<210> SEQ ID NO 60
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 60 cag ctg gtg caa tct ggg gct gag gtg aag aag cct gag tcc tcg gtg         48
Gln Leu Val Gln Ser Gly Ala Glu Val Lys Lys Pro Glu Ser Ser Val
1               5                   10                  15 aag gtc tcc tgc aag gct tct gga ggc acc ctc acc aac tat gct atc         96
Lys Val Ser Cys Lys Ala Ser Gly Gly Thr Leu Thr Asn Tyr Ala Ile
            20                  25                  30 acc tgg gtg cga cag gcc cct gga caa ggg ctt gag tgg atg gga agg        144
Thr Trp Val Arg Gln Ala Pro Gly Gln Gly Leu Glu Trp Met Gly Arg
```

```
                         35                  40                  45
atc atc cct atg att cat atg aca aat tac gca cag aag ttc cag ggc        192
Ile Ile Pro Met Ile His Met Thr Asn Tyr Ala Gln Lys Phe Gln Gly
 50                  55                  60 aga gtc acg att acc gcg gac aat tcc acg aga aca gcc tac atg gag        240
Arg Val Thr Ile Thr Ala Asp Asn Ser Thr Arg Thr Ala Tyr Met Glu
 65                  70                  75                  80 gtg aag agt ctc aga tct gac gac acg gcc gta tat tat tgt gcg aga        288
Val Lys Ser Leu Arg Ser Asp Asp Thr Ala Val Tyr Tyr Cys Ala Arg
                 85                  90                  95 gat ttt ttc ggt tcg ggg agt tac tat tcc ggt ctg gac gtc tgg ggc        336
Asp Phe Phe Gly Ser Gly Ser Tyr Tyr Ser Gly Leu Asp Val Trp Gly
            100                 105                 110 caa ggg acc acg gtc acc gtc tcc tca                                    363
Gln Gly Thr Thr Val Thr Val Ser Ser
            115                 120

<210> SEQ ID NO 61
<211> LENGTH: 121
<212> TYPE: PRT
<213> ORGANISM: Homo sapiens

<400> SEQUENCE: 61

Gln Leu Val Gln Ser Gly Ala Glu Val Lys Lys Pro Glu Ser Val
 1               5                  10                  15

Lys Val Ser Cys Lys Ala Ser Gly Gly Thr Leu Thr Asn Tyr Ala Ile
             20                  25                  30

Thr Trp Val Arg Gln Ala Pro Gly Gln Gly Leu Glu Trp Met Gly Arg
         35                  40                  45

Ile Ile Pro Met Ile His Met Thr Asn Tyr Ala Gln Lys Phe Gln Gly
 50                  55                  60

Arg Val Thr Ile Thr Ala Asp Asn Ser Thr Arg Thr Ala Tyr Met Glu
 65                  70                  75                  80

Val Lys Ser Leu Arg Ser Asp Asp Thr Ala Val Tyr Tyr Cys Ala Arg
                 85                  90                  95

Asp Phe Phe Gly Ser Gly Ser Tyr Tyr Ser Gly Leu Asp Val Trp Gly
            100                 105                 110

Gln Gly Thr Thr Val Thr Val Ser Ser
            115                 120

<210> SEQ ID NO 62
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 62 cag gtc cag ctg gta cag tct gga gca gag gtg gaa aag ccc ggg gag         48
Gln Val Gln Leu Val Gln Ser Gly Ala Glu Val Glu Lys Pro Gly Glu
 1               5                  10                  15 tct ctg aag atc tcc tgt aag ggt tct gga tac agc ttt acc agc aac         96
Ser Leu Lys Ile Ser Cys Lys Gly Ser Gly Tyr Ser Phe Thr Ser Asn
             20                  25                  30 tgg atc ggc tgg gtg cgc cag atg ccc ggg aaa ggc ctg gag tgg atg        144
Trp Ile Gly Trp Val Arg Gln Met Pro Gly Lys Gly Leu Glu Trp Met
         35                  40                  45 ggg atg atc tat cct ggt gac tct gac acc atg tac agt cag tcc ttc        192
Gly Met Ile Tyr Pro Gly Asp Ser Asp Thr Met Tyr Ser Gln Ser Phe
 50                  55                  60
```

```
aaa ggc cag gtc acc ctc tca gtc gac aag tcc gtc agc acc gcc tgc        240
Lys Gly Gln Val Thr Leu Ser Val Asp Lys Ser Val Ser Thr Ala Cys
 65                  70                  75                  80 ctt cag tgg agc agc ctg cag gcc tcg gac act gcc ctg tat tac tgt        288
Leu Gln Trp Ser Ser Leu Gln Ala Ser Asp Thr Ala Leu Tyr Tyr Cys
                 85                  90                  95 gcg aga gtc cct aac tta agc agt gcc tgg cac tct ttt gac tac tgg        336
Ala Arg Val Pro Asn Leu Ser Ser Ala Trp His Ser Phe Asp Tyr Trp
            100                 105                 110 ggc cag gga acc ctg gtc acc gtc tcc tca                                366
Gly Gln Gly Thr Leu Val Thr Val Ser Ser
            115                 120

<210> SEQ ID NO 63
<211> LENGTH: 122
<212> TYPE: PRT
<213> ORGANISM: Homo sapiens

<400> SEQUENCE: 63

Gln Val Gln Leu Val Gln Ser Gly Ala Glu Val Glu Lys Pro Gly Glu
  1               5                  10                  15

Ser Leu Lys Ile Ser Cys Lys Gly Ser Gly Tyr Ser Phe Thr Ser Asn
                 20                  25                  30

Trp Ile Gly Trp Val Arg Gln Met Pro Gly Lys Gly Leu Glu Trp Met
             35                  40                  45

Gly Met Ile Tyr Pro Gly Asp Ser Asp Thr Met Tyr Ser Gln Ser Phe
         50                  55                  60

Lys Gly Gln Val Thr Leu Ser Val Asp Lys Ser Val Ser Thr Ala Cys
 65                  70                  75                  80

Leu Gln Trp Ser Ser Leu Gln Ala Ser Asp Thr Ala Leu Tyr Tyr Cys
                 85                  90                  95

Ala Arg Val Pro Asn Leu Ser Ser Ala Trp His Ser Phe Asp Tyr Trp
            100                 105                 110

Gly Gln Gly Thr Leu Val Thr Val Ser Ser
            115                 120

<210> SEQ ID NO 64
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 64 cag gtc cag ctt gtg cag tct ggg gga gac ttg gtt cag cct ggg ggg         48
Gln Val Gln Leu Val Gln Ser Gly Gly Asp Leu Val Gln Pro Gly Gly
  1               5                  10                  15 tcc ctc aga ctc tcc tgt gca gcc tct gga ttc acc ttt gat gaa tat         96
Ser Leu Arg Leu Ser Cys Ala Ala Ser Gly Phe Thr Phe Asp Glu Tyr
                 20                  25                  30 ggc atg cac tgg gtc cgt cag gct cca ggg aag ggt ctg gag tgg gtc        144
Gly Met His Trp Val Arg Gln Ala Pro Gly Lys Gly Leu Glu Trp Val
             35                  40                  45 tct ctt att agt ggg gat ggc gat tac aca tcc tat gct gac tct gtg        192
Ser Leu Ile Ser Gly Asp Gly Asp Tyr Thr Ser Tyr Ala Asp Ser Val
         50                  55                  60 aag ggc cga ttc acc atc tcc aga gac aac aat aaa aac tcc ctg tat        240
Lys Gly Arg Phe Thr Ile Ser Arg Asp Asn Asn Lys Asn Ser Leu Tyr
 65                  70                  75                  80
```

```
ctg caa atg aac agt ctg aga act gag gac acc gcc ttg tat tac tgt      288
Leu Gln Met Asn Ser Leu Arg Thr Glu Asp Thr Ala Leu Tyr Tyr Cys
                85                  90                  95 gca aaa gat ggg tac ccc tat ggc agg gac ttc tac tac tac tac atg      336
Ala Lys Asp Gly Tyr Pro Tyr Gly Arg Asp Phe Tyr Tyr Tyr Tyr Met
            100                 105                 110 gac gtc tgg ggc aaa ggg acc acg gtc acc gtc tcc tca                  375
Asp Val Trp Gly Lys Gly Thr Thr Val Thr Val Ser Ser
        115                 120                 125

<210> SEQ ID NO 65
<211> LENGTH: 125
<212> TYPE: PRT
<213> ORGANISM: Homo sapiens

<400> SEQUENCE: 65

Gln Val Gln Leu Val Gln Ser Gly Gly Asp Leu Val Gln Pro Gly Gly
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ser Leu Ile Ser Gly Asp Gly Asp Tyr Thr Ser Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Gly Tyr Pro Tyr Gly Arg Asp Phe Tyr Tyr Tyr Tyr Met
            100                 105                 110

Asp Val Trp Gly Lys Gly Thr Thr Val Thr Val Ser Ser
        115                 120                 125

<210> SEQ ID NO 66
<211> LENGTH: 390
<212> TYPE: DNA
<213> ORGANISM: Homo sapiens
<220> FEATURE:
<221> NAME/KEY: CDS
<222> LOCATION: (1)..(390)

<400> SEQUENCE: 66 cag gtt cag ctg gtg cag tct ggg gga ggc ttg gta caa cct ggg ggg      48
Gln Val Gln Leu Val Gln Ser Gly Gly Gly Leu Val Gln Pro Gly Gly
1               5                   10                  15 tcc ctg aga ctc tcc tgt gca acc tct ggg ttc acc ttt agg agc tat      96
Ser Leu Arg Leu Ser Cys Ala Thr Ser Gly Phe Thr Phe Arg Ser Tyr
            20                  25                  30 gac atg act tgg gtc cgc cag gct cca ggg aag ggg ctg gaa tgg gtc      144
Asp Met Thr Trp Val Arg Gln Ala Pro Gly Lys Gly Leu Glu Trp Val
        35                  40                  45 tca act atc agt ggg agt ggt ggt aga aca cac tac aca gac tcc gtg      192
Ser Thr Ile Ser Gly Ser Gly Gly Arg Thr His Tyr Thr Asp Ser Val
    50                  55                  60 aag ggc cgg ttc acc atc acc aga gac aat tcc aag agc acg ctg ttt      240
Lys Gly Arg Phe Thr Ile Thr Arg Asp Asn Ser Lys Ser Thr Leu Phe
65                  70                  75                  80 ctg caa atg aac ggc ctg aga gcc gag gac acg gcc gta tat tac tgt      288
Leu Gln Met Asn Gly Leu Arg Ala Glu Asp Thr Ala Val Tyr Tyr Cys
                85                  90                  95 gcg aaa ggg ggc tta act gcc agt ata gcg gta gtt ggt caa ctg tac      336
```

```
Ala Lys Gly Gly Leu Thr Ala Ser Ile Ala Val Val Gly Gln Leu Tyr
            100                 105                 110 gac tac cac gga atg gac gtc tgg ggc caa ggg acc acg gtc acc gtc    384
Asp Tyr His Gly Met Asp Val Trp Gly Gln Gly Thr Thr Val Thr Val
            115                 120                 125 tcc tca                                                             390
Ser Ser
    130

<210> SEQ ID NO 67
<211> LENGTH: 130
<212> TYPE: PRT
<213> ORGANISM: Homo sapiens

<400> SEQUENCE: 67

Gln Val Gln Leu Val Gln Ser Gly Gly Gly Leu Val Gln Pro Gly Gly
1               5                  10                  15

Ser Leu Arg Leu Ser Cys Ala Thr Ser Gly Phe Thr Phe Arg Ser Tyr
            20                  25                  30

Asp Met Thr Trp Val Arg Gln Ala Pro Gly Lys Gly Leu Glu Trp Val
        35                  40                  45

Ser Thr Ile Ser Gly Ser Gly Gly Arg Thr His Tyr Thr Asp Ser Val
    50                  55                  60

Lys Gly Arg Phe Thr Ile Thr Arg Asp Asn Ser Lys Ser Thr Leu Phe
65                  70                  75                  80

Leu Gln Met Asn Gly Leu Arg Ala Glu Asp Thr Ala Val Tyr Tyr Cys
                85                  90                  95

Ala Lys Gly Gly Leu Thr Ala Ser Ile Ala Val Val Gly Gln Leu Tyr
            100                 105                 110

Asp Tyr His Gly Met Asp Val Trp Gly Gln Gly Thr Thr Val Thr Val
            115                 120                 125

Ser Ser
    130

<210> SEQ ID NO 68
<211> LENGTH: 91
<212> TYPE: DNA
<213> ORGANISM: Artificial
<220> FEATURE:
<223> OTHER INFORMATION: An artificially synthesized template linker
      sequence

<400> SEQUENCE: 68
ggacaatggt caccgtctct tcaggtggtg gtggttcggg tggtggtggt tcgggtggtg     60
gcggatcgga catccagatg acccagtctc c                                   91

<210> SEQ ID NO 69
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 69
gcaccctggt caccgtctcc tcaggtgg                                       28

<210> SEQ ID NO 70
<211> LENGTH: 28
<212> TYPE: DNA
<213> ORGANISM: Artificial
<220> FEATURE:
<223> OTHER INFORMATION: An artificially synthesized primer sequence
```

```
<400> SEQUENCE: 70
ggacaatggt caccgtctct tcaggtgg                                              28

<210> SEQ ID NO 71
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 71
gaaccctggt caccgtctcc tcaggtgg                                              28

<210> SEQ ID NO 72
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 72
ggaccacggt caccgtctcc tcaggtgg                                              28

<210> SEQ ID NO 73
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 73
ggagactggg tcatctggat gtccgatccg cc                                         32

<210> SEQ ID NO 74
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 74
ggagactgag tcatcacaac atccgatccg cc                                         32

<210> SEQ ID NO 75
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 75
ggagactgcg tcaacacaat ttccgatccg cc                                         32

<210> SEQ ID NO 76
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 76
ggagactggg tcatcacgat gtccgatccg cc                                         32

<210> SEQ ID NO 77
<211> LENGTH: 32
```

```
<212> TYPE: DNA
<213> ORGANISM: Artificial
<220> FEATURE:
<223> OTHER INFORMATION: An artificially synthesized primer sequence

<400> SEQUENCE: 77
ggagactgcg tgagtgtcgt ttccgatccg cc                                   32

<210> SEQ ID NO 78
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 78
ggagactgag tcagcacaat ttccgatccg cc                                   32

<210> SEQ ID NO 79
<211> LENGTH: 42
<212> TYPE: DNA
<213> ORGANISM: Artificial
<220> FEATURE:
<223> OTHER INFORMATION: An artificially synthesized primer sequence

<400> SEQUENCE: 79
ggcggctgcg tcaacacaga ctgcgatccg ccaccgccag ag                        42

<210> SEQ ID NO 80
<211> LENGTH: 42
<212> TYPE: DNA
<213> ORGANISM: Artificial
<220> FEATURE:
<223> OTHER INFORMATION: An artificially synthesized primer sequence

<400> SEQUENCE: 80
gcaggctgag tcagagcaga ctgcgatccg ccaccgccag ag                        42

<210> SEQ ID NO 81
<211> LENGTH: 42
<212> TYPE: DNA
<213> ORGANISM: Artificial
<220> FEATURE:
<223> OTHER INFORMATION: An artificially synthesized primer sequence

<400> SEQUENCE: 81
ggtggctgag tcagcacata ggacgatccg ccaccgccag ag                        42

<210> SEQ ID NO 82
<211> LENGTH: 42
<212> TYPE: DNA
<213> ORGANISM: Artificial
<220> FEATURE:
<223> OTHER INFORMATION: An artificially synthesized primer sequence

<400> SEQUENCE: 82
gggtcctgag tcagctcaga agacgatccg ccaccgccag ag                        42

<210> SEQ ID NO 83
<211> LENGTH: 42
<212> TYPE: DNA
<213> ORGANISM: Artificial
<220> FEATURE:
<223> OTHER INFORMATION: An artificially synthesized primer sequence

<400> SEQUENCE: 83
ggcggttgag tcagtataac gtgcgatccg ccaccgccag ag                        42
```

<210> SEQ ID NO 84
<211> LENGTH: 42
<212> TYPE: DNA
<213> ORGANISM: Artificial
<220> FEATURE:
<223> OTHER INFORMATION: An artificially synthesized primer sequence

<400> SEQUENCE: 84
gacggctgag tcagcacaga ctgcgatccg ccaccgccag ag                           42

<210> SEQ ID NO 85
<211> LENGTH: 42
<212> TYPE: DNA
<213> ORGANISM: Artificial
<220> FEATURE:
<223> OTHER INFORMATION: An artificially synthesized primer sequence

<400> SEQUENCE: 85
tggggctgag tcagcataaa attcgatccg ccaccgccag ag                           42

<210> SEQ ID NO 86
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 86
gtcctcgcaa ctgcggccca gccggccatg gcccaggtgc agctggtgca gtctgg           56

<210> SEQ ID NO 87
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 87
gtcctcgcaa ctgcggccca gccggccatg gcccaggtca acttaaggga gtctgg           56

<210> SEQ ID NO 88
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 88
gtcctcgcaa ctgcggccca gccggccatg gccgaggtgc agctggtgga gtctgg           56

<210> SEQ ID NO 89
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 89
gtcctcgcaa ctgcggccca gccggccatg gcccaggtgc agctgcagga gtcggg           56

<210> SEQ ID NO 90
<211> LENGTH: 56
<212> TYPE: DNA
<213> ORGANISM: Artificial
<220> FEATURE:
<223> OTHER INFORMATION: An artificially synthesized primer sequence

```
<400> SEQUENCE: 90
gtcctcgcaa ctgcggccca gccggccatg gcccaggtgc agctgttgca gtctgc        56

<210> SEQ ID NO 91
<211> LENGTH: 56
<212> TYPE: DNA
<213> ORGANISM: Artificial
<220> FEATURE:
<223> OTHER INFORMATION: An artificially synthesized primer sequence

<400> SEQUENCE: 91
gtcctcgcaa ctgcggccca gccggccatg gcccaggtac agctgcagca gtcagg        56

<210> SEQ ID NO 92
<211> LENGTH: 48
<212> TYPE: DNA
<213> ORGANISM: Artificial
<220> FEATURE:
<223> OTHER INFORMATION: An artificially synthesized primer sequence

<400> SEQUENCE: 92
gagtcattct cgacttgcgg ccgcacgttt gatttccacc ttggtccc                 48

<210> SEQ ID NO 93
<211> LENGTH: 48
<212> TYPE: DNA
<213> ORGANISM: Artificial
<220> FEATURE:
<223> OTHER INFORMATION: An artificially synthesized primer sequence

<400> SEQUENCE: 93
gagtcattct cgacttgcgg ccgcacgttt gatctccagc ttggtccc                 48

<210> SEQ ID NO 94
<211> LENGTH: 48
<212> TYPE: DNA
<213> ORGANISM: Artificial
<220> FEATURE:
<223> OTHER INFORMATION: An artificially synthesized primer sequence

<400> SEQUENCE: 94
gagtcattct cgacttgcgg ccgcacgttt gatatccact ttggtccc                 48

<210> SEQ ID NO 95
<211> LENGTH: 48
<212> TYPE: DNA
<213> ORGANISM: Artificial
<220> FEATURE:
<223> OTHER INFORMATION: An artificially synthesized primer sequence

<400> SEQUENCE: 95
gagtcattct cgacttgcgg ccgcacgttt gatctccacc ttggtccc                 48

<210> SEQ ID NO 96
<211> LENGTH: 48
<212> TYPE: DNA
<213> ORGANISM: Artificial
<220> FEATURE:
<223> OTHER INFORMATION: An artificially synthesized primer sequence

<400> SEQUENCE: 96
gagtcattct cgacttgcgg ccgcacgttt aatctccagt cgtgtccc                 48

<210> SEQ ID NO 97
<211> LENGTH: 48
```

<210> SEQ ID NO 97
<211> LENGTH: 48
<212> TYPE: DNA
<213> ORGANISM: Artificial
<220> FEATURE:
<223> OTHER INFORMATION: An artificially synthesized primer sequence

<400> SEQUENCE: 97
gagtcattct cgacttgcgg ccgcacctag gacggtgacc ttggtccc         48

<210> SEQ ID NO 98
<211> LENGTH: 48
<212> TYPE: DNA
<213> ORGANISM: Artificial
<220> FEATURE:
<223> OTHER INFORMATION: An artificially synthesized primer sequence

<400> SEQUENCE: 98
gagtcattct cgacttgcgg ccgcacctag gacggtcagc ttggtccc         48

<210> SEQ ID NO 99
<211> LENGTH: 48
<212> TYPE: DNA
<213> ORGANISM: Artificial
<220> FEATURE:
<223> OTHER INFORMATION: An artificially synthesized primer sequence

<400> SEQUENCE: 99
gagtcattct cgacttgcgg ccgcacctaa aacggtgagc tgggtccc         48

<210> SEQ ID NO 100
<211> LENGTH: 782
<212> TYPE: DNA
<213> ORGANISM: Artificial
<220> FEATURE:
<223> OTHER INFORMATION: An artificially synthesized scFv sequence
<220> FEATURE:
<221> NAME/KEY: CDS
<222> LOCATION: (1)..(780)

<400> SEQUENCE: 100

| gcg | gcc | cag | ccg | gcc | atg | gcc | gag | gtg | cag | ctg | gtg | gag | tct | ggg | cct | 48 |
| Ala | Ala | Gln | Pro | Ala | Met | Ala | Glu | Val | Gln | Leu | Val | Glu | Ser | Gly | Pro | |
| 1   |     |     |     | 5   |     |     |     |     | 10  |     |     |     |     | 15  |     | |

| gag | gtg | aag | aag | cct | ggg | acc | tca | gtg | aag | gtc | tcc | tgc | aag | gct | tct | 96 |
| Glu | Val | Lys | Lys | Pro | Gly | Thr | Ser | Val | Lys | Val | Ser | Cys | Lys | Ala | Ser | |
|     |     | 20  |     |     |     |     | 25  |     |     |     |     | 30  |     |     |     | |

| gga | ttc | acc | ttc | act | agc | tct | cta | cag | tgg | gtg | cga | cag | gcc | cgt | | 144 |
| Gly | Phe | Thr | Phe | Thr | Ser | Ser | Leu | Gln | Trp | Val | Arg | Gln | Ala | Arg | | |
|     |     | 35  |     |     |     |     | 40  |     |     |     |     | 45  |     |     | | |

| ggc | cga | cgc | ctt | gag | ttt | ata | gga | cgg | ctc | gtc | ctt | ggc | agt | gga | aag | 192 |
| Gly | Arg | Arg | Leu | Glu | Phe | Ile | Gly | Arg | Leu | Val | Leu | Gly | Ser | Gly | Lys | |
| 50  |     |     |     |     | 55  |     |     |     |     | 60  |     |     |     |     |     | |

| aca | aac | tac | gca | cag | aat | ttc | cac | gaa | aga | gtc | acc | att | aac | agg | gac | 240 |
| Thr | Asn | Tyr | Ala | Gln | Asn | Phe | His | Glu | Arg | Val | Thr | Ile | Asn | Arg | Asp | |
| 65  |     |     |     | 70  |     |     |     |     | 75  |     |     |     |     | 80  |     | |

| atg | tcc | aca | agc | aca | gcc | tac | atg | gag | ctg | acc | ggc | ctg | aga | tcc | gaa | 288 |
| Met | Ser | Thr | Ser | Thr | Ala | Tyr | Met | Glu | Leu | Thr | Gly | Leu | Arg | Ser | Glu | |
|     |     |     | 85  |     |     |     |     | 90  |     |     |     |     | 95  |     |     | |

| gac | acg | gcc | gtg | tat | tat | tgt | gcc | gta | gat | tgg | gtt | agc | tac | ggt | gac | 336 |
| Asp | Thr | Ala | Val | Tyr | Tyr | Cys | Ala | Val | Asp | Trp | Val | Ser | Tyr | Gly | Asp | |
|     | 100 |     |     |     |     | 105 |     |     |     |     | 110 |     |     |     |     | |

| tac | gtt | cac | agt | cgg | gtc | ggt | ttt | gat | atc | tgg | ggc | caa | ggg | aca | atg | 384 |
| Tyr | Val | His | Ser | Arg | Val | Gly | Phe | Asp | Ile | Trp | Gly | Gln | Gly | Thr | Met | |
|     |     | 115 |     |     |     |     | 120 |     |     |     |     | 125 |     |     |     | |

| gtc | acc | gtc | tct | tca | ggt | ggt | ggt | ggt | tcg | ggt | ggt | ggt | ggt | tcg | ggt | 432 |
| Val | Thr | Val | Ser | Ser | Gly | Gly | Gly | Gly | Ser | Gly | Gly | Gly | Gly | Ser | Gly | |

```
                130                 135                 140
ggt ggc gga tcg gac atc gtg atg acc cag tct cca gac tcc ctg gct    480
Gly Gly Gly Ser Asp Ile Val Met Thr Gln Ser Pro Asp Ser Leu Ala
145                 150                 155                 160 gtg tct ctg ggc gag agg gcc acc atc acc tgc agg gcc agt cag agt    528
Val Ser Leu Gly Glu Arg Ala Thr Ile Thr Cys Arg Ala Ser Gln Ser
                165                 170                 175 gtt agc agc agc tac tta gcc tgg tac cag cag aag cct ggc cag gct    576
Val Ser Ser Ser Tyr Leu Ala Trp Tyr Gln Gln Lys Pro Gly Gln Ala
            180                 185                 190 ccc agg ctc ctc atc tat gct gcg tcc agc agg gcc act ggc atc cca    624
Pro Arg Leu Leu Ile Tyr Ala Ala Ser Ser Arg Ala Thr Gly Ile Pro
        195                 200                 205 gac agg ttc agt ggc agt ggg cct ggg acg gac ttc act ctc acc atc    672
Asp Arg Phe Ser Gly Ser Gly Pro Gly Thr Asp Phe Thr Leu Thr Ile
    210                 215                 220 agc aga ctg gag cct gaa gat ttt gca gta tat tat tgt cag cag tat    720
Ser Arg Leu Glu Pro Glu Asp Phe Ala Val Tyr Tyr Cys Gln Gln Tyr
225                 230                 235                 240 ggt aac tca ccc tta ttc act ttc ggc cct ggg acc aaa gtg gat atc    768
Gly Asn Ser Pro Leu Phe Thr Phe Gly Pro Gly Thr Lys Val Asp Ile
                245                 250                 255 aaa cgt gcg gcc gc                                                 782
Lys Arg Ala Ala
        260

<210> SEQ ID NO 101
<211> LENGTH: 260
<212> TYPE: PRT
<213> ORGANISM: Artificial
<220> FEATURE:
<223> OTHER INFORMATION: Synthetic Construct

<400> SEQUENCE: 101

Ala Ala Gln Pro Ala Met Ala Glu Val Gln Leu Val Glu Ser Gly Pro
1               5                   10                  15

Glu Val Lys Lys Pro Gly Thr Ser Val Lys Val Ser Cys Lys Ala Ser
                20                  25                  30

Gly Phe Thr Phe Thr Ser Ser Leu Gln Trp Val Arg Gln Ala Arg
            35                  40                  45

Gly Arg Arg Leu Glu Phe Ile Gly Arg Leu Val Leu Gly Ser Gly Lys
        50                  55                  60

Thr Asn Tyr Ala Gln Asn Phe His Glu Arg Val Thr Ile Asn Arg Asp
65                  70                  75                  80

Met Ser Thr Ser Thr Ala Tyr Met Glu Leu Thr Gly Leu Arg Ser Glu
                85                  90                  95

Asp Thr Ala Val Tyr Tyr Cys Ala Val Asp Trp Val Ser Tyr Gly Asp
                100                 105                 110

Tyr Val His Ser Arg Val Gly Phe Asp Ile Trp Gly Gln Gly Thr Met
            115                 120                 125

Val Thr Val Ser Gly Gly Gly Gly Ser Gly Gly Gly Gly Ser Gly
        130                 135                 140

Gly Gly Gly Ser Asp Ile Val Met Thr Gln Ser Pro Asp Ser Leu Ala
145                 150                 155                 160

Val Ser Leu Gly Glu Arg Ala Thr Ile Thr Cys Arg Ala Ser Gln Ser
                165                 170                 175

Val Ser Ser Ser Tyr Leu Ala Trp Tyr Gln Gln Lys Pro Gly Gln Ala
            180                 185                 190
```

```
Pro Arg Leu Leu Ile Tyr Ala Ala Ser Ser Arg Ala Thr Gly Ile Pro
        195                 200                 205

Asp Arg Phe Ser Gly Ser Gly Pro Gly Thr Asp Phe Thr Leu Thr Ile
        210                 215                 220

Ser Arg Leu Glu Pro Glu Asp Phe Ala Val Tyr Tyr Cys Gln Gln Tyr
225                 230                 235                 240

Gly Asn Ser Pro Leu Phe Thr Phe Gly Pro Gly Thr Lys Val Asp Ile
                245                 250                 255

Lys Arg Ala Ala
        260

<210> SEQ ID NO 102
<211> LENGTH: 767
<212> TYPE: DNA
<213> ORGANISM: Artificial
<220> FEATURE:
<223> OTHER INFORMATION: An artificially synthesized scFv sequence
<220> FEATURE:
<221> NAME/KEY: CDS
<222> LOCATION: (1)..(765)

<400> SEQUENCE: 102 gcg gcc cag ccg gcc atg gcc cag gtg cag ctg cag gag tcg gga gca      48
Ala Ala Gln Pro Ala Met Ala Gln Val Gln Leu Gln Glu Ser Gly Ala
1               5                   10                  15 gag gtg aaa aag ccc ggg gag tct ctg aag atc tcc tgt aag ggt tct      96
Glu Val Lys Lys Pro Gly Glu Ser Leu Lys Ile Ser Cys Lys Gly Ser
            20                  25                  30 gga tac agc ttt acc agc aac tgg atc ggc tgg gtg cgc cag atg ccc     144
Gly Tyr Ser Phe Thr Ser Asn Trp Ile Gly Trp Val Arg Gln Met Pro
        35                  40                  45 ggg aaa ggc ctg gag tgg atg ggg atg atc tat cct ggt gac tct gac     192
Gly Lys Gly Leu Glu Trp Met Gly Met Ile Tyr Pro Gly Asp Ser Asp
    50                  55                  60 acc atg tac agt cag tcc ttc aaa ggc cag gtc acc ctc tca gtc gac     240
Thr Met Tyr Ser Gln Ser Phe Lys Gly Gln Val Thr Leu Ser Val Asp
65                  70                  75                  80 aag tcc gtc agc acc gcc tac ctt cag tgg agc agc ctg cag gcc tcg     288
Lys Ser Val Ser Thr Ala Tyr Leu Gln Trp Ser Ser Leu Gln Ala Ser
                85                  90                  95 gac act gcc ctg tat tac tgt gcg aga gtc cct aac tta agc agt gcc     336
Asp Thr Ala Leu Tyr Tyr Cys Ala Arg Val Pro Asn Leu Ser Ser Ala
            100                 105                 110 tgg cac tct ttt gac tac tgg ggc cag ggc acc ctg gtc acc gtc tcc     384
Trp His Ser Phe Asp Tyr Trp Gly Gln Gly Thr Leu Val Thr Val Ser
        115                 120                 125 tca ggt ggt ggt ggt tcg ggt ggt ggt ggt tcg ggt ggt ggc gga tcg     432
Ser Gly Gly Gly Gly Ser Gly Gly Gly Gly Ser Gly Gly Gly Gly Ser
    130                 135                 140 gac atc cag atg acc cag tct cca ggc acc atg tcc ttg tct cca ggg     480
Asp Ile Gln Met Thr Gln Ser Pro Gly Thr Met Ser Leu Ser Pro Gly
145                 150                 155                 160 gaa aga gcc acc ctc tcc tgc agg gcc agt cag agt gtt agc acc acc     528
Glu Arg Ala Thr Leu Ser Cys Arg Ala Ser Gln Ser Val Ser Thr Thr
                165                 170                 175 tac tta gcc tgg tat cag cag aaa cct ggc cag gct ccc aga ctc ctc     576
Tyr Leu Ala Trp Tyr Gln Gln Lys Pro Gly Gln Ala Pro Arg Leu Leu
            180                 185                 190 atc tat ggt gca tcc agc agg gcc act ggc atc cca gac agg ttc agt     624
Ile Tyr Gly Ala Ser Ser Arg Ala Thr Gly Ile Pro Asp Arg Phe Ser
        195                 200                 205
```

```
ggc agt ggg tct ggg aca gac ttc act ctc acc atc aac aga ctg gag      672
Gly Ser Gly Ser Gly Thr Asp Phe Thr Leu Thr Ile Asn Arg Leu Glu
    210             215                 220 cct gaa gat ttt gca gtg tat tac tgt cag cac tat gtt agc tca cgg      720
Pro Glu Asp Phe Ala Val Tyr Tyr Cys Gln His Tyr Val Ser Ser Arg
225                 230                 235                 240 ctc act ttc ggc gga ggg acc aag ctg gag atc aaa cgt gcg gcc gc       767
Leu Thr Phe Gly Gly Gly Thr Lys Leu Glu Ile Lys Arg Ala Ala
                245                 250                 255
```

<210> SEQ ID NO 103
<211> LENGTH: 255
<212> TYPE: PRT
<213> ORGANISM: Artificial
<220> FEATURE:
<223> OTHER INFORMATION: Synthetic Construct

<400> SEQUENCE: 103

```
Ala Ala Gln Pro Ala Met Ala Gln Val Gln Leu Gln Glu Ser Gly Ala
1               5                   10                  15

Glu Val Lys Lys Pro Gly Glu Ser Leu Lys Ile Ser Cys Lys Gly Ser
            20                  25                  30

Gly Tyr Ser Phe Thr Ser Asn Trp Ile Gly Trp Val Arg Gln Met Pro
        35                  40                  45

Gly Lys Gly Leu Glu Trp Met Gly Met Ile Tyr Pro Gly Asp Ser Asp
    50                  55                  60

Thr Met Tyr Ser Gln Ser Phe Lys Gly Gln Val Thr Leu Ser Val Asp
65                  70                  75                  80

Lys Ser Val Ser Thr Ala Tyr Leu Gln Trp Ser Ser Leu Gln Ala Ser
                85                  90                  95

Asp Thr Ala Leu Tyr Tyr Cys Ala Arg Val Pro Asn Leu Ser Ser Ala
            100                 105                 110

Trp His Ser Phe Asp Tyr Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Asp Ile Gln Met Thr Gln Ser Pro Gly Thr Met Ser Leu Ser Pro Gly
145                 150                 155                 160

Glu Arg Ala Thr Leu Ser Cys Arg Ala Ser Gln Ser Val Ser Thr Thr
                165                 170                 175

Tyr Leu Ala Trp Tyr Gln Gln Lys Pro Gly Gln Ala Pro Arg Leu Leu
            180                 185                 190

Ile Tyr Gly Ala Ser Ser Arg Ala Thr Gly Ile Pro Asp Arg Phe Ser
        195                 200                 205

Gly Ser Gly Ser Gly Thr Asp Phe Thr Leu Thr Ile Asn Arg Leu Glu
    210                 215                 220

Pro Glu Asp Phe Ala Val Tyr Tyr Cys Gln His Tyr Val Ser Ser Arg
225                 230                 235                 240

Leu Thr Phe Gly Gly Gly Thr Lys Leu Glu Ile Lys Arg Ala Ala
                245                 250                 255
```

<210> SEQ ID NO 104
<211> LENGTH: 788
<212> TYPE: DNA
<213> ORGANISM: Artificial
<220> FEATURE:
<223> OTHER INFORMATION: An artificially synthesized scFv sequence
<220> FEATURE:
<221> NAME/KEY: CDS
<222> LOCATION: (1)..(786)

<400> SEQUENCE: 104

| | | | | | | | | | | | | | | | | |
|---|---|---|---|---|---|---|---|---|---|---|---|---|---|---|---|---|
| gcg | gcc | cag | ccg | gcc | atg | gcc | cag | gtg | cag | ctg | cag | gag | tcg | ggg | gga | 48 |
| Ala | Ala | Gln | Pro | Ala | Met | Ala | Gln | Val | Gln | Leu | Gln | Glu | Ser | Gly | Gly | |
| 1 | | | | 5 | | | | | 10 | | | | | 15 | | |
| gac | ttg | gtt | cag | cct | ggg | ggg | tcc | ctc | aga | ctc | tcc | tgt | gca | gcc | tct | 96 |
| Asp | Leu | Val | Gln | Pro | Gly | Gly | Ser | Leu | Arg | Leu | Ser | Cys | Ala | Ala | Ser | |
| | | | 20 | | | | | 25 | | | | | 30 | | | |
| gga | ttc | acc | ttt | gat | gaa | tat | ggc | atg | cac | tgg | gtc | cgt | cag | gct | cca | 144 |
| Gly | Phe | Thr | Phe | Asp | Glu | Tyr | Gly | Met | His | Trp | Val | Arg | Gln | Ala | Pro | |
| | | 35 | | | | | 40 | | | | | 45 | | | | |
| ggg | aag | ggt | ctg | gag | tgg | gtc | cct | ctt | att | agt | ggg | gat | ggc | gat | tac | 192 |
| Gly | Lys | Gly | Leu | Glu | Trp | Val | Pro | Leu | Ile | Ser | Gly | Asp | Gly | Asp | Tyr | |
| | 50 | | | | | 55 | | | | | 60 | | | | | |
| aca | tcc | tat | gct | gac | tct | gtg | aag | ggc | cga | ttc | acc | atc | tcc | aga | gac | 240 |
| Thr | Ser | Tyr | Ala | Asp | Ser | Val | Lys | Gly | Arg | Phe | Thr | Ile | Ser | Arg | Asp | |
| 65 | | | | | 70 | | | | | 75 | | | | | 80 | |
| aac | aat | aaa | aac | tcc | ctg | tat | ctg | caa | atg | aac | agt | ctg | aga | act | gag | 288 |
| Asn | Asn | Lys | Asn | Ser | Leu | Tyr | Leu | Gln | Met | Asn | Ser | Leu | Arg | Thr | Glu | |
| | | | | 85 | | | | | 90 | | | | | 95 | | |
| gac | acc | gcc | ttg | tat | tac | tgt | gca | aaa | gat | ggg | tac | ccc | tat | ggc | agg | 336 |
| Asp | Thr | Ala | Leu | Tyr | Tyr | Cys | Ala | Lys | Asp | Gly | Tyr | Pro | Tyr | Gly | Arg | |
| | | | 100 | | | | | 105 | | | | | 110 | | | |
| gac | ttc | tac | tac | tac | tac | atg | gac | gtc | tgg | ggc | aaa | ggg | acc | acg | gtc | 384 |
| Asp | Phe | Tyr | Tyr | Tyr | Tyr | Met | Asp | Val | Trp | Gly | Lys | Gly | Thr | Thr | Val | |
| | | 115 | | | | | 120 | | | | | 125 | | | | |
| acc | gtc | tcc | tca | ggt | ggt | ggt | ggt | tcg | ggt | ggt | ggt | ggc | tct | ggc | ggt | 432 |
| Thr | Val | Ser | Ser | Gly | Gly | Gly | Gly | Ser | Gly | Gly | Gly | Gly | Ser | Gly | Gly | |
| | 130 | | | | | 135 | | | | | 140 | | | | | |
| ggc | gga | tcg | cag | tct | gct | ctg | act | cag | cca | cct | tca | gcg | tct | ggg | acc | 480 |
| Gly | Gly | Ser | Gln | Ser | Ala | Leu | Thr | Gln | Pro | Pro | Ser | Ala | Ser | Gly | Thr | |
| 145 | | | | | 150 | | | | | 155 | | | | | 160 | |
| ccc | ggg | cag | agg | gtc | acc | atc | tct | tgt | tct | gga | agc | agc | tcc | aac | atc | 528 |
| Pro | Gly | Gln | Arg | Val | Thr | Ile | Ser | Cys | Ser | Gly | Ser | Ser | Ser | Asn | Ile | |
| | | | 165 | | | | | 170 | | | | | 175 | | | |
| gaa | act | aat | tat | gta | tac | tgg | tac | cag | cag | ctc | ccg | gga | acg | gcc | ccc | 576 |
| Glu | Thr | Asn | Tyr | Val | Tyr | Trp | Tyr | Gln | Gln | Leu | Pro | Gly | Thr | Ala | Pro | |
| | | 180 | | | | | 185 | | | | | 190 | | | | |
| agg | ctc | ctc | atc | tct | atg | aat | aat | cac | cgg | ccc | tca | ggg | gtc | cct | gac | 624 |
| Arg | Leu | Leu | Ile | Ser | Met | Asn | Asn | His | Arg | Pro | Ser | Gly | Val | Pro | Asp | |
| | 195 | | | | | 200 | | | | | 205 | | | | | |
| cga | ttc | tct | ggc | tcc | aag | tct | ggc | acc | tca | gcc | tcc | ctg | gcc | atc | agt | 672 |
| Arg | Phe | Ser | Gly | Ser | Lys | Ser | Gly | Thr | Ser | Ala | Ser | Leu | Ala | Ile | Ser | |
| 210 | | | | | 215 | | | | | 220 | | | | | | |
| ggg | ctc | cgg | tcc | gag | gat | gag | gct | gat | tat | tac | tgt | gca | gca | tgg | gat | 720 |
| Gly | Leu | Arg | Ser | Glu | Asp | Glu | Ala | Asp | Tyr | Tyr | Cys | Ala | Ala | Trp | Asp | |
| 225 | | | | | 230 | | | | | 235 | | | | | 240 | |
| gac | ggc | ctg | agt | ggt | ctg | cgt | tgg | gtg | ttc | ggc | gga | ggg | acc | aag | ctg | 768 |
| Asp | Gly | Leu | Ser | Gly | Leu | Arg | Trp | Val | Phe | Gly | Gly | Gly | Thr | Lys | Leu | |
| | | | 245 | | | | | 250 | | | | | 255 | | | |
| acc | gtc | cta | ggt | gcg | gcc | gc | | | | | | | | | | 788 |
| Thr | Val | Leu | Gly | Ala | Ala | | | | | | | | | | | |
| | | | 260 | | | | | | | | | | | | | |

<210> SEQ ID NO 105
<211> LENGTH: 262
<212> TYPE: PRT
<213> ORGANISM: Artificial
<220> FEATURE:
<223> OTHER INFORMATION: Synthetic Construct

<400> SEQUENCE: 105

```
Ala Ala Gln Pro Ala Met Ala Gln Val Gln Leu Gln Glu Ser Gly Gly
1               5                   10                  15

Asp Leu Val Gln Pro Gly Gly Ser Leu Arg Leu Ser Cys Ala Ala Ser
            20                  25                  30

Gly Phe Thr Phe Asp Glu Tyr Gly Met His Trp Val Arg Gln Ala Pro
        35                  40                  45

Gly Lys Gly Leu Glu Trp Val Pro Leu Ile Ser Gly Asp Gly Asp Tyr
50                  55                  60

Thr Ser Tyr Ala Asp Ser Val Lys Gly Arg Phe Thr Ile Ser Arg Asp
65                  70                  75                  80

Asn Asn Lys Asn Ser Leu Tyr Leu Gln Met Asn Ser Leu Arg Thr Glu
                85                  90                  95

Asp Thr Ala Leu Tyr Tyr Cys Ala Lys Asp Gly Tyr Pro Tyr Gly Arg
            100                 105                 110

Asp Phe Tyr Tyr Tyr Met Asp Val Trp Gly Lys Gly Thr Thr Val
        115                 120                 125

Thr Val Ser Ser Gly Gly Gly Gly Ser Gly Gly Gly Gly Ser Gly Gly
    130                 135                 140

Gly Gly Ser Gln Ser Ala Leu Thr Gln Pro Pro Ser Ala Ser Gly Thr
145                 150                 155                 160

Pro Gly Gln Arg Val Thr Ile Ser Cys Ser Gly Ser Ser Ser Asn Ile
                165                 170                 175

Glu Thr Asn Tyr Val Tyr Trp Tyr Gln Gln Leu Pro Gly Thr Ala Pro
            180                 185                 190

Arg Leu Leu Ile Ser Met Asn Asn His Arg Pro Ser Gly Val Pro Asp
        195                 200                 205

Arg Phe Ser Gly Ser Lys Ser Gly Thr Ser Ala Ser Leu Ala Ile Ser
    210                 215                 220

Gly Leu Arg Ser Glu Asp Glu Ala Asp Tyr Tyr Cys Ala Ala Trp Asp
225                 230                 235                 240

Asp Gly Leu Ser Gly Leu Arg Trp Val Phe Gly Gly Gly Thr Lys Leu
                245                 250                 255

Thr Val Leu Gly Ala Ala
            260
```

<210> SEQ ID NO 106
<211> LENGTH: 788
<212> TYPE: DNA
<213> ORGANISM: Artificial
<220> FEATURE:
<223> OTHER INFORMATION: An artificially synthesized scFv sequence
<220> FEATURE:
<221> NAME/KEY: CDS
<222> LOCATION: (1)..(786)

<400> SEQUENCE: 106

```
gcg gcc cag ccg gcc atg gcc cag gtg cag ctg cag gag tcg ggg gga      48
Ala Ala Gln Pro Ala Met Ala Gln Val Gln Leu Gln Glu Ser Gly Gly
1               5                   10                  15 gac ttg gtt cag cct ggg ggg tcc ctc aga ctc tcc tgt gca gcc tct      96
Asp Leu Val Gln Pro Gly Gly Ser Leu Arg Leu Ser Cys Ala Ala Ser
            20                  25                  30 gga ttc acc ttt gat gaa tat ggc atg cac tgg gtc cgt cag gct cca     144
Gly Phe Thr Phe Asp Glu Tyr Gly Met His Trp Val Arg Gln Ala Pro
        35                  40                  45 ggg aag ggt ctg gag tgg gtc tct ctt att agt ggg gat ggc gat tac     192
Gly Lys Gly Leu Glu Trp Val Ser Leu Ile Ser Gly Asp Gly Asp Tyr
50                  55                  60
```

```
aca tcc tat gct gac tct gtg aag ggc cga ttc gcc atc tcc aga gac     240
Thr Ser Tyr Ala Asp Ser Val Lys Gly Arg Phe Ala Ile Ser Arg Asp
 65                  70                  75                  80 aac aat aaa aac tcc ctg tat ctg caa atg aac agt ctg aga act gag     288
Asn Asn Lys Asn Ser Leu Tyr Leu Gln Met Asn Ser Leu Arg Thr Glu
                 85                  90                  95 gac acc gcc ttg tat tac tgt gca aaa gat ggg tac ccc tat ggc agg     336
Asp Thr Ala Leu Tyr Tyr Cys Ala Lys Asp Gly Tyr Pro Tyr Gly Arg
            100                 105                 110 gac ttc tac tac tac tac atg gac gtc tgg ggc caa ggg acc acg gtc     384
Asp Phe Tyr Tyr Tyr Tyr Met Asp Val Trp Gly Gln Gly Thr Thr Val
        115                 120                 125 acc gtc tcc tca ggt ggt ggt ggt tcg ggt ggt ggt ggc tct ggc ggt     432
Thr Val Ser Ser Gly Gly Gly Gly Ser Gly Gly Gly Gly Ser Gly Gly
130                 135                 140 ggc aga tcg cag tct gtg ttg acg cag ccg ccc tca gcg tct ggg acc     480
Gly Arg Ser Gln Ser Val Leu Thr Gln Pro Pro Ser Ala Ser Gly Thr
145                 150                 155                 160 ccc ggg cag agg gtc acc atc tct tgt tct gga agc agc tcc aac atc     528
Pro Gly Gln Arg Val Thr Ile Ser Cys Ser Gly Ser Ser Ser Asn Ile
                165                 170                 175 gaa act aat tat gta tac tgg tac cag cag ctc ccg gga acg gcc ccc     576
Glu Thr Asn Tyr Val Tyr Trp Tyr Gln Gln Leu Pro Gly Thr Ala Pro
            180                 185                 190 aag ctc ctc atc tct atg aat aat cac cgg ccc tca ggg gtc cct gac     624
Lys Leu Leu Ile Ser Met Asn Asn His Arg Pro Ser Gly Val Pro Asp
        195                 200                 205 cga ttc tct ggc tcc aag tct ggc acc tca gcc tcc ctg gcc atc agt     672
Arg Phe Ser Gly Ser Lys Ser Gly Thr Ser Ala Ser Leu Ala Ile Ser
    210                 215                 220 ggg ctc cgg tcc gag gat gag gct gat tat tac tgt gca gca tgg gat     720
Gly Leu Arg Ser Glu Asp Glu Ala Asp Tyr Tyr Cys Ala Ala Trp Asp
225                 230                 235                 240 gac ggc ctg agt ggt ctg cgt tgg gtg ttc ggc gga ggg acc aag gtc     768
Asp Gly Leu Ser Gly Leu Arg Trp Val Phe Gly Gly Gly Thr Lys Val
                245                 250                 255 acc gtc cta ggt gcg gcc gc                                          788
Thr Val Leu Gly Ala Ala
            260

<210> SEQ ID NO 107
<211> LENGTH: 262
<212> TYPE: PRT
<213> ORGANISM: Artificial
<220> FEATURE:
<223> OTHER INFORMATION: Synthetic Construct

<400> SEQUENCE: 107

Ala Ala Gln Pro Ala Met Ala Gln Val Gln Leu Gln Glu Ser Gly Gly
 1               5                  10                  15

Asp Leu Val Gln Pro Gly Gly Ser Leu Arg Leu Ser Cys Ala Ala Ser
             20                  25                  30

Gly Phe Thr Phe Asp Glu Tyr Gly Met His Trp Val Arg Gln Ala Pro
         35                  40                  45

Gly Lys Gly Leu Glu Trp Val Ser Leu Ile Ser Gly Asp Gly Asp Tyr
     50                  55                  60

Thr Ser Tyr Ala Asp Ser Val Lys Gly Arg Phe Ala Ile Ser Arg Asp
 65                  70                  75                  80

Asn Asn Lys Asn Ser Leu Tyr Leu Gln Met Asn Ser Leu Arg Thr Glu
                 85                  90                  95
```

```
Asp Thr Ala Leu Tyr Tyr Cys Ala Lys Asp Gly Tyr Pro Tyr Gly Arg
            100                 105                 110

Asp Phe Tyr Tyr Tyr Met Asp Val Trp Gly Gln Gly Thr Thr Val
        115                 120                 125

Thr Val Ser Ser Gly Gly Gly Ser Gly Gly Gly Ser Gly Gly
130                 135                 140

Gly Arg Ser Gln Ser Val Leu Thr Gln Pro Pro Ser Ala Ser Gly Thr
145                 150                 155                 160

Pro Gly Gln Arg Val Thr Ile Ser Cys Ser Gly Ser Ser Ser Asn Ile
                165                 170                 175

Glu Thr Asn Tyr Val Tyr Trp Tyr Gln Gln Leu Pro Gly Thr Ala Pro
            180                 185                 190

Lys Leu Leu Ile Ser Met Asn Asn His Arg Pro Ser Gly Val Pro Asp
        195                 200                 205

Arg Phe Ser Gly Ser Lys Ser Gly Thr Ser Ala Ser Leu Ala Ile Ser
    210                 215                 220

Gly Leu Arg Ser Glu Asp Glu Ala Asp Tyr Tyr Cys Ala Ala Trp Asp
225                 230                 235                 240

Asp Gly Leu Ser Gly Leu Arg Trp Val Phe Gly Gly Thr Lys Val
                245                 250                 255

Thr Val Leu Gly Ala Ala
            260
```

<210> SEQ ID NO 108
<211> LENGTH: 803
<212> TYPE: DNA
<213> ORGANISM: Artificial
<220> FEATURE:
<223> OTHER INFORMATION: An artificially synthesized scFv sequence
<220> FEATURE:
<221> NAME/KEY: CDS
<222> LOCATION: (1)..(801)

<400> SEQUENCE: 108

```
gcg gcc cag ccg gcc atg gcc cag gta cag ctg cag cag tca ggg gga    48
Ala Ala Gln Pro Ala Met Ala Gln Val Gln Leu Gln Gln Ser Gly Gly
1               5                   10                  15 ggc ttg gta caa cct ggg ggg tcc ctg aga ctc tcc tgt gca acc tct    96
Gly Leu Val Gln Pro Gly Gly Ser Leu Arg Leu Ser Cys Ala Thr Ser
            20                  25                  30 ggg ttc acc ttt agg agc tat gac atg act tgg gtc cgc cag gct cca    144
Gly Phe Thr Phe Arg Ser Tyr Asp Met Thr Trp Val Arg Gln Ala Pro
        35                  40                  45 ggg aag ggg ctg gaa tgg gtc tca act atc agt ggg agt ggt ggt aga    192
Gly Lys Gly Leu Glu Trp Val Ser Thr Ile Ser Gly Ser Gly Gly Arg
    50                  55                  60 aca cac tac aca gac tcc gtg aag ggc cgg ttc acc atc acc aga gac    240
Thr His Tyr Thr Asp Ser Val Lys Gly Arg Phe Thr Ile Thr Arg Asp
65                  70                  75                  80 aat tcc aag agc acg ctg ttt ctg caa atg aac ggc ctg aga gcc gag    288
Asn Ser Lys Ser Thr Leu Phe Leu Gln Met Asn Gly Leu Arg Ala Glu
                85                  90                  95 gac acg gcc gta tat tac tgt gcg aaa ggg ggc tta act gcc agt ata    336
Asp Thr Ala Val Tyr Tyr Cys Ala Lys Gly Gly Leu Thr Ala Ser Ile
            100                 105                 110 gcg gta gtt ggt caa ctg tac gac tac cac gga atg gac gtc tgg ggc    384
Ala Val Val Gly Gln Leu Tyr Asp Tyr His Gly Met Asp Val Trp Gly
        115                 120                 125 caa ggg acc acg gtc acc gtc tcc tca ggt ggt ggt ggt tcg ggt ggt    432
```

```
                                                                                      480
ggt ggc tct ggc ggt ggc gga tcg tcc tat gtg ctg act cag ccg tct
Gly Gly Ser Gly Gly Gly Gly Ser Ser Tyr Val Leu Thr Gln Pro Ser
145             150                 155                 160

528
tca gcg tct ggg acc ccc ggg cag agg gtc acc atc tct tgt tct gga
Ser Ala Ser Gly Thr Pro Gly Gln Arg Val Thr Ile Ser Cys Ser Gly
                165                 170                 175

576
agc agc tcc aac atc gaa act aat tat gta tac tgg tac cag cag ctc
Ser Ser Ser Asn Ile Glu Thr Asn Tyr Val Tyr Trp Tyr Gln Gln Leu
            180                 185                 190

624
ccg gga acg gcc ccc aag ctc ctc atc tct acg aat aat cac cgg ccc
Pro Gly Thr Ala Pro Lys Leu Leu Ile Ser Thr Asn Asn His Arg Pro
        195                 200                 205

672
tca ggg gtc cct gac cga ttc tct ggc tcc aag tct ggc acc tca gcc
Ser Gly Val Pro Asp Arg Phe Ser Gly Ser Lys Ser Gly Thr Ser Ala
210                 215                 220

720
tcc ctg gcc atc agt ggg ctc cgg tcc gag gat gag gct gat tat tac
Ser Leu Ala Ile Ser Gly Leu Arg Ser Glu Asp Glu Ala Asp Tyr Tyr
225                 230                 235                 240

768
tgt gca gca tgg gat gac ggc ctg agt ggt ctg cgt tgg gtg ttc ggc
Cys Ala Ala Trp Asp Asp Gly Leu Ser Gly Leu Arg Trp Val Phe Gly
                245                 250                 255

803
gga ggg acc aag ctg acc gtc cta ggt gcg gcc gc
Gly Gly Thr Lys Leu Thr Val Leu Gly Ala Ala
                260                 265
```

<210> SEQ ID NO 109
<211> LENGTH: 267
<212> TYPE: PRT
<213> ORGANISM: Artificial
<220> FEATURE:
<223> OTHER INFORMATION: Synthetic Construct

<400> SEQUENCE: 109

```
Ala Ala Gln Pro Ala Met Ala Gln Val Gln Leu Gln Gln Ser Gly Gly
1               5                   10                  15

Gly Leu Val Gln Pro Gly Gly Ser Leu Arg Leu Ser Cys Ala Thr Ser
            20                  25                  30

Gly Phe Thr Phe Arg Ser Tyr Asp Met Thr Trp Val Arg Gln Ala Pro
        35                  40                  45

Gly Lys Gly Leu Glu Trp Val Ser Thr Ile Ser Gly Ser Gly Gly Arg
    50                  55                  60

Thr His Tyr Thr Asp Ser Val Lys Gly Arg Phe Thr Ile Thr Arg Asp
65                  70                  75                  80

Asn Ser Lys Ser Thr Leu Phe Leu Gln Met Asn Gly Leu Arg Ala Glu
                85                  90                  95

Asp Thr Ala Val Tyr Tyr Cys Ala Lys Gly Gly Leu Thr Ala Ser Ile
            100                 105                 110

Ala Val Val Gly Gln Leu Tyr Asp Tyr His Gly Met Asp Val Trp Gly
        115                 120                 125

Gln Gly Thr Thr Val Thr Val Ser Ser Gly Gly Gly Ser Gly Gly
    130                 135                 140

Gly Gly Ser Gly Gly Gly Ser Ser Tyr Val Leu Thr Gln Pro Ser
145                 150                 155                 160

Ser Ala Ser Gly Thr Pro Gly Gln Arg Val Thr Ile Ser Cys Ser Gly
                165                 170                 175

Ser Ser Ser Asn Ile Glu Thr Asn Tyr Val Tyr Trp Tyr Gln Gln Leu
            180                 185                 190
```

```
Pro Gly Thr Ala Pro Lys Leu Leu Ile Ser Thr Asn Asn His Arg Pro
            195                 200                 205

Ser Gly Val Pro Asp Arg Phe Ser Gly Ser Lys Ser Gly Thr Ser Ala
    210                 215                 220

Ser Leu Ala Ile Ser Gly Leu Arg Ser Glu Asp Glu Ala Asp Tyr Tyr
225                 230                 235                 240

Cys Ala Ala Trp Asp Asp Gly Leu Ser Gly Leu Arg Trp Val Phe Gly
                245                 250                 255

Gly Gly Thr Lys Leu Thr Val Leu Gly Ala Ala
            260                 265

<210> SEQ ID NO 110
<211> LENGTH: 803
<212> TYPE: DNA
<213> ORGANISM: Artificial
<220> FEATURE:
<223> OTHER INFORMATION: An artificially synthesized scFv sequence
<220> FEATURE:
<221> NAME/KEY: CDS
<222> LOCATION: (1)..(801)

<400> SEQUENCE: 110 gcg gcc cag ccg gcc atg gcc cag gta cag ctg cag cag tca ggg gga      48
Ala Ala Gln Pro Ala Met Ala Gln Val Gln Leu Gln Gln Ser Gly Gly
1               5                   10                  15 ggc ttg gta caa cct ggg ggg tcc ctg aga ctc tcc tgt gca acc tct      96
Gly Leu Val Gln Pro Gly Gly Ser Leu Arg Leu Ser Cys Ala Thr Ser
                20                  25                  30 ggg ttc acc ttt agg agc tat gac atg act tgg gtc cgc cag gct cca     144
Gly Phe Thr Phe Arg Ser Tyr Asp Met Thr Trp Val Arg Gln Ala Pro
            35                  40                  45 ggg aag ggg ctg gaa tgg gtc tca act atc agt ggg agt ggt ggt aga     192
Gly Lys Gly Leu Glu Trp Val Ser Thr Ile Ser Gly Ser Gly Gly Arg
        50                  55                  60 aca cac tac aca gac tcc gtg aag ggc cgg ttc acc atc acc aga gac     240
Thr His Tyr Thr Asp Ser Val Lys Gly Arg Phe Thr Ile Thr Arg Asp
65                  70                  75                  80 aat tcc aag agc acg ctg ttt ctg caa atg aac ggc ctg aga gcc gag     288
Asn Ser Lys Ser Thr Leu Phe Leu Gln Met Asn Gly Leu Arg Ala Glu
                85                  90                  95 gac acg gcc gta tat tac tgt gcg aaa ggg ggc tta act gcc agt ata     336
Asp Thr Ala Val Tyr Tyr Cys Ala Lys Gly Gly Leu Thr Ala Ser Ile
            100                 105                 110 gcg gta gtt ggt caa ctg tac gac tac cac gga atg gac gtc tgg ggc     384
Ala Val Val Gly Gln Leu Tyr Asp Tyr His Gly Met Asp Val Trp Gly
        115                 120                 125 caa ggg acc acg gtc acc gtc tcc tca ggt ggt ggt ggt tcg ggt ggt     432
Gln Gly Thr Thr Val Thr Val Ser Ser Gly Gly Gly Gly Ser Gly Gly
    130                 135                 140 ggt ggt tct ggt ggc gga tcc cag tct gag ctg aca cag cca ccc         480
Gly Gly Ser Gly Gly Gly Gly Ser Gln Ser Glu Leu Thr Gln Pro Pro
145                 150                 155                 160 tca gcg tct ggg acc ccc ggg cag agg gtc acc atc tct tgt tct gga     528
Ser Ala Ser Gly Thr Pro Gly Gln Arg Val Thr Ile Ser Cys Ser Gly
                165                 170                 175 agc agc tcc aac acc gaa act aat tat gta tac tgg tac cag cag ctc     576
Ser Ser Ser Asn Thr Glu Thr Asn Tyr Val Tyr Trp Tyr Gln Gln Leu
            180                 185                 190 ccg gga acg gcc ccc aag ctc ctc atc tct atg aac aat cac cgg ccc     624
Pro Gly Thr Ala Pro Lys Leu Leu Ile Ser Met Asn Asn His Arg Pro
        195                 200                 205
```

```
tca ggg gtc cct gac cga ttc tct ggc tcc aag tct ggc acc tca gcc      672
Ser Gly Val Pro Asp Arg Phe Ser Gly Ser Lys Ser Gly Thr Ser Ala
210                 215                 220 tcc ctg gcc atc agt ggg ctc cgg tcc gag gat gag gct gat tat tac      720
Ser Leu Ala Ile Ser Gly Leu Arg Ser Glu Asp Glu Ala Asp Tyr Tyr
225                 230                 235                 240 tgt gca gca tgg gat gac ggc ctg agt ggt ctg cgt tgg gtg ttc ggc      768
Cys Ala Ala Trp Asp Asp Gly Leu Ser Gly Leu Arg Trp Val Phe Gly
                245                 250                 255 gga ggg acc cag ctc acc gtt tta ggt gcg gcc gc                       803
Gly Gly Thr Gln Leu Thr Val Leu Gly Ala Ala
            260                 265
```

<210> SEQ ID NO 111
<211> LENGTH: 267
<212> TYPE: PRT
<213> ORGANISM: Artificial
<220> FEATURE:
<223> OTHER INFORMATION: Synthetic Construct

<400> SEQUENCE: 111

```
Ala Ala Gln Pro Ala Met Ala Gln Val Gln Leu Gln Gln Ser Gly Gly
1               5                   10                  15

Gly Leu Val Gln Pro Gly Gly Ser Leu Arg Leu Ser Cys Ala Thr Ser
            20                  25                  30

Gly Phe Thr Phe Arg Ser Tyr Asp Met Thr Trp Val Arg Gln Ala Pro
        35                  40                  45

Gly Lys Gly Leu Glu Trp Val Ser Thr Ile Ser Gly Gly Gly Arg
    50                  55                  60

Thr His Tyr Thr Asp Ser Val Lys Gly Arg Phe Thr Ile Thr Arg Asp
65                  70                  75                  80

Asn Ser Lys Ser Thr Leu Phe Leu Gln Met Asn Gly Leu Arg Ala Glu
                85                  90                  95

Asp Thr Ala Val Tyr Tyr Cys Ala Lys Gly Gly Leu Thr Ala Ser Ile
            100                 105                 110

Ala Val Val Gly Gln Leu Tyr Asp Tyr His Gly Met Asp Val Trp Gly
        115                 120                 125

Gln Gly Thr Thr Val Thr Val Ser Ser Gly Gly Gly Ser Gly Gly
    130                 135                 140

Gly Gly Ser Gly Gly Gly Ser Gln Ser Glu Leu Thr Gln Pro Pro
145                 150                 155                 160

Ser Ala Ser Gly Thr Pro Gly Gln Arg Val Thr Ile Ser Cys Ser Gly
                165                 170                 175

Ser Ser Ser Asn Thr Glu Thr Asn Tyr Val Tyr Trp Tyr Gln Gln Leu
            180                 185                 190

Pro Gly Thr Ala Pro Lys Leu Leu Ile Ser Met Asn Asn His Arg Pro
        195                 200                 205

Ser Gly Val Pro Asp Arg Phe Ser Gly Ser Lys Ser Gly Thr Ser Ala
    210                 215                 220

Ser Leu Ala Ile Ser Gly Leu Arg Ser Glu Asp Glu Ala Asp Tyr Tyr
225                 230                 235                 240

Cys Ala Ala Trp Asp Asp Gly Leu Ser Gly Leu Arg Trp Val Phe Gly
                245                 250                 255

Gly Gly Thr Gln Leu Thr Val Leu Gly Ala Ala
            260                 265
```

<210> SEQ ID NO 112

```
<211> LENGTH: 738
<212> TYPE: DNA
<213> ORGANISM: Artificial
<220> FEATURE:
<223> OTHER INFORMATION: An artificially synthesized scFv sequence
<220> FEATURE:
<221> NAME/KEY: CDS
<222> LOCATION: (1)..(738)

<400> SEQUENCE: 112 gag gtg cag ctg gtg gag tct gga gca gag gtg aaa aag ccc ggg gag       48
Glu Val Gln Leu Val Glu Ser Gly Ala Glu Val Lys Lys Pro Gly Glu
1               5                   10                  15 tct ctg aag atc tcc tgt aag ggt tct gga tac agc ttt acc agc aac       96
Ser Leu Lys Ile Ser Cys Lys Gly Ser Gly Tyr Ser Phe Thr Ser Asn
            20                  25                  30 tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45 ggg atg atc tat cct ggt gac tct gac acc atg tac agt cag tcc ttc      192
Gly Met Ile Tyr Pro Gly Asp Ser Asp Thr Met Tyr Ser Gln Ser Phe
    50                  55                  60 aaa ggc cag gtc acc ctc tca gtc gac aag tcc gtc agc acc gcc tac      240
Lys Gly Gln Val Thr Leu Ser Val Asp Lys Ser Val Ser Thr Ala Tyr
65                  70                  75                  80 ctt cag tgg agc agc ctg cag gcc tcg gac act gcc ctg tat tac tgt      288
Leu Gln Trp Ser Ser Leu Gln Ala Ser Asp Thr Ala Leu Tyr Tyr Cys
                85                  90                  95 gcg aga gcc cct aac tta agc agt gcc tgg cac tct ttt gac tac tgg      336
Ala Arg Ala Pro Asn Leu Ser Ser Ala Trp His Ser Phe Asp Tyr Trp
            100                 105                 110 ggc cag gga acc ctg gtc acc gtc tcc tca ggt ggt ggt ggt tcg ggt      384
Gly Gln Gly Thr Leu Val Thr Val Ser Ser Gly Gly Gly Gly Ser Gly
        115                 120                 125 ggt ggt ggt tct ggc ggt ggc gga tcg aat ttt atg ctg act cag ccg      432
Gly Gly Gly Ser Gly Gly Gly Gly Ser Asn Phe Met Leu Thr Gln Pro
    130                 135                 140 gct tca gtg tta gtg gcc cca gga aag acg gcc agg att acc tgt ggg      480
Ala Ser Val Leu Val Ala Pro Gly Lys Thr Ala Arg Ile Thr Cys Gly
145                 150                 155                 160 gga aac aac att gaa gat aag agt gtg cac tgg tac cag cag aag cca      528
Gly Asn Asn Ile Glu Asp Lys Ser Val His Trp Tyr Gln Gln Lys Pro
                165                 170                 175 ggc cag gcc cct gtg ctg gtc atc tat tat gat acc gac cgg ccc tca      576
Gly Gln Ala Pro Val Leu Val Ile Tyr Tyr Asp Thr Asp Arg Pro Ser
            180                 185                 190 ggg atc cct gag cga ttc tct ggc tcc aac tct ggg aac acg gcc acc      624
Gly Ile Pro Glu Arg Phe Ser Gly Ser Asn Ser Gly Asn Thr Ala Thr
        195                 200                 205 ctg acc atc agc agg gtc gaa gcc ggg gat gag gcc gac tat ttc tgt      672
Leu Thr Ile Ser Arg Val Glu Ala Gly Asp Glu Ala Asp Tyr Phe Cys
    210                 215                 220 cag gtg tgg gat agc agt agt gat cat gtg gta ttc ggc gga ggg acc      720
Gln Val Trp Asp Ser Ser Ser Asp His Val Val Phe Gly Gly Gly Thr
225                 230                 235                 240 aag ctg acc gtc cta ggt                                              738
Lys Leu Thr Val Leu Gly
                245

<210> SEQ ID NO 113
<211> LENGTH: 246
<212> TYPE: PRT
<213> ORGANISM: Artificial
```

<220> FEATURE:
<223> OTHER INFORMATION: Synthetic Construct

<400> SEQUENCE: 113

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Ser Asn
            20                  25                  30

Trp Ile Gly Trp Val Arg Gln Met Pro Gly Lys Gly Leu Glu Trp Met
        35                  40                  45

Gly Met Ile Tyr Pro Gly Asp Ser Asp Thr Met Tyr Ser Gln Ser Phe
    50                  55                  60

Lys Gly Gln Val Thr Leu Ser Val Asp Lys Ser Val Ser Thr Ala Tyr
65                  70                  75                  80

Leu Gln Trp Ser Ser Leu Gln Ala Ser Asp Thr Ala Leu Tyr Tyr Cys
                85                  90                  95

Ala Arg Ala Pro Asn Leu Ser Ser Ala Trp His Ser Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asn Phe Met Leu Thr Gln Pro
    130                 135                 140

Ala Ser Val Leu Val Ala Pro Gly Lys Thr Ala Arg Ile Thr Cys Gly
145                 150                 155                 160

Gly Asn Asn Ile Glu Asp Lys Ser Val His Trp Tyr Gln Gln Lys Pro
                165                 170                 175

Gly Gln Ala Pro Val Leu Val Ile Tyr Tyr Asp Thr Asp Arg Pro Ser
            180                 185                 190

Gly Ile Pro Glu Arg Phe Ser Gly Ser Asn Ser Gly Asn Thr Ala Thr
        195                 200                 205

Leu Thr Ile Ser Arg Val Glu Ala Gly Asp Glu Ala Asp Tyr Phe Cys
    210                 215                 220

Gln Val Trp Asp Ser Ser Ser Asp His Val Val Phe Gly Gly Gly Thr
225                 230                 235                 240

Lys Leu Thr Val Leu Gly
                245

<210> SEQ ID NO 114
<211> LENGTH: 747
<212> TYPE: DNA
<213> ORGANISM: Artificial
<220> FEATURE:
<223> OTHER INFORMATION: An artificially synthesized scFv sequence
<220> FEATURE:
<221> NAME/KEY: CDS
<222> LOCATION: (1)..(747)

<400> SEQUENCE: 114

```
cag gta cag ctg cag cag tca ggg gga gac ttg gtt cag cct ggg ggg      48
Gln Val Gln Leu Gln Gln Ser Gly Gly Asp Leu Val Gln Pro Gly Gly
1               5                   10                  15 tcc ctc aga ctc tcc tgt gca gcc tct gga ttc acc ttt gat gaa tat      96
Ser Leu Arg Leu Ser Cys Ala Ala Ser Gly Phe Thr Phe Asp Glu Tyr
            20                  25                  30 ggc atg cac tgg gtc cgt cag gct cca ggg aag ggt ctg gag tgg gtc     144
Gly Met His Trp Val Arg Gln Ala Pro Gly Lys Gly Leu Glu Trp Val
        35                  40                  45 tct ctt att agt ggg gat ggc gat tac aca tcc tat gct gac tct gtg     192
Ser Leu Ile Ser Gly Asp Gly Asp Tyr Thr Ser Tyr Ala Asp Ser Val
```

```
                  50                  55                  60
aag ggc cga ttc acc atc tcc aga gac aac aat aaa aac tcc ccg tat       240
Lys Gly Arg Phe Thr Ile Ser Arg Asp Asn Asn Lys Asn Ser Pro Tyr
 65                  70                  75                  80 ctg cga atg aac agt ctg aga act gag gac acc gcc ttg tat tac tgt       288
Leu Arg Met Asn Ser Leu Arg Thr Glu Asp Thr Ala Leu Tyr Tyr Cys
                     85                  90                  95 gca aaa gat ggg tac ccc tat ggc agg gac ttc tac tac tac atg           336
Ala Lys Asp Gly Tyr Pro Tyr Gly Arg Asp Phe Tyr Tyr Tyr Met
                100                 105                 110 gac gtc tgg ggc aaa ggg acc acg gtc acc gtc tca ggt ggt ggt           384
Asp Val Trp Gly Lys Gly Thr Thr Val Thr Val Ser Gly Gly Gly
            115                 120                 125 ggt tcg ggt ggt ggt ggc tcc ggc ggt ggc gga tcg cag tat gtg ctg       432
Gly Ser Gly Gly Gly Gly Ser Gly Gly Gly Gly Ser Gln Tyr Val Leu
        130                 135                 140 act cag cca ccc tca gtg tca gtg gcc cca gga aag acg gcc agg att       480
Thr Gln Pro Pro Ser Val Ser Val Ala Pro Gly Lys Thr Ala Arg Ile
145                 150                 155                 160 acc tgt ggg gga aac aac att gaa gat aag agt gtg cac tgg tac cag       528
Thr Cys Gly Gly Asn Asn Ile Glu Asp Lys Ser Val His Trp Tyr Gln
                165                 170                 175 cag aag cca ggc cag gcc cct gtg ctg gtc atc tat tat gat acc gac       576
Gln Lys Pro Gly Gln Ala Pro Val Leu Val Ile Tyr Tyr Asp Thr Asp
            180                 185                 190 cgg ccc tca ggg atc cct gag cga ttc tct ggc tcc aac tct ggg aac       624
Arg Pro Ser Gly Ile Pro Glu Arg Phe Ser Gly Ser Asn Ser Gly Asn
        195                 200                 205 acg gcc acc ctg acc atc agc agg gtc gaa gcc ggg gat gag gcc gac       672
Thr Ala Thr Leu Thr Ile Ser Arg Val Glu Ala Gly Asp Glu Ala Asp
    210                 215                 220 tat ttc tgt cag gcg tgg gat agc agt agt gat cat gtg gta ttc ggc       720
Tyr Phe Cys Gln Ala Trp Asp Ser Ser Ser Asp His Val Val Phe Gly
225                 230                 235                 240 gga ggg acc aag ctg acc gtc cta ggt                                   747
Gly Gly Thr Lys Leu Thr Val Leu Gly
                245

<210> SEQ ID NO 115
<211> LENGTH: 249
<212> TYPE: PRT
<213> ORGANISM: Artificial
<220> FEATURE:
<223> OTHER INFORMATION: Synthetic Construct

<400> SEQUENCE: 115

Gln Val Gln Leu Gln Gln Ser Gly Gly Asp Leu Val Gln Pro Gly Gly
 1               5                  10                  15

Ser Leu Arg Leu Ser Cys Ala Ala Ser Gly Phe Thr Phe Asp Glu Tyr
                20                  25                  30

Gly Met His Trp Val Arg Gln Ala Pro Gly Lys Gly Leu Glu Trp Val
            35                  40                  45

Ser Leu Ile Ser Gly Asp Gly Asp Tyr Thr Ser Tyr Ala Asp Ser Val
        50                  55                  60

Lys Gly Arg Phe Thr Ile Ser Arg Asp Asn Asn Lys Asn Ser Pro Tyr
 65                  70                  75                  80

Leu Arg Met Asn Ser Leu Arg Thr Glu Asp Thr Ala Leu Tyr Tyr Cys
                85                  90                  95

Ala Lys Asp Gly Tyr Pro Tyr Gly Arg Asp Phe Tyr Tyr Tyr Met
            100                 105                 110
```

```
Asp Val Trp Gly Lys Gly Thr Thr Val Thr Val Ser Ser Gly Gly Gly
        115                 120                 125
Gly Ser Gly Gly Gly Ser Gly Gly Gly Ser Gln Tyr Val Leu
    130                 135                 140
Thr Gln Pro Pro Ser Val Ser Val Ala Pro Gly Lys Thr Ala Arg Ile
145                 150                 155                 160
Thr Cys Gly Gly Asn Asn Ile Glu Asp Lys Ser Val His Trp Tyr Gln
                165                 170                 175
Gln Lys Pro Gly Gln Ala Pro Val Leu Val Ile Tyr Tyr Asp Thr Asp
            180                 185                 190
Arg Pro Ser Gly Ile Pro Glu Arg Phe Ser Gly Ser Asn Ser Gly Asn
        195                 200                 205
Thr Ala Thr Leu Thr Ile Ser Arg Val Glu Ala Gly Asp Glu Ala Asp
    210                 215                 220
Tyr Phe Cys Gln Ala Trp Asp Ser Ser Ser Asp His Val Val Phe Gly
225                 230                 235                 240
Gly Gly Thr Lys Leu Thr Val Leu Gly
                245
```

```
<210> SEQ ID NO 116
<211> LENGTH: 1509
<212> TYPE: DNA
<213> ORGANISM: Artificial
<220> FEATURE:
<223> OTHER INFORMATION: An artificially synthesized sequence that
      encodes a scFv fusion protein
<220> FEATURE:
<221> NAME/KEY: CDS
<222> LOCATION: (1)..(1509)

<400> SEQUENCE: 116
```

```
atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtc ctg tcc gag gtg cag ctg gtg gag tct gga gca gag gtg aaa aag      96
Val Leu Ser Glu Val Gln Leu Val Glu Ser Gly Ala Glu Val Lys Lys
            20                  25                  30 ccc ggg gag tct ctg aag atc tcc tgt aag ggt tct gga tac agc ttt     144
Pro Gly Glu Ser Leu Lys Ile Ser Cys Lys Gly Ser Gly Tyr Ser Phe
        35                  40                  45 acc agc aac tgg atc ggc tgg gtg cgc cag atg ccc ggg aaa ggc ctg     192
Thr Ser Asn Trp Ile Gly Trp Val Arg Gln Met Pro Gly Lys Gly Leu
    50                  55                  60 gag tgg atg ggg atg atc tat cct ggt gac tct gac acc atg tac agt     240
Glu Trp Met Gly Met Ile Tyr Pro Gly Asp Ser Asp Thr Met Tyr Ser
65                  70                  75                  80 cag tcc ttc aaa ggc cag gtc acc ctc tca gtc gac aag tcc gtc agc     288
Gln Ser Phe Lys Gly Gln Val Thr Leu Ser Val Asp Lys Ser Val Ser
                85                  90                  95 acc gcc tac ctt cag tgg agc agc ctg cag gcc tcg gac act gcc ctg     336
Thr Ala Tyr Leu Gln Trp Ser Ser Leu Gln Ala Ser Asp Thr Ala Leu
            100                 105                 110 tat tac tgt gcg aga gcc cct aac tta agc agt gcc tgg cac tct ttt     384
Tyr Tyr Cys Ala Arg Ala Pro Asn Leu Ser Ser Ala Trp His Ser Phe
        115                 120                 125 gac tac tgg ggc cag gga acc ctg gtc acc gtc tcc tca ggt ggt ggt     432
Asp Tyr Trp Gly Gln Gly Thr Leu Val Thr Val Ser Ser Gly Gly Gly
    130                 135                 140 ggt tcg ggt ggt ggt ggt tct ggc ggt ggc gga tcg aat ttt atg ctg     480
Gly Ser Gly Gly Gly Gly Ser Gly Gly Gly Gly Ser Asn Phe Met Leu
```

```
                145                 150                 155                 160
act cag ccg gct tca gtg tta gtg gcc cca gga aag acg gcc agg att        528
Thr Gln Pro Ala Ser Val Leu Val Ala Pro Gly Lys Thr Ala Arg Ile
            165                 170                 175 acc tgt ggg gga aac aac att gaa gat aag agt gtg cac tgg tac cag        576
Thr Cys Gly Gly Asn Asn Ile Glu Asp Lys Ser Val His Trp Tyr Gln
            180                 185                 190 cag aag cca ggc cag gcc cct gtg ctg gtc atc tat tat gat acc gac        624
Gln Lys Pro Gly Gln Ala Pro Val Leu Val Ile Tyr Tyr Asp Thr Asp
            195                 200                 205 cgg ccc tca ggg atc cct gag cga ttc tct ggc tcc aac tct ggg aac        672
Arg Pro Ser Gly Ile Pro Glu Arg Phe Ser Gly Ser Asn Ser Gly Asn
            210                 215                 220 acg gcc acc ctg acc atc agc agg gtc gaa gcc ggg gat gag gcc gac        720
Thr Ala Thr Leu Thr Ile Ser Arg Val Glu Ala Gly Asp Glu Ala Asp
225                 230                 235                 240 tat ttc tgt cag gtg tgg gat agc agt agt gat cat gtg gta ttc ggc        768
Tyr Phe Cys Gln Val Trp Asp Ser Ser Ser Asp His Val Val Phe Gly
            245                 250                 255 gga ggg acc aag ctg acc gtc cta ggt gcg gcc gct atg gat ccc aga        816
Gly Gly Thr Lys Leu Thr Val Leu Gly Ala Ala Ala Met Asp Pro Arg
            260                 265                 270 ggg ccc aca atc aag ccc tgt cct cca tgc aaa tgc cca gca cct aac        864
Gly Pro Thr Ile Lys Pro Cys Pro Pro Cys Lys Cys Pro Ala Pro Asn
            275                 280                 285 ctc ttg ggt gga cca tcc gtc ttc atc ttc cct cca aag atc aag gat        912
Leu Leu Gly Gly Pro Ser Val Phe Ile Phe Pro Pro Lys Ile Lys Asp
            290                 295                 300 gta ctc atg atc tcc ctg agc ccc ata gtc aca tgt gtg gtg gtg gat        960
Val Leu Met Ile Ser Leu Ser Pro Ile Val Thr Cys Val Val Val Asp
305                 310                 315                 320 gtg agc gag gat gac cca gat gtc cag atc agc tgg ttt gtg aac aac       1008
Val Ser Glu Asp Asp Pro Asp Val Gln Ile Ser Trp Phe Val Asn Asn
            325                 330                 335 gtg gaa gta cac aca gct cag aca caa acc cat aga gag gat tac aac       1056
Val Glu Val His Thr Ala Gln Thr Gln Thr His Arg Glu Asp Tyr Asn
            340                 345                 350 agt act ctc cgg gtg gtc agt gcc ctc ccc atc cag cac cag gac tgg       1104
Ser Thr Leu Arg Val Val Ser Ala Leu Pro Ile Gln His Gln Asp Trp
            355                 360                 365 atg agt ggc aag gag ttc aaa tgc aag gtc aac aac aaa gac ctc cca       1152
Met Ser Gly Lys Glu Phe Lys Cys Lys Val Asn Asn Lys Asp Leu Pro
            370                 375                 380 gcg ccc atc gag aga acc atc tca aaa ccc aaa ggg tca gta aga gca       1200
Ala Pro Ile Glu Arg Thr Ile Ser Lys Pro Lys Gly Ser Val Arg Ala
385                 390                 395                 400 cca cag gta tat gtc ttg cct cca cca gaa gaa gag atg act aag aaa       1248
Pro Gln Val Tyr Val Leu Pro Pro Pro Glu Glu Glu Met Thr Lys Lys
            405                 410                 415 cag gtc act ctg acc tgc atg gtc aca gac ttc atg cct gaa gac att       1296
Gln Val Thr Leu Thr Cys Met Val Thr Asp Phe Met Pro Glu Asp Ile
            420                 425                 430 tac gtg gag tgg acc aac aac ggg aaa aca gag cta aac tac aag aac       1344
Tyr Val Glu Trp Thr Asn Asn Gly Lys Thr Glu Leu Asn Tyr Lys Asn
            435                 440                 445 act gaa cca gtc ctg gac tct gat ggt tct tac ttc atg tac agc aag       1392
Thr Glu Pro Val Leu Asp Ser Asp Gly Ser Tyr Phe Met Tyr Ser Lys
            450                 455                 460 ctg aga gtg gaa aag aag aac tgg gtg gaa aga aat agc tac tcc tgt       1440
Leu Arg Val Glu Lys Lys Asn Trp Val Glu Arg Asn Ser Tyr Ser Cys
```

```
                465                 470                 475                 480
tca gtg gtc cac gag ggt ctg cac aat cac cac acg act aag agc ttc        1488
Ser Val Val His Glu Gly Leu His Asn His His Thr Thr Lys Ser Phe
                    485                 490                 495 tcc cgg act ccg ggt aaa tga                                            1509
Ser Arg Thr Pro Gly Lys
                500

<210> SEQ ID NO 117
<211> LENGTH: 502
<212> TYPE: PRT
<213> ORGANISM: Artificial
<220> FEATURE:
<223> OTHER INFORMATION: Synthetic Construct

<400> SEQUENCE: 117

Met Lys His Leu Trp Phe Phe Leu Leu Leu Val Ala Ala Pro Arg Trp
1               5                   10                  15

Val Leu Ser Glu Val Gln Leu Val Glu Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Asn Trp Ile Gly Trp Val Arg Gln Met Pro Gly Lys Gly Leu
    50                  55                  60

Glu Trp Met Gly Met Ile Tyr Pro Gly Asp Ser Asp Thr Met Tyr Ser
65                  70                  75                  80

Gln Ser Phe Lys Gly Gln Val Thr Leu Ser Val Asp Lys Ser Val Ser
                85                  90                  95

Thr Ala Tyr Leu Gln Trp Ser Ser Leu Gln Ala Ser Asp Thr Ala Leu
            100                 105                 110

Tyr Tyr Cys Ala Arg Ala Pro Asn Leu Ser Ser Ala Trp His Ser Phe
        115                 120                 125

Asp Tyr Trp Gly Gln Gly Thr Leu Val Thr Val Ser Ser Gly Gly Gly
    130                 135                 140

Gly Ser Gly Gly Gly Ser Gly Gly Gly Ser Asn Phe Met Leu
145                 150                 155                 160

Thr Gln Pro Ala Ser Val Leu Val Ala Pro Gly Lys Thr Ala Arg Ile
                165                 170                 175

Thr Cys Gly Gly Asn Asn Ile Glu Asp Lys Ser Val His Trp Tyr Gln
            180                 185                 190

Gln Lys Pro Gly Gln Ala Pro Val Leu Val Ile Tyr Tyr Asp Thr Asp
        195                 200                 205

Arg Pro Ser Gly Ile Pro Glu Arg Phe Ser Gly Ser Asn Ser Gly Asn
    210                 215                 220

Thr Ala Thr Leu Thr Ile Ser Arg Val Glu Ala Gly Asp Glu Ala Asp
225                 230                 235                 240

Tyr Phe Cys Gln Val Trp Asp Ser Ser Asp His Val Val Phe Gly
                245                 250                 255

Gly Gly Thr Lys Leu Thr Val Leu Gly Ala Ala Ala Met Asp Pro Arg
            260                 265                 270

Gly Pro Thr Ile Lys Pro Cys Pro Pro Cys Lys Cys Pro Ala Pro Asn
        275                 280                 285

Leu Leu Gly Gly Pro Ser Val Phe Ile Phe Pro Pro Lys Ile Lys Asp
    290                 295                 300

Val Leu Met Ile Ser Leu Ser Pro Ile Val Thr Cys Val Val Val Asp
305                 310                 315                 320
```

```
Val Ser Glu Asp Asp Pro Asp Val Gln Ile Ser Trp Phe Val Asn Asn
                325                 330                 335

Val Glu Val His Thr Ala Gln Thr Gln Thr His Arg Glu Asp Tyr Asn
            340                 345                 350

Ser Thr Leu Arg Val Val Ser Ala Leu Pro Ile Gln His Gln Asp Trp
        355                 360                 365

Met Ser Gly Lys Glu Phe Lys Cys Lys Val Asn Asn Lys Asp Leu Pro
    370                 375                 380

Ala Pro Ile Glu Arg Thr Ile Ser Lys Pro Lys Gly Ser Val Arg Ala
385                 390                 395                 400

Pro Gln Val Tyr Val Leu Pro Pro Glu Glu Glu Met Thr Lys Lys
                405                 410                 415

Gln Val Thr Leu Thr Cys Met Val Thr Asp Phe Met Pro Glu Asp Ile
                420                 425                 430

Tyr Val Glu Trp Thr Asn Asn Gly Lys Thr Glu Leu Asn Tyr Lys Asn
            435                 440                 445

Thr Glu Pro Val Leu Asp Ser Asp Gly Ser Tyr Phe Met Tyr Ser Lys
        450                 455                 460

Leu Arg Val Glu Lys Lys Asn Trp Val Glu Arg Asn Ser Tyr Ser Cys
465                 470                 475                 480

Ser Val Val His Glu Gly Leu His Asn His His Thr Thr Lys Ser Phe
                485                 490                 495

Ser Arg Thr Pro Gly Lys
            500

<210> SEQ ID NO 118
<211> LENGTH: 753
<212> TYPE: DNA
<213> ORGANISM: Artificial
<220> FEATURE:
<223> OTHER INFORMATION: An artificially synthesized scFv sequence
<220> FEATURE:
<221> NAME/KEY: CDS
<222> LOCATION: (1)..(753)

<400> SEQUENCE: 118 cag gta cag ctg cag cag tca ggc cca gga ctg gtg aag cct tcg gag     48
Gln Val Gln Leu Gln Gln Ser Gly Pro Gly Leu Val Lys Pro Ser Glu
1               5                   10                  15 gcc ctg tcc ctc acg tgc agt gtc tct ggt gac tcc att gcc agg agt     96
Ala Leu Ser Leu Thr Cys Ser Val Ser Gly Asp Ser Ile Ala Arg Ser
            20                  25                  30 cgt tac tat tgg ggc tgg atc cgc cag tcc cca ggg aag ggg ctg gag    144
Arg Tyr Tyr Trp Gly Trp Ile Arg Gln Ser Pro Gly Lys Gly Leu Glu
        35                  40                  45 tgg att ggg agt atc tac tat agt ggg acc acc tac tac aac ccg tcc    192
Trp Ile Gly Ser Ile Tyr Tyr Ser Gly Thr Thr Tyr Tyr Asn Pro Ser
    50                  55                  60 ctc aag agt cgc gtc acc ata tcc gta gac acg tcc aag aac gac ttc    240
Leu Lys Ser Arg Val Thr Ile Ser Val Asp Thr Ser Lys Asn Asp Phe
65                  70                  75                  80 tcc cta aac ctg agg tct ctg agc gcc aca gac acg gct gta tat tac    288
Ser Leu Asn Leu Arg Ser Leu Ser Ala Thr Asp Thr Ala Val Tyr Tyr
                85                  90                  95 tgt gcg aga cag act ggg gac gtt acc gag gac cgc gag ttt gac tac    336
Cys Ala Arg Gln Thr Gly Asp Val Thr Glu Asp Arg Glu Phe Asp Tyr
            100                 105                 110 tgg ggc cag gga acc ctg gtc acc gtc tcc tca ggt ggt ggt ggt tcg    384
Trp Gly Gln Gly Thr Leu Val Thr Val Ser Ser Gly Gly Gly Gly Ser
        115                 120                 125
```

```
ggt ggt ggt ggt tcg ggt ggt ggc gga tcg gat gtt gtg atg act cag    432
Gly Gly Gly Gly Ser Gly Gly Gly Gly Ser Asp Val Val Met Thr Gln
        130                 135                 140 tct cca gac tcc ctg gct gtg tct ctg ggc gag agg gcc acc atc aac    480
Ser Pro Asp Ser Leu Ala Val Ser Leu Gly Glu Arg Ala Thr Ile Asn
145                 150                 155                 160 tgc aag tcc agc cag agt gtt tta tac agc tcc aat tat aag aac tac    528
Cys Lys Ser Ser Gln Ser Val Leu Tyr Ser Ser Asn Tyr Lys Asn Tyr
                165                 170                 175 ttg gct tgg tac cag cag aaa cca gga gag cct cct agg ctg ctc ttt    576
Leu Ala Trp Tyr Gln Gln Lys Pro Gly Glu Pro Pro Arg Leu Leu Phe
            180                 185                 190 tac tgg gca tct acc cgg cat tcc ggg gtc cct gac cga ttc agt ggc    624
Tyr Trp Ala Ser Thr Arg His Ser Gly Val Pro Asp Arg Phe Ser Gly
        195                 200                 205 agc ggg tct ggg aca gat ttc act ctc acc atc acc agc ctg cag gct    672
Ser Gly Ser Gly Thr Asp Phe Thr Leu Thr Ile Thr Ser Leu Gln Ala
    210                 215                 220 gaa gat gtg gga gtt tat ttc tgt cag caa tat tat gat gct gtc acc    720
Glu Asp Val Gly Val Tyr Phe Cys Gln Gln Tyr Tyr Asp Ala Val Thr
225                 230                 235                 240 ttc ggc caa ggg acc aag gtg gag atc aaa cgt                        753
Phe Gly Gln Gly Thr Lys Val Glu Ile Lys Arg
                245                 250

<210> SEQ ID NO 119
<211> LENGTH: 251
<212> TYPE: PRT
<213> ORGANISM: Artificial
<220> FEATURE:
<223> OTHER INFORMATION: Synthetic Construct

<400> SEQUENCE: 119

Gln Val Gln Leu Gln Gln Ser Gly Pro Gly Leu Val Lys Pro Ser Glu
1               5                   10                  15

Ala Leu Ser Leu Thr Cys Ser Val Ser Gly Asp Ser Ile Ala Arg Ser
            20                  25                  30

Arg Tyr Tyr Trp Gly Trp Ile Arg Gln Ser Pro Gly Lys Gly Leu Glu
        35                  40                  45

Trp Ile Gly Ser Ile Tyr Tyr Ser Gly Thr Thr Tyr Tyr Asn Pro Ser
    50                  55                  60

Leu Lys Ser Arg Val Thr Ile Ser Val Asp Thr Ser Lys Asn Asp Phe
65                  70                  75                  80

Ser Leu Asn Leu Arg Ser Leu Ser Ala Thr Asp Thr Ala Val Tyr Tyr
                85                  90                  95

Cys Ala Arg Gln Thr Gly Asp Val Thr Glu Asp Arg Glu Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Val Val Met Thr Gln
    130                 135                 140

Ser Pro Asp Ser Leu Ala Val Ser Leu Gly Glu Arg Ala Thr Ile Asn
145                 150                 155                 160

Cys Lys Ser Ser Gln Ser Val Leu Tyr Ser Ser Asn Tyr Lys Asn Tyr
                165                 170                 175

Leu Ala Trp Tyr Gln Gln Lys Pro Gly Glu Pro Pro Arg Leu Leu Phe
            180                 185                 190

Tyr Trp Ala Ser Thr Arg His Ser Gly Val Pro Asp Arg Phe Ser Gly
```

-continued

```
                195                 200                 205
Ser Gly Ser Gly Thr Asp Phe Thr Leu Thr Ile Thr Ser Leu Gln Ala
    210                 215                 220

Glu Asp Val Gly Val Tyr Phe Cys Gln Gln Tyr Tyr Asp Ala Val Thr
225                 230                 235                 240

Phe Gly Gln Gly Thr Lys Val Glu Ile Lys Arg
                245                 250

<210> SEQ ID NO 120
<211> LENGTH: 1524
<212> TYPE: DNA
<213> ORGANISM: Artificial
<220> FEATURE:
<223> OTHER INFORMATION: An artificially synthesized sequence that
      encodes a scFv fusion protein
<220> FEATURE:
<221> NAME/KEY: CDS
<222> LOCATION: (1)..(1524)

<400> SEQUENCE: 120
```

| | | | | | | | | | | | | | | | | |
|---|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |
| gtc | ctg | tcc | cag | gta | cag | ctg | cag | cag | tca | ggc | cca | gga | ctg | gtg | aag | 96 |
| Val | Leu | Ser | Gln | Val | Gln | Leu | Gln | Gln | Ser | Gly | Pro | Gly | Leu | Val | Lys | |
| | | | 20 | | | | | 25 | | | | | 30 | | | |
| cct | tcg | gag | gcc | ctg | tcc | ctc | acg | tgc | agt | gtc | tct | ggt | gac | tcc | att | 144 |
| Pro | Ser | Glu | Ala | Leu | Ser | Leu | Thr | Cys | Ser | Val | Ser | Gly | Asp | Ser | Ile | |
| | | 35 | | | | | 40 | | | | | 45 | | | | |
| gcc | agg | agt | cgt | tac | tat | tgg | ggc | tgg | atc | cgc | cag | tcc | cca | ggg | aag | 192 |
| Ala | Arg | Ser | Arg | Tyr | Tyr | Trp | Gly | Trp | Ile | Arg | Gln | Ser | Pro | Gly | Lys | |
| | 50 | | | | | 55 | | | | | 60 | | | | | |
| ggg | ctg | gag | tgg | att | ggg | agt | atc | tac | tat | agt | ggg | acc | acc | tac | tac | 240 |
| Gly | Leu | Glu | Trp | Ile | Gly | Ser | Ile | Tyr | Tyr | Ser | Gly | Thr | Thr | Tyr | Tyr | |
| 65 | | | | | 70 | | | | | 75 | | | | | 80 | |
| aac | ccg | tcc | ctc | aag | agt | cgc | gtc | acc | ata | tcc | gta | gac | acg | tcc | aag | 288 |
| Asn | Pro | Ser | Leu | Lys | Ser | Arg | Val | Thr | Ile | Ser | Val | Asp | Thr | Ser | Lys | |
| | | | | 85 | | | | | 90 | | | | | 95 | | |
| aac | gac | ttc | tcc | cta | aac | ctg | agg | tct | ctg | agc | gcc | aca | gac | acg | gct | 336 |
| Asn | Asp | Phe | Ser | Leu | Asn | Leu | Arg | Ser | Leu | Ser | Ala | Thr | Asp | Thr | Ala | |
| | | | 100 | | | | | 105 | | | | | 110 | | | |
| gta | tat | tac | tgt | gcg | aga | cag | act | ggg | gac | gtt | acc | gag | gac | cgc | gag | 384 |
| Val | Tyr | Tyr | Cys | Ala | Arg | Gln | Thr | Gly | Asp | Val | Thr | Glu | Asp | Arg | Glu | |
| | | 115 | | | | | 120 | | | | | 125 | | | | |
| ttt | gac | tac | tgg | ggc | cag | gga | acc | ctg | gtc | acc | gtc | tcc | tca | ggt | ggt | 432 |
| Phe | Asp | Tyr | Trp | Gly | Gln | Gly | Thr | Leu | Val | Thr | Val | Ser | Ser | Gly | Gly | |
| | 130 | | | | | 135 | | | | | 140 | | | | | |
| ggt | ggt | tcg | ggt | ggt | ggt | ggt | tcg | ggt | ggt | ggc | gga | tcg | gat | gtt | gtg | 480 |
| Gly | Gly | Ser | Gly | Gly | Gly | Gly | Ser | Gly | Gly | Gly | Gly | Ser | Asp | Val | Val | |
| 145 | | | | | 150 | | | | | 155 | | | | | 160 | |
| atg | act | cag | tct | cca | gac | tcc | ctg | gct | gtg | tct | ctg | ggc | gag | agg | gcc | 528 |
| Met | Thr | Gln | Ser | Pro | Asp | Ser | Leu | Ala | Val | Ser | Leu | Gly | Glu | Arg | Ala | |
| | | | | 165 | | | | | 170 | | | | | 175 | | |
| acc | atc | aac | tgc | aag | tcc | agc | cag | agt | gtt | tta | tac | agc | tcc | aat | tat | 576 |
| Thr | Ile | Asn | Cys | Lys | Ser | Ser | Gln | Ser | Val | Leu | Tyr | Ser | Ser | Asn | Tyr | |
| | | | 180 | | | | | 185 | | | | | 190 | | | |
| aag | aac | tac | ttg | gct | tgg | tac | cag | cag | aaa | cca | gga | gag | cct | cct | agg | 624 |
| Lys | Asn | Tyr | Leu | Ala | Trp | Tyr | Gln | Gln | Lys | Pro | Gly | Glu | Pro | Pro | Arg | |
| | | 195 | | | | | 200 | | | | | 205 | | | | |
| ctg | ctc | ttt | tac | tgg | gca | tct | acc | cgg | cat | tcc | ggg | gtc | cct | gac | cga | 672 |
| Leu | Leu | Phe | Tyr | Trp | Ala | Ser | Thr | Arg | His | Ser | Gly | Val | Pro | Asp | Arg | |
| | 210 | | | | | 215 | | | | | 220 | | | | | |

```
ttc agt ggc agc ggg tct ggg aca gat ttc act ctc acc atc acc agc      720
Phe Ser Gly Ser Gly Ser Gly Thr Asp Phe Thr Leu Thr Ile Thr Ser
225                 230                 235                 240 ctg cag gct gaa gat gtg gga gtt tat ttc tgt cag caa tat tat gat      768
Leu Gln Ala Glu Asp Val Gly Val Tyr Phe Cys Gln Gln Tyr Tyr Asp
            245                 250                 255 gct gtc acc ttc ggc caa ggg acc aag gtg gag atc aaa cgt gcg gcc      816
Ala Val Thr Phe Gly Gln Gly Thr Lys Val Glu Ile Lys Arg Ala Ala
        260                 265                 270 gct atg gat ccc aga ggg ccc aca atc aag ccc tgt cct cca tgc aaa      864
Ala Met Asp Pro Arg Gly Pro Thr Ile Lys Pro Cys Pro Pro Cys Lys
    275                 280                 285 tgc cca gca cct aac ctc ttg ggt gga cca tcc gtc ttc atc ttc cct      912
Cys Pro Ala Pro Asn Leu Leu Gly Gly Pro Ser Val Phe Ile Phe Pro
290                 295                 300 cca aag atc aag gat gta ctc atg atc tcc ctg agc ccc ata gtc aca      960
Pro Lys Ile Lys Asp Val Leu Met Ile Ser Leu Ser Pro Ile Val Thr
305                 310                 315                 320 tgt gtg gtg gtg gat gtg agc gag gat gac cca gat gtc cag atc agc     1008
Cys Val Val Val Asp Val Ser Glu Asp Asp Pro Asp Val Gln Ile Ser
            325                 330                 335 tgg ttt gtg aac aac gtg gaa gta cac aca gct cag aca caa acc cat     1056
Trp Phe Val Asn Asn Val Glu Val His Thr Ala Gln Thr Gln Thr His
        340                 345                 350 aga gag gat tac aac agt act ctc cgg gtg gtc agt gcc ctc ccc atc     1104
Arg Glu Asp Tyr Asn Ser Thr Leu Arg Val Val Ser Ala Leu Pro Ile
    355                 360                 365 cag cac cag gac tgg atg agt ggc aag gag ttc aaa tgc aag gtc aac     1152
Gln His Gln Asp Trp Met Ser Gly Lys Glu Phe Lys Cys Lys Val Asn
370                 375                 380 aac aaa gac ctc cca gcg ccc atc gag aga acc atc tca aaa ccc aaa     1200
Asn Lys Asp Leu Pro Ala Pro Ile Glu Arg Thr Ile Ser Lys Pro Lys
385                 390                 395                 400 ggg tca gta aga gca cca cag gta tat gtc ttg cct cca cca gaa gaa     1248
Gly Ser Val Arg Ala Pro Gln Val Tyr Val Leu Pro Pro Pro Glu Glu
            405                 410                 415 gag atg act aag aaa cag gtc act ctg acc tgc atg gtc aca gac ttc     1296
Glu Met Thr Lys Lys Gln Val Thr Leu Thr Cys Met Val Thr Asp Phe
        420                 425                 430 atg cct gaa gac att tac gtg gag tgg acc aac aac ggg aaa aca gag     1344
Met Pro Glu Asp Ile Tyr Val Glu Trp Thr Asn Asn Gly Lys Thr Glu
    435                 440                 445 cta aac tac aag aac act gaa cca gtc ctg gac tct gat ggt tct tac     1392
Leu Asn Tyr Lys Asn Thr Glu Pro Val Leu Asp Ser Asp Gly Ser Tyr
450                 455                 460 ttc atg tac agc aag ctg aga gtg gaa aag aac tgg gtg gaa aga         1440
Phe Met Tyr Ser Lys Leu Arg Val Glu Lys Asn Trp Val Glu Arg
465                 470                 475                 480 aat agc tac tcc tgt tca gtg gtc cac gag ggt ctg cac aat cac cac     1488
Asn Ser Tyr Ser Cys Ser Val Val His Glu Gly Leu His Asn His His
            485                 490                 495 acg act aag agc ttc tcc cgg act ccg ggt aaa tga                     1524
Thr Thr Lys Ser Phe Ser Arg Thr Pro Gly Lys
        500                 505

<210> SEQ ID NO 121
<211> LENGTH: 507
<212> TYPE: PRT
<213> ORGANISM: Artificial
<220> FEATURE:
<223> OTHER INFORMATION: Synthetic Construct
```

<400> SEQUENCE: 121

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Pro Gly Leu Val Lys
            20                  25                  30

Pro Ser Glu Ala Leu Ser Leu Thr Cys Ser Val Ser Gly Asp Ser Ile
        35                  40                  45

Ala Arg Ser Arg Tyr Tyr Trp Gly Trp Ile Arg Gln Ser Pro Gly Lys
    50                  55                  60

Gly Leu Glu Trp Ile Gly Ser Ile Tyr Tyr Ser Gly Thr Thr Tyr Tyr
65                  70                  75                  80

Asn Pro Ser Leu Lys Ser Arg Val Thr Ile Ser Val Asp Thr Ser Lys
                85                  90                  95

Asn Asp Phe Ser Leu Asn Leu Arg Ser Leu Ser Ala Thr Asp Thr Ala
            100                 105                 110

Val Tyr Tyr Cys Ala Arg Gln Thr Gly Asp Val Thr Glu Asp Arg Glu
        115                 120                 125

Phe Asp Tyr Trp Gly Gln Gly Thr Leu Val Thr Val Ser Ser Gly Gly
    130                 135                 140

Gly Gly Ser Gly Gly Gly Ser Gly Gly Gly Ser Asp Val Val
145                 150                 155                 160

Met Thr Gln Ser Pro Asp Ser Leu Ala Val Ser Leu Gly Glu Arg Ala
                165                 170                 175

Thr Ile Asn Cys Lys Ser Ser Gln Ser Val Leu Tyr Ser Ser Asn Tyr
            180                 185                 190

Lys Asn Tyr Leu Ala Trp Tyr Gln Gln Lys Pro Gly Glu Pro Pro Arg
        195                 200                 205

Leu Leu Phe Tyr Trp Ala Ser Thr Arg His Ser Gly Val Pro Asp Arg
    210                 215                 220

Phe Ser Gly Ser Gly Ser Gly Thr Asp Phe Thr Leu Thr Ile Thr Ser
225                 230                 235                 240

Leu Gln Ala Glu Asp Val Gly Val Tyr Phe Cys Gln Gln Tyr Tyr Asp
                245                 250                 255

Ala Val Thr Phe Gly Gln Gly Thr Lys Val Glu Ile Lys Arg Ala Ala
            260                 265                 270

Ala Met Asp Pro Arg Gly Pro Thr Ile Lys Pro Cys Pro Pro Cys Lys
        275                 280                 285

Cys Pro Ala Pro Asn Leu Leu Gly Gly Pro Ser Val Phe Ile Phe Pro
    290                 295                 300

Pro Lys Ile Lys Asp Val Leu Met Ile Ser Leu Ser Pro Ile Val Thr
305                 310                 315                 320

Cys Val Val Val Asp Val Ser Glu Asp Asp Pro Asp Val Gln Ile Ser
                325                 330                 335

Trp Phe Val Asn Asn Val Glu Val His Thr Ala Gln Thr Gln Thr His
            340                 345                 350

Arg Glu Asp Tyr Asn Ser Thr Leu Arg Val Val Ser Ala Leu Pro Ile
        355                 360                 365

Gln His Gln Asp Trp Met Ser Gly Lys Glu Phe Lys Cys Lys Val Asn
    370                 375                 380

Asn Lys Asp Leu Pro Ala Pro Ile Glu Arg Thr Ile Ser Lys Pro Lys
385                 390                 395                 400

Gly Ser Val Arg Ala Pro Gln Val Tyr Val Leu Pro Pro Pro Glu Glu
                405                 410                 415
```

```
Glu Met Thr Lys Lys Gln Val Thr Leu Thr Cys Met Val Thr Asp Phe
            420             425                 430

Met Pro Glu Asp Ile Tyr Val Glu Trp Thr Asn Asn Gly Lys Thr Glu
        435             440                 445

Leu Asn Tyr Lys Asn Thr Glu Pro Val Leu Asp Ser Asp Gly Ser Tyr
        450             455             460

Phe Met Tyr Ser Lys Leu Arg Val Glu Lys Lys Asn Trp Val Glu Arg
465             470             475                         480

Asn Ser Tyr Ser Cys Ser Val Val His Glu Gly Leu His Asn His His
                485             490                     495

Thr Thr Lys Ser Phe Ser Arg Thr Pro Gly Lys
            500             505
```